(12) United States Patent
Wolf et al.

(10) Patent No.: US 6,586,185 B2
(45) Date of Patent: Jul. 1, 2003

(54) USE OF POLYPEPTIDES OR NUCLEIC ACIDS FOR THE DIAGNOSIS OR TREATMENT OF SKIN DISORDERS AND WOUND HEALING AND FOR THE IDENTIFICATION OF PHARMACOLOGICALLY ACTIVE SUBSTANCES

(75) Inventors: Eckard Wolf, Oberschleissheim (DE); Sabine Werner, Zürich (CH); Jörn-Peter Halle, Penzberg (DE); Johannes Regenbogen, Martinsried (DE); Andreas Goppelt, München (DE)

(73) Assignee: Switch Biotech AG, Neuried (DE)

( * ) Notice: Subject to any disclaimer, the term of this patent is extended or adjusted under 35 U.S.C. 154(b) by 0 days.

(21) Appl. No.: 09/886,319

(22) Filed: Jun. 20, 2001

(65) Prior Publication Data

US 2002/0086019 A1 Jul. 4, 2002

Related U.S. Application Data

(60) Provisional application No. 60/222,081, filed on Aug. 1, 2000.

(30) Foreign Application Priority Data

Jun. 20, 2000 (DE) .......................................... 100 30 149

(51) Int. Cl.[7] ........................... C12Q 1/68; A01N 43/04; A61K 49/00
(52) U.S. Cl. ............................... 435/6; 514/44; 424/9.1
(58) Field of Search ........................... 514/44; 424/9.1; 435/6

(56) References Cited

U.S. PATENT DOCUMENTS

| | | |
|---|---|---|
| 4,659,694 A | 4/1987 | Horecker |
| 4,716,148 A | 12/1987 | Horecker |
| 5,212,297 A | 5/1993 | Colella et al. |
| 5,470,970 A | 11/1995 | Sager et al. |
| 5,504,003 A | 4/1996 | Li et al. |
| 5,663,059 A | 9/1997 | Hawkins et al. |
| 5,801,001 A | 9/1998 | Sager et al. |
| 5,811,520 A | 9/1998 | Hawkins et al. |
| 5,837,537 A | 11/1998 | Campbell et al. |
| 5,892,016 A | 4/1999 | Brie et al. |
| 5,905,023 A | 5/1999 | Sager et al. |
| 5,948,626 A | 9/1999 | Hawkins et al. |

FOREIGN PATENT DOCUMENTS

| | | |
|---|---|---|
| EP | 3724524581 | 2/1989 |
| EP | 0 905 240 | 3/1999 |
| EP | 0 905 241 | 3/1999 |
| EP | 0 906 954 | 4/1999 |
| EP | 0 475 746 | 7/2000 |
| EP | 0 488 900 | 2/2001 |
| WO | WO 88/09384 | 12/1988 |
| WO | WO 99/34004 | 7/1989 |
| WO | WO 91/02077 | 2/1991 |
| WO | WO 94/05804 | 3/1994 |
| WO | WO 95/04158 | 2/1995 |
| WO | WO 95/14772 | 6/1995 |
| WO | WO 95/28497 | 10/1995 |
| WO | WO 96/33278 | 10/1996 |
| WO | WO 96/34891 | 11/1996 |
| WO | WO 97/25247 | 7/1997 |
| WO | WO 98/02459 | 1/1998 |
| WO | WO 98/14582 | 4/1998 |
| WO | WO 98/47923 | 10/1998 |
| WO | WO 98/53071 | 11/1998 |
| WO | WO 99/12968 | 3/1999 |
| WO | WO 99/28473 | 6/1999 |
| WO | WO 99/38882 | 8/1999 |
| WO | WO 00/06190 | 2/2000 |
| WO | WO 00/58473 | 10/2000 |
| WO | WO 00/73454 | 12/2000 |

OTHER PUBLICATIONS

Abrahamson et al., "Molecular Cloning and Sequence Analysis of cDNA Coding for the Precusor of the Human Cysteine Proteinase Inhibitor Cystatin C," *FEBS Letters* 216:229–233 (1987).

Aksoy et al., "Human Liver Nicotinamide N–Methyltransferase," *The Journal of Biological Chemistry* 269: 14835–14840 (1994).

Apte et al. "The Highly Conserved Defender Against the Death 1 (DAD1) Gene Maps to Human Chromosome 14q11–q12 and Mouse Chromosome 14 and Has Plant and Nematode Homologs," *FEBS Letters* 363:304–306 (1995).

Crackower et al., "Characterization of the Split Hand/Split Foot Malformation Locus SHFM1 at 7q21.3–q22.1 and Analysis of a Candidate Gene for its Expression During Limb Development," *Human Molecular Genetics* 5:571–579 (1996).

Dohrmann et al., "Dynamic Expression of TSC–22 at Sites of Epithelial–Mesenchymal Interactions During Mouse Development," *Mechanisms of Development* 84:147–151 (1999).

Erhardt et al., "B–Raf Inhibits Programmed Cell Death Downstream of Cytochrome c Release from Mitochondria by Activating the MEK/Erk Pathway," *Molecular and Cellular Biology* 19:5308–5315 (1999).

Eschenfeldt et al., "The Human Prothymosin α Gene is Polymorphic and Induced Upon Growth Stimulation: Evidence using a Cloned cDNA," *Proc. Natl. Acad. Sci.* 83:9403–9407 (1986).

Evers et al., "Molecular Coevolution of Mammalian Ribosomal Gene Terminator Sequences and the Transcription Termination Factor TTF–I," *Proc. Nat. Acad. Sci. USA* 92: 5827–5831 (1995).

(List continued on next page.)

Primary Examiner—Anne-Marie Falk
Assistant Examiner—Daniel M Sullivan
(74) Attorney, Agent, or Firm—Clark & Elbing LLP

(57) ABSTRACT

Method of using of polypeptides or nucleic acids encoding these for the diagnosis and/or prevention and/or treatment of diseases of skin cells and/or of wound healing and/or its pathological disorders, and their use for the identification of pharmacologically active substance.

3 Claims, 3 Drawing Sheets

OTHER PUBLICATIONS

Figure 1:
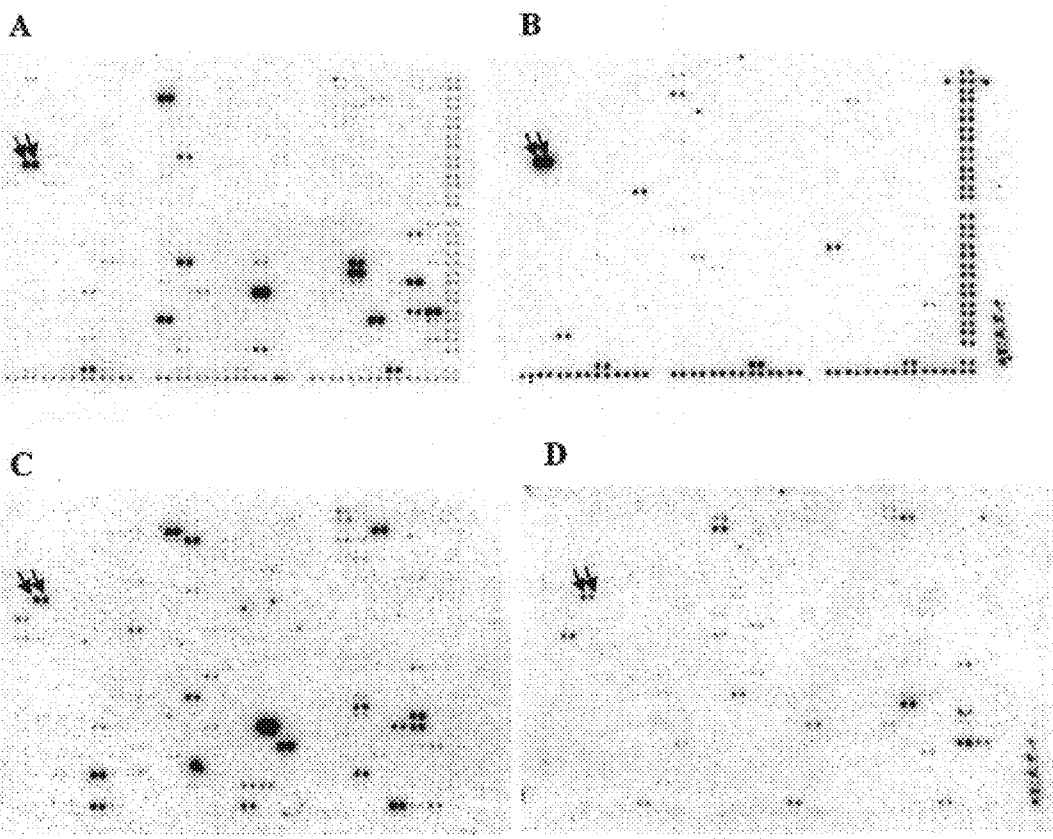

Fazioli et al., "Eps8, a Substrate for the Epidermal Growth Factor Receptor Kinase, Enhances EGF–Dependent Mitogenic Signals," *EMBO J.* 12:3799–3808 (1993).

Finch et al., "Altered Expression of Keratinocyte Growth Factor and Its Receptor in Psoriasis," *American Journal of Pathology* 15:1619–1628 (1997).

Gao et al., "Identification of a Mouse Eosinophil Receptor for the CC Chemokine Eotaxin," *Biochemical and Biophysical Research Communications* 223:679–684 (1996).

Haelens et al., "Leukocyte Migration and Activation by Murine Chemokines," *Immunobiology* 195:499–521 (1996).

Hao et al., "Isolation and Sequence Analysis of a Novel Human Tyrosine Kinase Gene," *Molecular and Cellular Biology* 9:1587–1593 (1989).

Hao et al., "Nuclear and Cytoplasmic Location of the FER Tyrosine Kinase," *Molecular and Cellular Biology* 11:1180–1183 (1991).

Hart et al., "Mutations of the Cathepsin C Gene are Responsible for Papillon–Lefevre Syndrome," *J Med Genet* 36:881–887 (1999).

Herrera et al., "Specific Acetylation of Chromosomal Protein HMG–17 by PCAF Alters Its Interaction with Nucleosomes," *Molecular and Cellular Biology* 19:3466–3473 (1999).

Hershko et al., "The Ubiquitin System," *Annu. Rev. Biochem.* 67:425–79 (1998).

Hogue et al., "A Mammalian Lysosomal Membrane Protein Confers Multidrug Resistance Upon Expression in *Saccharomyces cerevisiae*," *The Journal of Biological Chemistry* 27: 12877–12882 (1999).

Hong et al., "In Vivo Overexpression of Dad1, the Defender Against Apoptotic Death–1, Enhances T Cell Proliferation But Does Not Protect Against Apoptosis," *Journal of Immunology* 163:1888–1893 (1999).

Hoshino et al., "Methylation of Nicotinamide in Rat Liver Cytosol and its Correlation with Hepatocellular Proliferation," *Biochimica et Biophysica Acta* 719:518–526 (1982).

Iwama et al., "Dimeric RFX Proteins Contribute to the Activity and Lineage Specificity of the Interleukin–5 Receptor α Promoter Through Activation and Repression Domains," *Molecular and Cellular Biology* 19:3940–3950, (1999).

Jay et al., "Cloning of the Human Homologue of the TGFβ–Stimulated Clone 22 Gene," *Biochemical and Biophysical Research Communications* 222:821–826 (1996).

Kester, "Transforming Growth Factor–β–Stimulated Clone–22 is a Member of a Family of Leucine Zipper Proteins That Can Homo– and Heterodimerize and has Transcriptional Repressor Activity," *The Journal of Biological Chemistry* 274:27439–27447 (1999).

Kozak et al., "Mapping of the Mouse Macrophage Inflammatory Protein–1α Receptor Gene Scya3r and Two Related Mouse β Chemokine Receptor–Like Genes to Chromosome 9," *Genomics* 29:294–296 (1995).

Krajewski et al., "Immunohistochemical Analysis of Mcl–1 Protein in Human Tissues," *American Journal of Pathology* 146:1309–1319, (1995).

Kulmburg et al., "Immunoglobulin E Plus Antigen Challenge Induces a Novel Intercrine/Chemokine in Mouse Mast Cells," *J. Exp. Med.* 176:1773–1778 (1992).

Kuhn et al., "Specific Interaction of the Murine Transcription Termination Factor TTFI with Class–I RNA Polymerases," *Nature* 344:559–562 (1990).

Landsman et al., "Mouse Non–Histone Chromosomal Protein HMG–14 cDNA Sequence," *Nucleic Acids Research* 18:5311 (1990).

Landsman, et al., "Chromosomal Protein HMG–14. Complete Human cDNA Sequence and Evidence for a Multigene Family," *The Journal of Biological Chemistry* 261: 16082–16086 (1986).

Langst et al., "TTF–I Determines the Chromatin Architecture of the Active rDNA Promoter," *The EMBO Journal* 17:3135–3145 (1998).

Lee et al., "Impaired Wound Healing and Angiogenesis in eNOS–Deficient Mice," *Am. J. Physiol.* 277:H1600–H1608 (1999).

Lenarcic et al., "Human Cathepsin B and Cysteine Proteinase Inhibitors (CPIs) in Inflammatory and Metabolic Joint Diseases," *Bio. Chem. Hoppe–Seyler* 369:257–261 (1988).

Li and Cohen, "tsq101: A Novel Tumor Susceptibility Gene Isolated by Controlled Homozygous Functional Knockout of Allelic Loci in Mammalian Cells," *Cell* 85:319–329 (1996).

Li et al., "The TSG101 Tumor Susceptibility Gene is Located in Chromosome 11 Band p15 and is Mutated in Human Breast Cancer," *Cell* 88:143–154 (1997).

Mason et al., "Serine and Tyrosine Phosphorylations Cooperate in Raf–1, but not B–Raf Activation," *The EMBO Journal* 18:2137–2148 (1999).

Matoskova et al., "Constitutive Phosphorylation of eps8 in Tumor Cell Lines: Relevance to Malignant Transformation," *Molecular and Cellular Biology* 15:3805–3812 (1995).

McGuire, "Cloning and Characterization of the cDNA Encoding Mouse Dipeptidyl Peptidase I (Cathepsin C)," *Biochimica et Biophysica Acta* 1351:267–273 (1997).

Miki et al., "Development of a Highly Efficient Expression cDNA Cloning System: Application to Oncogene Isolation," *Proc. Natl. Acad. Sci. USA* 88:5167–5171 (1991).

Minty et al., "Molecular Cloning of the MCP–3 Chemokine Gene and Regulation of its Expression," *Eur. Cytokine Netw.*, 4:99–110, (1993).

Morris et al., "The Human Tyrosine Kinase Gene (FER) Maps to Chromosome 5 and is Deleted in Myeloid Leukemias with a del(5q)," *Cytogenet Cell Genet* 53:196–200 (1990).

Nakashima et al., "Molecular Cloning of a Human cDNA Encoding a Novel Protein, DAD1, Whose Defect Causes Apoptotic Cell Death in Hamster BHK21 Cells," *Molecular and Cellular Biology* 13:6367–6374 (1993).

Noguchi et al., "Developmental Expression of Sarcoglycan Gene Products in Cultured Myocytes," *Biochemical and Biophysical Research Communications,* 262:88–93 (1999).

O'Neill et al., "Tissue–Specific and Developmental Stage–Specific DNA Binding By a Mammalian SWI/SNF Complex Associated with Human Fetal–To–Adult Globin Gene Switching," *Proc. Natl. Acad. Sci. USA* 96:349–354 (1999).

Orlofsky et al., "Novel Expression Pattern of a New Member of the MIP–1 Family of Cytokine–Like Genes," *Cell Regulation* 2:403–412 (1991).

Paris et al., "Molecular Cloning and Sequence Analysis of Human Preprocathepsin C," *FEBS Letters* 369:326–330 (1995).

Pham et al., "Dipeptidyl Peptidase I is Required for the Processing and Activation of Granzymes A and B in vivo," *Proc. Natl. Acad. Sci. USA* 96:8627–8632 (1999).

Post et al., "Molecular Characterization of Two Murine Eosinophil β Chemokine Receptors," *The Journal of Immunology* 155:5299–5305 (1995).

Proost et al., "Human Monocyte Chemotactic Proteins–2 and –3:Structural and Functional Comparison with MCP–1," *J. Leukoc. Biol.* 59:67–74 (1996).

Rodriguez et al., "SUMO–1 Modification Activates the Transcriptional Response of p53," *The EMBO Journal* 18:6455–6461 (1999).

Rosato et al., "Involvement of the Tyrosine Kinase Fer in Cell Adhesion," *Molecular and Cellular Biology* 18:5762–5770 (1998).

Sager et al., "MASPIN:A Tumor Suppressing Serpin," Chemistry and Biology of Serpins, edited by Church et al., Plenum Press, New York, 1997.

Sanjay et al., "DAD1 is Required for the Function and the Structural Integrity of the Oligosaccharyltransferase Complex," *The Journal of Biological Chemistry* 273:26094–26099 (1998).

Sayah et al., "Downregulation of Apoptosis–Related Genes in Keloid Tissues," *Journal of Surgical Research* 87:209–216 (1999).

Schmid et al., "Nucleotide Sequence of the Murine Prothymosin α cDNA and its Deduced Primary and Secondary Protein Structure," *Biochimica et Biophysica Acta* 1088:442–444 (1991).

Seifert et al., "Nicotinamide Methylation:Tissue Distribution, Developmental and Neoplastic Changes," *Biochimica et Biophysica Acta* 801:259–264 (1984).

Shibanuma et al., "Isolation of a Gene Encoding a Putative Leucine Zipper Structure that is Induced by Transforming Growth Factor β1 and Other Growth Factors," *The Journal of Biological Chemistry* 267:10219–10224 (1992).

Shi et al., "Cystatin C Deficiency in Human Atherosclerosis and Aortic Aneurysms," *J. Clin. Invest.* 104:1191–1197 (1999).

Solem et al., "Transforming Growth Factor Beta Regulates Cystatin C in Serum–Free Mouse Embryo (SFME) Cells," *Biochemical and Biophysical Research Communications* 172:945–951 (1990).

Stephens et al., "95–Kilodalton B–Raf Serine/Threonine Kinase: Identification of the Protein and its Major Autophosphorylation Site," *Molecular and Cellular Biology* 12:3733–3742 (1992).

Sun et al., "Tumor Susceptibility Gene 101 Protein Represses Androgen Receptor Transactivation and Interacts with p300," *Cancer* 86:689–96 (1999).

Taha et al., "In Vivo Expression of Cytokine Receptor mRNA in Atopic Dermatitis," *J Allergy Clin Immunol* 102:245–50 (1998).

Takaki et al., "Molecular Cloning and Expression of the Murine Interleukin–5 Receptor," *The EMBO Journal* 9:4367–4374 (1990).

Tang et al., "Expression of Apoptosis Regulator in Cutaneous Malignant Melanoma," *Clinical Cancer Research* 4:1865–1871 (1998).

Tao, Lian et al., "Metabolic Regulation of Protein–Bound Glutamyl Phosphates: Insights into the Function of Prothymosin α," *Journal of Cellular Physiology* 178:154–163 (1999).

Taub et al., "Monocyte Chemotactic Protein–1 (MCP–1), –2, and –3 are Chemotactic for Human T Lymphocytes," *The Journal of Clinical Investigation,* Inc. 95: 1370–1376 (1995).

Tavernier et al., "Molecular Basis of the Membrane–Anchored and Two Soluble Isoforms of the Human Interleukin 5 Receptor α Subunit," *Proc. Natl. Acad. Sci. USA* 89:7041–7045 (1992).

Toomes et al., "Loss–of –Function Mutations in the Cathepsin C Gene Result in Periodontal Disease and Palmoplantar Keratosis," *Nature Genetics* 23:421–424 (1999).

Turk et al., "Structural and Functional Aspects of Papain–Like Cysteine Proteinases and their Protein Inhibitors," *Biol. Chem.* 378:141–150 (1997).

Tyrone, "Collagen–Embedded Platelet–Derived Growth Factor DNA Plasmid Promotes Wound Healing in a Dermal Ulcer Model," *Journal of Surgical Research* 93:230–236, (2000).

Van Coillie et al., "The Human MCP–2 Gene (SCYA8):Cloning, Sequence Analysis, Tissue Expression, and Assignment to the CC Chemokine Gene Contig on Chromosome 17q11.2," *Genomics* 40:323–331 (1997).

Van Ostade et al., "The Cell Surface Expression Level of the Human Interleukin–5 Receptor α Subunit Determines the Agonistic/Antagonistic Balance of the Human Interleukin–5 E13Q Mutein," *Eur. J. Biochem* 259:954–960 (1999).

Votta et al., "Ckβ–8 [CCL23], a Novel CC Chemokine, Is Chemotactic for Human Osteoclast Precursors and is Expressed in Bone Tissues," *The Journal of Cellular Physiology* 183:196–207 (2000).

Wang et al., "Expression of Monocyte Chemotactic Protein–3 mRNA in Rat Vascular Smooth Muscle Cells and in Carotid Artery After Balloon Angioplasty," *Biochimica et Biophysica Acta* 1500:41–48 (2000).

Wang et al., "Architectural DNA Binding by a High–Mobility–Group/Kinesin–Like Subunit in Mammalian SWI/SNF–Related Complexes," *Proc. Natl. Acad. Sci. USA* 95:492–498 (1998).

Weltman et al., "Interleukin–5: A Proeosinophil Cytokine Mediator of Inflammation in Asthma and a Target for Antisense Therapy," *Allergy and Asthma Proc.* 19:257–261 (1998).

Werner, "Keratinocyte Growth Factor: A Unique Player in Epithelial Repair Processes," *Cytokine and Growth Factor Reviews* 9:153–165 (1998).

Wolffe, et al., "Review: Chromatin Structural Features and Targets That Regulate Transcription," *Journal of Structural Biology* 129:102–122 (2000).

Wong, et al., "Evolutionary Conservation of the EPS8 Gene and its Mapping to Human Chromosome 12q23–q24," Oncogene 9:3057–3061 (1994).

Wu et al., "Sustained High–Level Production of Murine Chemokine C10 During Chronic Inflammation," *Cytokine* 11:523–530, (1999).

Xie et al., "Cell Cycle–Dependent Subcellular Localization of the TSG101 Protein and Mitotic and Nuclear Abnormalities Associated with TSG101 Deficiency," *Proc. Natl. Acad. Sci. USA* 95:1595–1600 (1998).

Yan et al., "Mouse Liver Nicotinamide N–Methyltransferase:cDNA Cloning, Expression, and Nucleotide Sequence Polymorphisms," *Biochemical Pharmacology* 54:1139–1149 (1997).

Yang et al., "Depletion of Eosinophil Infiltration by Anti–IL–5 Monoclonal Antibody (TRFK–5) Accelerates Open Skin Wound Epithelial Closure," *American Journal of Pathology* 151:813–819 (1997).

Yasugi et al., "Identification of the Structural and Functional Human Homolog of the Yeast Ubiquitin Conjugating Enzyme UBC9," *Nucleic Acids Research* 24:2005–2010 (1996).

Ying et al., "C–C Chemokines in Allergen–Induced Late–Phase Cutaneous Responses in Atopic Subjects: Association of Eotaxin with Early 6–Hour Eosinophils, and of Eotaxin–2 and Monocyte Chemoattractant Protein–4 with the Later 24–Hour Tissue Eosinophilia, and Relationship to Basophils and Other C–C Chemokines (Monocyte Chemoattractant Protein–3 and RANTES)," *The Journal of Immunology* 163:3976–3984 (1999).

Zhang et al., "Maspin Plays an Important Role in Mammary Gland Development," *Developmental Biology* 215:278–287, (1999).

Zhang et al, "Expression of Mapsin in Prostate Cells is Regulated by a Positive Ets Element and a Negative Hormonal Responsive Element Site Recognized by Androgen Receptor," *Proc. Natl. Acad. Sci. USA* 94:5673–5678 (1997).

Zou et al., "Maspin, a Serpin with Tumor–Suppressing Activity in Human Mammary Epithelial Cells," *Science* 263:526–529 (1994).

Gottlieb et al., "Response of Psoriasis to a Lymphocyte–Selective Toxin ($DAB_{389}IL-2$) Suggests a Primary Immune, but not Keratinocyte, Pathogenic Basis," *Nature Medicine* 1:442–447 (1995).

Nair et al., "Evidence for Two Psoriasis Susceptibility Loci (HLA and 17q) and Two Novel Candidate Regions (16q and 20p) by Genome–Wide Scan," *Human Molecular Genetics* 6:1349–1356 (1997).

Pittelkow, "Keratinocyte Abnormalities and Signaling Pathways," *In Roenigk* 225–246 (1998).

Saiag et al., "Psoriatic Fibroblasts Induce Hyperproliferation of Normal Keratinocytes in a Skin Equivalent Model in Vitro," *Science* 230:669–672 (1985).

Katz, A. B., et al., "A partial catalog of proteins secreted by epidermal keratinocytes in culture," *Journal of Investigative Dermatology* 112:818–821 (1999).

Figure 2

```
1    M A D G K A G D E K P E K S Q R A G A A G G P E E E A E K P    SW1136_human.
1    M A D G K A G E E K P E K P Q R A G A A G G P E E E A E K P    SW1136_murine 31   V K T K T V S S S N G G E S S S R S A E K R S A E E E A A D    SW1136_human.
31   V K T K T V S S S N G G E S S S R S A E K R S A E D E A A D    SW1136_murine 61   L P T K P T K I S K F G F A I G S Q T T K K A S A I S I K L    SW1136_human.
61   L P T K P T K M S K F G F A I G S Q T A R K A S A I S I R L    SW1136_murine 91   G S S K P K E T V P T L A P K T L S V A A A F N E D E D S E    SW1136_human.
91   G A S K P K E T V P T L A P K T L S V A A A F N E D E D S E    SW1136_murine 121  P E E M P P E A K M R M K N I G R D T P T S A G P N S F N K    SW1136_human.
121  P E E M P P E A K M R M K N I G R D T P T S A G P N S F N K    SW1136_murine 151  G K H G F S D N Q K L W E R N I K S H L G N V H D Q D N        SW1136_human.
151  G K H G F S D N Q K L W E R N I K S H L G N V H D Q D N        SW1136_murine Decoration 'Decoration #1': Box residues that differ from SW1136_human.pro.
```

Figure 3

```
1    M P R G S R S R T S R M A P P A S R A P Q M R A A P R P A P    SW1295_human.
1    M P R G S R S R T S R[V T]P P A S R A P Q M R A A P R[R]A P    SW1295_murine 31   V A Q P P A A A P P S A V G S S A A A P R Q P G L M A Q M A    SW1295_human.
31  [A]A Q P P A A A[A]P S A V G S[P]A A A P R Q P G L M A Q M A    SW1295_murine 61   T T A A G V A V G S A V G H T L G H A I T G G F S G G S N A    SW1295_human.
61   T T A A G V A V G S A V G H T L G H A I T G G F S G G[G S]A   SW1295_murine 91   E P A R P D I T Y Q E P Q G T Q P A Q Q Q Q[- -]P C L Y E I    SW1295_human.
91   E P A[K]P D I T Y Q E P Q G[A]Q[L Q N]Q Q[S F G]P C[S L]E I   SW1295_murine 119  K Q F L E C A Q N Q G D I K L C E G F N E V L K Q C R L A N    SW1295_human.
121  K Q F L E C A Q N Q[S]D[V]K L C E G F N E V L[R]Q C R[I]A N   SW1295_murine 149  G L A                                                          SW1295_human.
151  G L[M]                                                         SW1295_murine Decoration 'Decoration #1': Box residues that differ from SW1295_human.pro.
```

USE OF POLYPEPTIDES OR NUCLEIC ACIDS FOR THE DIAGNOSIS OR TREATMENT OF SKIN DISORDERS AND WOUND HEALING AND FOR THE IDENTIFICATION OF PHARMACOLOGICALLY ACTIVE SUBSTANCES

This application claims the benefit of U.S. Provisional Application No. 60/222,081, filed Aug. 1, 2000 and Foreign Application DE 10030149.5 filed Jun. 20, 2000.

The invention relates to the use of polypeptides selected from SEQ ID No. 1 to SEQ ID No. 26 and/or SEQ ID No. 29 to SEQ ID No. 48 and/or SEQ ID No. 55 to SEQ ID No. 58 and/or SEQ ID No. 63 to SEQ ID No. 73 and/or SEQ ID No. 80 to SEQ ID No. 82 and/or of a nucleic acids encoding these, and/or of a cell expressing said polypeptide or said nucleic acid, for the diagnosis, prevention and/or treatment of disorders, in particular skin disorders, wound healing, and/or wound healing disorders, and/or for the identification of pharmacologically active substances.

Wounds in general heal without therapeutic intervention. However, there are numerous disorders in which wound healing plays a role, such as, for example, diabetes mellitus, arterial occlusive diseases, psoriasis, Crohn's disease, epidermolysis bullosa, age-related skin changes or innervation disorders. Wound healing disorders lead to a delayed healing of wounds or to chronic wounds. These disorders can be caused by the nature of the wound (e.g. large-area wounds, deep and mechanically expanded operation wounds, burns, trauma, decubitus), medicinal treatment of the patients (e.g. with corticoids) but also by the nature of the disorder itself. For example, 25% of the patients with Type II diabetes thus frequently suffer from chronic ulcers ("diabetic foot"), of which approximately half necessitate expensive hospitalized treatments and nevertheless finally heal poorly. Diabetic foot causes more stays in hospital than any other complication associated with diabetes. The number of these cases in diabetes Type I and II is on the increase and represents 2.5% of all hospital admissions. Moreover, wounds heal more poorly with increasing age of the patients. An acceleration of the natural wound healing process is often desirable as well in order to decrease, for example, the danger of bacterial infections or the rest periods of the patients.

Further disorders can also occur after successful wound closure. While foetal skin wounds heal without scar formation, after injuries in the post-natal period formation of scars always occurs, which often represent a great cosmetic problem. In the case of patients with large-area burn wounds, the quality of life can moreover be dramatically adversely affected, especially as in scarred skin the appendages, such as hair follicles, sweat and sebaceous glands are missing. In the case of appropriate genetic disposition, keloids can also occur, hypertrophic scars which proliferate into the surrounding skin.

The process of skin healing requires complex actions and interactions of various cell types which proceed in a coordinated manner. In the wound healing process, the following steps are differentiated: blood clotting in the area of the wound, the recruitment of inflammatory cells, reepithelialization, the formation of granular tissue and matrix remodeling. Little is known up to now about the exact reaction pattern of the cell types involved during the phases of proliferation, migration, matrix synthesis and contraction, just like about the regulation of genes such as, for example, growth factors, receptors and matrix proteins.

Thus until now only a few satisfactory therapies have been developed in order to treat wound healing disorders. Established forms of therapy are restricted to physical assistance of wound healing (e.g. dressings, compresses, gels) or the transplantation of skin tissues, cultured skin cells and/or matrix proteins. In recent years, growth factors have been tested for improving wound healing without, however, improving the conventional therapy decisively. The diagnosis of wound healing disorders is also based on not very meaningful optical analyses of the skin, since a deeper understanding of the gene regulation during wound healing was lacking until now.

Not very satisfactory therapies have been developed until now for other disorders of regenerative processes as well. Here too, the knowledge of gene regulation is advantageous for the development of diagnostics and therapies. It has been shown (Finch et al., 1997, Am. J. Pathol. 151: 1619–28; Werner, 1998, Cytokine Growth Factor Rev. 9: 153–165) that genes relevant to wound healing also play a crucial role in dermatological disorders which are based on disorders of the regeneration of the skin, and generally in regenerative processes. Thus the growth factor KGF not only plays a crucial role in the regulation of the proliferation and differentiation of keratinocytes during wound healing, but is also an important factor in the hyperproliferation of the keratinocytes in psoriasis and regenerative processes in the intestine (in Crohn's disease and ulcerative colitis).

It is therefore the object of the present invention to make available polypeptides and nucleic acids encoding these which are involved in processes in disorders of skin cells, in wound healing and/or in wound healing disorders, and whose use decisively improves the diagnosis, prevention and/or treatment, and also the identification and development of pharmaceuticals which are effective in connection with these disorders.

Diseases of the skin, wound healing and its pathological disorders within the meaning of the invention are to be discriminated from skin diseases which are accompanied by uncontrolled cell proliferation and cell differentiation, in particular by skin cancer. In the latter disease, transformation of individual cells occurs, which therefore begin to proliferate in an uncontrolled, autonomous manner, i.e. isolated from interactions with other cell types, and at the same time transmit the pathological changes to the daughter cells. It is thus a disorder which is accompanied by a loss of interactions, for example of cell-cell adhesion and of typical cell properties. In contrast, diseases within the meaning of the invention are based on disorders of cell-cell interactions. The formation of skin diseases within the meaning of the invention is caused by a large number of factors. Thus in the case of psoriasis, for example, genetic predispositions and malfunctions of the T cells, fibroblasts and keratinocytes probably both play an important role (see, for example, Nair et al., 1997; Hum. Molec. Genet. 6: 1349–1356; Gottlieb et al., 1995, Nat. Med. 1: 442–447; Saiag et al., 1985, Science, 230: 669–672; Pittelkow, 1998, in Roenigk 1998: 225–246). The course of wound healing can also be modulated by various endogenous and exogenous factors. Even small perturbations of the interactions between the different cell types of the dermis and epidermis themselves, but also of interactions with other tissues and organs such as the blood vessel system, the nervous system and the connective tissue, can lead to disturbed wound healing followed by scar formation. Furthermore, infections, aging, disorders such as diabetes and immune disorders and also vitamin deficiencies can adversely affect the wound-healing process. Similarly complex interactions are also described for other skin diseases such as vitiligo and atopic dermatitis. This essentially differentiates the skin diseases from cancer of these organs.

Preferred examples of skin diseases encompass psoriasis, eczema, especially atopic eczema and disorders of pigmentation of the skin, especially vitiligo. Examples of disorders of wound healing are wounds of patients suffering from diabetes or alcoholism, wounds infected with microorganisms, ischemic wounds and wounds of patients with impaired circulation or venous stasis. Especially preferred examples of badly healing wounds are diabetic, neuropathic, venous and arterial ulcers, especially diabetic ulcers.

The autonomous character of carcinomatous disorders is also seen at the therapeutic level. In the case of non-metastasizing tumors, cancer can be treated surgically. This physical treatment is possible, as no interactions take place between tumor cells and the surrounding cells and tissues, so that the patient can be cured by simple excision of the tumor, whereas this is not possible in the case of skin diseases within the meaning of the invention—the pathological disorders of the cell-cell and/or tissue-tissue interactions cannot be abolished by excision of affected skin sites. The fact that the diseases compared are diseases which are based on a fundamentally different mechanism becomes clear if the therapeutic approaches are compared. In cancer disorders and diseases which are accompanied by uncontrolled cell proliferation, therapy is directed at the destruction of rapidly growing cells, e.g. by means of cytostatics. These toxic substances prevent the growth of actively proliferating cells while cells in the G0 phase of the cell cycle are not affected. In contrast, the treatment of disorders of skin cells within the meaning of the invention aims at the modulation of the interactions between the different cell types, for example by affecting the migration, proliferation and differentiation of individual cell types. Skin diseases within the meaning of the invention cannot be cured by general inactivation of proliferating cells. The methodological approach to the identification of the nucleic acids used according to the invention, which are involved in wound healing and/or in processes of the skin diseases within the meaning of the invention, differs clearly from procedures which are suitable for identifying nucleic acids which are involved in processes of the carcinomatous disorders. The latter can be identified by analysis of genes of the cell type affected by cancer which are expressed in differential form. The aim of the assay of the present invention is, however, rather to identify, by comparison of the expression in diseased and healthy tissue biopsies, genes which are involved in the complex processes of the skin diseases and/or in wound healing and/or its pathological disorders. This procedure would be unsuitable for the identification of genes relevant to cancer.

In the analysis of gene expression during the wound healing process it was surprisingly possible to identify genes, that until now were not connected with diagnosis, prevention and/or treatment of disorders, of wound healing and/or of disorders of wound healing, and for the identification of pharmacologically active substances but whose regulation is essential for the healing process and which are thus in a causal relationship with diagnosis, prevention and/or treatment of disorders, disorders of the skin, in wound healing and/or disorders of wound healing, and for the identification of pharmacologically active substances. The polypeptides of these genes do not belong to the targets known until now for diagnosis—such as, for example, the indication—and/or the treatment—such as, for example, the modulation—of disorders or wound healing, of disorders of wound healing or for the identification of pharmacologically active substances, such that completely novel therapeutic approaches result from this invention.

The object is therefore achieved according to the invention by the use of one or more polypeptides selected from a sequence of SEQ ID No. 55 to SEQ ID No. 58 or functional variants thereof and/or of a nucleic acid or a variant thereof encoding these, and/or of a cell expressing said polypeptide or a functional variant thereof or said nucleic acid or a variant thereof, if appropriate combined or together with suitable additives and/or auxiliaries, for the diagnosis, treatment and/or prevention of diseases, in particular diseases of skin cells, of wound healing and/or its pathological disorders, and/or its use for the identification of pharmacologically active substances.

The exact biological functions of the polypeptides selected from a sequence of SEQ ID No. 55 to SEQ ID No. 58 used according to the invention are unknown. In the investigations in the context of this invention, it was possible for the first time to determine a relationship of the polypeptides according to the invention with disorders, for example skin diseases. The accession numbers of the polypeptide sequences according to the invention and their cDNAs, if known, are listed in Table 3. The cDNA sequences of the polypeptides of SEQ ID No. 55 to 57 are listed under SEQ ID No. 50 to 52. FIG. 2 and FIG. 3 show the comparison of human and murine polypeptide sequences.

In the analysis of gene expression during the wound-healing process, it was possible to identify further genes whose already known and described functions have previously not been connected with skin diseases or wound healing, for example with disturbed wound healing, but whose regulation is essential for the wound-healing process and which have thus been brought for the first time into causal relationship with skin diseases, for example with disturbed wound healing. The polypeptides of these genes do not belong to the previously known targets of skin disease therapies and/or wound healing or its disorders, so that completely new therapeutic approaches result from this invention.

The object of the invention is furthermore achieved by the use of at least one polypeptide selected from a sequence of SEQ ID No. 1 to SEQ ID No. 20 and/or SEQ ID No. 31 to SEQ ID No. 48 and/or SEQ ID No. 63 to SEQ ID No. 70 and/or SEQ ID No. 80 to SEQ ID No. 82 or functional variants thereof and/or nucleic acids or variants encoding these, and/or of a cell expressing said polypeptide or a functional variant thereof or said nucleic acid or variants thereof, if appropriate combined or together with suitable additives and/or auxiliaries, for the diagnosis, prevention and/or treatment of diseases of skin cells, of wound healing and/or its pathological disorders, and/or its use for the identification of pharmacologically active substances.

The following polypeptides can be used according to the invention:

The tumor susceptibility gene TSG 101 from mouse (SEQ ID No. 1) or human (SEQ ID No. 2) that is known from WO 97/18333 and U.S. Pat. No. 5,892,016 (Li and Cohen, 1996, Cell 85:319–329; Li et al., 1997, Cell 88:143–154). The functional inactivation of TSG 101 in fibroblasts leads to cellular transformation and to the ability to form metastasizing tumors. TSG 101-deficient neo-plastic cells show abnormalities in mitosis associated processes (Xie et al., 1998, Proc. Natl. Acad. Sci. U.S.A. 95:1595–1600). Furthermore, a role as transcriptional modulator is assumed (Sun et al., 1999, Cancer 86:689–696). In addition to the human polypeptide according to SEQ ID No. 2, the splice variant according to SEQ ID No. 82 (SWISSProt: Q99816) can also be used.

The tumor suppressor protein MASPIN, that is known from U.S. Pat. No. 5,905,023, U.S. Pat. No. 5,801,001, U.S. Pat. No. 5,470,970 and WO 94/05804 from mouse (SEQ ID No. 3) or human (SEQ ID No. 4) (Zou et al., 1994, Science, 263, 526–529). MASPIN is a serine protease inhibitor (Zhang et al., 1997, Mol. Med. 3:49–59) that is expressed in normal breast and prostate epithelial cells (Zhang et al., 1997, Proc. Natl. Acad. Sci. U.S.A. 94:5673–5678) and plays an essential role in the development of the breast gland (Zhang et al., 1999, Dev. Biol. 215:278–287).

The RNA-polymerase I termination factor TTF-I from mouse (SEQ ID No. 5) or human (SEQ ID No. 6) (Evers and Grummt, 1995, Proc. Natl. Acad. Sci. U.S.A. 92:5827–5831). The protein mediates the termination of transcription of ribosomal genes (Kuhn et al., 1990, Nature 344:559–62) as well as the transcriptional activation of ribosomal genes in chromatin (Langst et al., 1998, EMBO J. 17:3135–45).

The protooncogen B-raf from mouse (SEQ ID No. 7) or human (SEQ ID No. 8), that is known from WO 91/02077 and U.S. Pat. No. 7,745,381 (Miki et al., 1991, Proc. Natl. Acad. Sci. U.S.A. 88:5167–5171; Stephens et al., 1992, Mol. Cell. Biol. 12:3733–3742). The B-raf protooncogene belongs to the Raf-family comprising serine/threonine protein kinases that link the stimulation of growth factor receptors and the activation of mitogen-activated protein kinases (Mason et al., 1999, EMBO J. 18:2137–48). Furthermore, B-Raf can inhibit apoptosis (Erhardt et al., 1999, Mol. Cell. Biol. 19:5308–15).

Prothymosin alpha from mouse (SEQ ID No. 9) or human (SEQ ID No. 10), that is known from U.S. Pat. Nos. 4,716,148 and 4,659,694 (Schmidt and Werner, 1991, Biochim. Biophys. Acta. 1088:442–444; Eschenfeldt and Berger, 1986, Proc. Natl. Acad. Sci. U.S.A. 83:9403–9407). It codes for a small acidic nuclear protein that has a role in the proliferation of cells (Tao et al., 1999, J. Cell Physiol. 178:154–63).

The GOGLI 4-TRANSMEMBRANE SPANNING TRANSPORTER or MTP (mouse transporter protein) from mouse (SEQ ID No. 11) or human (SEQ ID No. 12) (Hogue et al., 1996, J. Biol. Chem. 271:9801–9808; Nagase et al., 1995, DNA Res. 2:37–43). It is a strongly conserved membrane protein, that is localized in lysosomes and endosomes of mammalian cells. The protein is responsible for the subcellular distribution of a number of different small hydrophobic molecules and contributes to the sensitivity respectively resistance of mammalian cells towards particular active substances (Hogue et al., 1999, J. Biol. Chem. 274:12877–82). For the mouse homologue, an alternative polypeptide truncated at the C terminus by 89 amino acids is formed by an alternative translation initiation site (see SwissProt: Q60961). This murine polypeptide can also be used according to the invention.

CCR-1 from mouse (SEQ ID No. 13) or human (SEQ ID No. 14) (Post et al., 1995, J. Immunol. 155:5299–5305) that is an eosinophilic receptor for the CC-chemokin eotaxin (Gao et al., 1996, Biochem. Biophys. Res. Comm. 223:679 –84). CCR-1 is expressed in heart, spleen and lung (Gao and Murphy, 1995, Genomics 29:294–96).

The nucleosome binding protein HMG-14 from mouse (SEQ ID No. 15) or human (SEQ ID No. 16) (Landsman and Bustin, 1990, Nucleic Acids Res. 18:5311; Landsman et al., 1986, J. Biol. Chem. 261:16082–16086), that opens up higher order chromatin structures and thus increases the transcription and replication potential of chromatin (Herrera et al., 1999, Mol. Cell. Biol. 19:3466–73).

Split hand/foot deleted 1 from mouse (SEQ ID No. 17) or human (SEQ ID No. 18), that is a candidate gene for the autosomal dominant form of "split hand/split foot malformation disorder" that is expressed in limb buds, in the "cranofacial primordia" and in the skin (Crackower et al., 1996, Hum. Mol. Genet. 5:571–9).

The orphan receptor TAK1 or TR4 from mouse (SEQ ID No. 19) or human (SEQ ID No. 20) (Hirose et al., 1995, Gene 163:239–242; Hirose et al., 1994, Mol. Endocrinol. 8:1667–1680), that belongs to the superfamily of nuclear hormone receptors (Hirose et al., 1994, Mol, Endocrinol. 8:1667–80). As a homodimer, TR4 influences the multitude of signal transduction pathways, among them retinoic acids, thyroid hormone, vitamin D3 and "ciliary neutrophic factor". Additionally TR4 forms heterodimers with the androgen receptor (Lee et al., 1999, Proc. Natl. Acad. Sci. U.S.A. 96:14724–9).

BAF57 from mouse (SEQ ID No. 31) or human (SEQ ID No. 32), that is known from WO 95/14772, which is a part of the chromatin remodeling SWI/SNF complex of higher eukaryotes (Wang et al., 1998, Proc. Natl. Acad. Sci. U.S.A. 95:492–498.) The SWI/SNF complexes regulate the transcription of specific genes by relieving chromatin mediated repression of transcription (Wolffe and Guschin, 2000, J. Struct. Biol. 129:102–122). Additionally, a role has been shown for the switch from expression of fetal to adult globin in mice (Armstrong et al., 1999, Proc. Natl. Acad. Sci. U.S.A. 96:349–54). In addition to the known human and mouse polypeptides, the closely related novel human polypeptide having a significantly different sequence (SEQ ID No. 80) can also be used. The cDNA encoding the polypeptide according to SEQ ID No. 80 is indicated under SEQ ID No. 83.

Epidermal growth factor receptor kinase substrate EPS 8 from mouse (SEQ ID No. 33) or human (SEQ ID No. 34), that is known from U.S. Pat. No. 7,935,311, which amplifies the EGF dependent mitogenic signales (Wong et al., 1994, Oncogene 9:3057–3061; Fazioli et al., 1993, EMBO J. 12:3799–3808). Both over-expression as well as constitutive phosphorylation of EPS 8 has been described in connection with tumor development (Matoskova et al., 1995, Mol. Cell Biol. 15:3805–3812).

KIAA1247 from human (SEQ ID No. 36), that according to WO 99/34004 can be applied as a marker protein for cancer metastasis. Additionally, a KIAA1247 homologue from rat is known as protein from WO 98/53071, whose expression is induced in injured or regenerating tissue, in particular from kidney tissue of the rat. In addition to the known polypeptide from human, the polypeptide from mouse (SEQ ID No. 35) that is mentioned for the first time in this work can also be used. In addition two human splice variants of the gene encoding the polypeptide of SEQ ID No. 36, which are mentioned for the first time in this work, can be used according to the invention. These splice variants encode shorter variants of SEQ ID No. 36: the amino acids 652 to 654 and 664 to 681 or the amino acids 664 to 681 of the polypeptide of SEQ ID No. 36, respectively, are deleted in these variants. In addition, other KIAA1247 polypeptides can be used according to the invention, which result from alternative translation initiation ATG-codon. Examples of such variants are disclosed in WO 00/73454 and in WO 00/58473.

Phospholipase inhibitor GIPL from human (SEQ ID No. 38), that is known from U.S. Pat. Nos. 5,948,626, 5,663,059 and 5,811,520. In addition to the already known polypeptide from human the polypeptide from mouse (SEQ ID No. 37), that is mentioned in this work for the first time, and the closely related polypeptides with a significantly divergent sequence (SEQ ID No. 45 and SEQ ID No. 81), which are mentioned in this work for the first time, can be used. The cDNA encoding the polypeptide according to SEQ ID No. 81 is indicated under SEQ ID No. 84.

EAT/MCL-1 from mouse (SEQ ID No. 39) or human (SEQ ID No. 40), that is known from WO 95/28497, which is expressed in numerous tissues (Krajewski et al., 1995, Am. J. Pathol. 146:1309–19) and that plays role in cutaneous malignant melanoma (Tang et al., 1998, Clin. Cancer Res. 4:1865–71).

TSC-22 (TGF-beta-stimulated clone 22 gene) from human (SEQ ID No. 42) and mouse (SEQ ID No. 41) (Jay et al., 1996, Biochem. Biophys. Res. Commun. 222:821–826; Shibanuma et al., 1992, J. Biol. Chem. 267:10219–10224), that belongs to the "leucine-zipper" family of transcription factors (Kester et al., 1999, J. Biol. Chem. 274:27439–47). Transcription of TSC-22 is induced by variety of stimuli as, for instance, growth inhibitors (Kester et al., 1999, J. Biol. Chem. 274:27439–47). Additionally an increased expression of TSC-22 during development of the mouse embryo was observed at locations where mesenchymal-epithelial interaction occurs (Dohrmann et al., 1999, Mech. Dev. 84:147–51).

Gamma-sarcoglycan from human (SEQ ID No. 44) or mouse (SEQ ID No. 43) (Noguchi et al., 1995, Science 270:819–822; Noguchi et al., 1999, Biochem. Biophy. Res. Commun. 262:88–93), that is known from JP 100 57 065 and U.S. Pat. No. 5,837,537. Gamma-sarcoglycan is a component of the sarcoglycan complex that again is a subcomplex of the dystrophin gycoprotein complex. This establishes a connection between the extracellular matrix and the actin cytoskeleton (Hack et al., 2000, Microsc. Res. Tech. 48:167–80). Mutation of gamma-sarcoglycan has been described as a primary genetic defect of a muscular dystrophy (SCARMD) (Noguchi et al., 1995, Science 270:819–822).

Cysteine proteinase inhibitor cystatin C from human (SEQ ID No. 47) or mouse (SEQ ID No. 46) (Abrahamson et al., 1987, FEBS Lett. 216:229–233; Solem et al., 1990, Biochem. Biophys. Res. Commun. 172:945–951), that is known from WO 99/38882, WO 88/09384, DE 372 4 581, JP 012 02 287, JP 010 74 988 and U.S. Pat. No. 5,212,297. Cystein protease inhibitors play a role in inflammatory disorders as, for example, rheumatism (Lenarcic et al., 1988, Biol. Chem. Hoppe Seyler 369 (Suppl.):257–261) and in vascular disorders (Shi et al., 1999, J. Clin. Invest. 104:1191–1197). In addition to the known polypeptide variant from mouse (SEQ ID No. 46) (Solem et al., 1990, Biochem. Biophys. Res. Commun. 172:945–951) the closely related polypeptide with a divergent sequence, that has been described in this work for the first time (SEQ ID No. 48) can also be used.

The tyrosine kinase Fer from mouse (SEQ ID No. 63) or human (SEQ ID No. 64) (SwissProt: P70451; Hao et al., 1989, Mol. Cell. Biol. 9:1587–1593), that is both localized in the nucleus as well as in the cytoplasm (Hao et al., 1991, Mol. Cell. Biol. 11:1180–1183). A role for Fer has been postulated both for cell-cell-adhesion (Rosato et al., 1998, Mol. Cell. Biol. 18:5762–5770) as well as a role as proto-oncogen (Morris et al., 1990, Cytogenet. Cell. Genet. 53:196–200).

The C-C cytokine MRP-3 (macrophage inflammatory protein 3) from mouse (SEQ ID No. 65) or human (SEQ ID No. 66), that is known from WO 99/28473, WO 96/34891 and WO 98/14582, that is also called C10, MPIF-1 (Myeloid Progenitor Inhibitory Factor-1), CK-beta-8 or small inducible cytokine A23 (Orlosfsky et al., 1991, Cell Regul. 2:403–412; Li and Ruben, 1996, U.S. Pat. No. 5,504,003). A high expression of MRP-3 a macrophages has been observed in chronic infection of the peritoneum (Wu et al., 1999, Cytokine 11:523–30). As a typical C-C cytokine MRP-3 is a chemoattractant for leukocytes (Haelens et al., 1996, Immunobiology 195:499–521) but it also effects osteoclasts (Votta et al., 2000, J. Cell Physiol. 183:196–207). In addition it has been observed that MRP-3 mRNA is not significantly upregulated by stimuli, that are connected to wound healing (Orlofsky et al., Cell Regul., 1991, 2:403–412).

The nicotinamide N-methyltransferase NNMT from mouse (SEQ ID No. 67) or human (SEQ ID No. 68) (Aksoy et al., 1994, J. Biol. Chem. 269:14835–14840; Yan et al., 1997, Biochem. Pharmacol. 54:1139–1149), that catalyzes the methyltransfer of S-adenosylmethionine to nicotineamide. There are several pieces of evidence, that NNMT can regulate the growth of liver cells (Seifert et al., 1984, Biochim, Biophys. Acta 801:259–64). In addition a role of the enzyme in liver cancer has been proposed (Hoshino et al., Biochim. Biophys. Acta 719:518–526).

The ubiquitin protein ligase UBC9 from mouse (SEQ ID No. 69) or human (SEQ ID No. 70) (Yasugi and Howley; 1996, Nucleic Acids Res. 24:2005–2010; SwissProt: P50550), that is an important component of the proteasome mediated protein degradation (Hershko and Ciechanover, 1998, Annu. Rev. Biochem. 67:425–479). The ubiquitin dependent protein degradation plays a role in most divergent processes like cell cycle control, signal transduction or immune response. There are indications that UBC9 plays a role in accelerated aging (Kawabe et al., 2000, J. Biol. Chem.). In addition UBC9 catalyzes the sumoylation of p53 and thus activates its function as transcription factor (Rodriguez et al., 1999, EMBO J. 18:6455–61).

For none of these polypeptides, nucleic acids coding for them or the described cDNA a connection with skin disorders or wound healing or its disorders has been described or suggested. Therefore, it was unexpected that this compounds could be used according to the present invention. The accession numbers of the polypeptides according to the invention and the cDNAs are indicated in Table 4. The cDNA sequences of the polypeptides in SEQ ID No. 31, SEQ ID No. 35 and SEQ ID No. 37, SEQ ID No. 80 and SEQ ID No. 81, are indicated in SEQ ID No. 53 and SEQ ID No. 54 and SEQ ID No. 83 and SEQ ID No. 84.

During the analysis of gene expression during the wound healing processes it was possible to identify additional genes whose already known and described functions until now were not connected with wound healing, but whose regulation is essential for the wound healing process and which are thus brought for the first time in a causal relationship with wound healing. The polypeptides of these genes do not belong to the targets known until now for therapy in connection with pathological change of wound healing, such that completely novel therapeutic approaches result from this invention.

The object of the invention is therefore additionally achieved by the use of at least one polypeptide selected from a sequence of SEQ ID No. 21 to SEQ ID No. 26 and/or SEQ ID No. 29 to SEQ ID No. 30 and/or SEQ ID No. 71 to SEQ ID No. 73 or functional variants thereof and/or nucleic acids or variants thereof encoding these, and/or of a cell expressing said polypeptide or a functional variant thereof or said nucleic acid or variants thereof, if appropriate combined or together with suitable additives and/or auxiliaries, for the diagnosis, prevention and/or treatment in wound healing and/or its pathological disorders, or for the identification of pharmacologically active substances.

The following polypeptides can be used according to the invention.

The monocyte chemotactic protein-3, MCP-3 from mouse (SEQ ID No. 21) or human (SEQ ID No. 22) (Kulmburg et al., 1992, J. Exp. Med. 176:1773–1778; Minty et al., 1993, Eur. Cytokine Netw. 4:99–110), that is known from WO 95/04158, WO 99/12968 and EP 0 488 900. MCP-3 is a CC-chemokine that serves the chemoattraction and activation of monocytes, T-lymphocytes, eosinophiles and basophilic granulocytes, natural killer cells and dendritic cells. The activation of the target cells is effected through the chemokine receptors CCR2 and CCR3 (Wang et al., 2000 Biochim. Biophys. Acta 1500:41–8). MCP-3 plays a role in allergic reactions of the skin (Ying et al., 1999, J. Immunol. 163:3976–84.

The alpha-chain of the heterodimeric Interleukin-5 receptor of mouse (SEQ ID No. 23) or human (SEQ ID No. 24) (Takaki 1990, EMBO J. 9:4367–4374; Tavernier et al., 1992, Proc. Natl. Acad. Sci. U.S.A. 89:7041–7045), that is known from EP 0 475 746 and WO 98/47923. It mediates the specific binding of the ligand Interleukin-5 (Van Ostade et al., 1999, Eur. J. Biochem. 259:954–60) and is expressed on the cell membrane of eosinophiles (Weltman & Karim, 1998, Allergy Asthma Proc. 19:257–61). A role of the Interleukin-5 receptors has been described for Atopic Dermatitis (Taha et al., 1998, J. Allergy Clin. Immunol. 102:245–50) Interleukin-5 plays an essential role in the differentiation, proliferation and functional activation of eosinophiles (Iwama et al., 1999, Mol. Cel. Biol. 19:3940–50) and in contrast to the receptor, that is described here, a function in wound healing has been described for Interleukin-5 (Yang et al., 1997, Am. J. Pathol. 151:813–9).

The integral membrane protein Dad1 from mouse (SEQ ID No. 25) or human (SEQ ID No. 26) (Nakashima et al., 1993, Mol. Cell. Biol. 13:6367–6374; Apte et al., 1995, FEBS Lett. 363:304–306). It is a component of the oligosaccharyltransferase enzyme complexes, that initiates the N-glycosylation (Sanjay et al., 1998, J. Biol. Chem. 273:26094–9). Dad1 plays a role in inhibition of apoptosis in particular cell types (Hong et al., 1999, J. Immunol. 163:1888–93) and in keloids (Sayah et al., 1999, J. Surg. Res. 87:209–16).

MCP-2 (C-C chemokine monocyte chemotactic protein 2) from human (SEQ ID No. 30) or mouse (SEQ ID No. 29) (van Coillie et al., 1997, Genomics 40:323–331; EMBL: AB023418) that is known from EP 0 905 240, EP 0 905 241, WO 98/02459, EP 0 906 954, WO 95/04158, WO 99/12968 and WO 97/25427. MCP-2 belongs to the C-C chemokines and acts as a chemoatractant for different cells like macrophages, basophiles and eosinophiles (Taub et al., 1995, J. Clin. Invest. 95:1370–6; Proost et al., 1996, J. Leukoc. Biol. 59:67–74). MCP-2 is a signal molecule that stimulates the directed migration of T-cells and monocytes in processes of inflammation and recruits them (Taub et al., 1995, J. Clin. Invest. 95:1370–6). In addition to the known polypeptide variants of human (SEQ ID No. 31) (Van Coillie et al., 1997 Genomics 40:323–331) the closely related polypeptide with a divergent sequence (SEQ ID No. 71), that is described in this work for the first time, can also be used.

The cysteine protease cathepsin C from mouse (SEQ ID No. 72) or human (SEQ ID No. 73) (Paris et al., 1995, FEBS Lett. 369:326–330; McGuire et al., 1997, Biochim. Biophys. Acta 1351:267–273), that is known from WO 96/33278, which is present in the lysosomes of different cells (Turk et al., 1997, Biol. Chem. 378:141–150). Cathepsin C plays an important role in the activation of granzym A and B and, thus, in induction of apoptosis through cytotoxic lymphocytes (Pham and Ley, 1999, Proc. Natl. Acad. Sci. U.S.A. 96:8627–8632). In addition it was observed that a "loss-of-function" mutation in the cathepsin C gene leads to palmoplanar keratosis and periodontitis (Hart et al., 1999, J. Med. Genet. 36:881–887; Toomes et al., 1999, Nat. Genet. 23:421–424).

For none of the polypeptides or nucleic acids coding for them a connection with wound healing was described or suggested until now. It was, therefore, unexpected that these polypeptides can be used according to the present invention. The accession numbers of the polypeptides according to the present invention and their cDNAs are indicated in Table 5.

Generally, the analysis of differentially expressed genes in tissues is affected by markedly more errors in the form of false-positive clones than the analysis of cell culture systems. This problem cannot be circumvented by the use of a defined cell culture system, as existing, simple cell culture systems cannot adequately simulate the complexity of the wound-healing process in the tissue.

The problem exists in particular in the skin, which consists of a multiplicity of different cell types. Moreover, the process of wound healing is a highly complicated process which includes temporal and spatial changes of cellular processes, such as proliferation and differentiation, in the different cell types. The approach to investigate not only the complex cell system skin, but moreover the physiological process of wound healing and even different wound-healing stages at the level of differentially expressed genes is therefore not a promising strategy for a person skilled in the art. On account of these difficulties, the success of the screening was significantly dependent on the choice of the experimental parameters. While the methods used (e.g. subtractive hybridization) are standard methods, the screening and verification strategy is already inventive per se owing to the thought-out and defined choice of parameters. For example, the time of biopsy taking is critical for the success of the screening: wound-healing disorders and skin diseases are often based on disorders in cell proliferation and cell migration. These processes are initiated one day after wounding, which is why analysis of the molecular processes before this time would yield little information about the processes which are essential for normally proceeding wound healing. On the other hand, in the course of wound healing, the composition of the cell types in the wound changes greatly later than one day after wounding. This can lead to a differential expression of a specific gene in the wound being measured which is based not on altered expression in the cells, but only on the different cell composition. This illustrates that the choice of the day of biopsy taking crucially affected the success of the screening. Despite the defined parameters, an overrepresentation of genes was observed, which are differentially expressed during wound healing, but which are unsuitable for use in wound healing or in skin diseases. These genes include, for example, genes which code for enzymes of the primary metabolism, such as glycolysis, citrate cycle, gluconeogenesis and respiratory chain, but also genes which code for ribosomal proteins, e.g. L41 and S20. Only a comparatively small number of genes were identified as suitable. An identification of the genes useable according to the invention as genes relevant to wound healing was therefore surprising.

Moreover, there are enormous variabilities in the state of the wound at the time of a possible biopsy of the patient on initial contact with the physician. An animal model was therefore used for the identification of the previously described nucleic acids. BALB/c mice were wounded and wound biopsies were taken at different times. This procedure has the advantage that conditions such as genetic background, nature of the wound, time of the biopsy etc. can be exactly controlled and so only allow a reproducible analysis of gene expression. Even under the defined mouse conditions, further methodical problems arise such as redundancy of the analyzed clones and underrepresentation of weakly expressed genes, which make the identification of relevant genes difficult.

The nucleic acids of the polypeptides useable according to the invention were isolated from cDNA libraries which prepared from intact and wounded skin. The cDNAs selected here were those which have different frequency rates in well-healing wounds in comparison to poorly healing wounds (examples 1 and 3). This was carried out, for example, with the aid of subtractive hybridization (Diatchenko et al., 1996, Proc. Natl. Acad. Sci. USA 93: 6025–30) and/or using the comparative counting of clones in cDNA libraries by means of analysis of restriction fragment patterns (Halle et al., 1999, EP 0965642A1) and/or with the aid of "differential display RT-PCR" (Liang et al., 1992, Cancer Res. 52: 6996–6998; Liang and Pardee, 1992, Science 257: 967–971; Prashar and Weissman, 1996, Proc. Natl. Acad. Sci. USA 93: 659–663). The cDNAs thus selected originate from genes which are either more strongly or more weakly expressed in wound healing disorders than in wound healing which proceeds normally.

After the primary identification of a gene, it is necessary to confirm wound healing-specific expression by a further method. This was carried out with the aid of "reverse Northern blots" and "TaqMan analysis". Using these methods, the amount of mRNA in tissues from various wound-healing states and in skin diseases (psoriasis) was determined or skin disease-specific local alterations in the expression pattern were detected in biopsies (Examples 2, 4 to 7).

In the present analysis of gene expression during the wound-healing process, besides genes whose function was completely unknown until now, genes were also identified which had previously not been linked to wound-healing disorders. Novel variants of known genes were furthermore identified having sequences which differed significantly from the previously published and/or patented sequences.

Of the part of the identified genes previously not connected with wound-healing disorders, it was hitherto known that they have a function in proliferation (Tsg101: Xie et al., Proc. Natl. Acad. Sci. USA 95: 1595–1600; MASPIN: Sager et al., 1997, Adv. Exp. Med. Biol. 425:77–88; B-Raf: Mason et al., 1999, EMBO J. 18:2137–48; Ikawa et al., 1988, Mol. Cell Biol. 8:2651–2654; Prothymosin alpha: Tao et al., 1999, J. Cell Physiol. 178:154–163; Eps8: Wong et al., 1994, Oncogene 9:3057–3061; KIAA1247: WO 99/34004; EAT/MCL-1: Tang et al., 1998, Clin. Cancer Res. 4:1865–1871; TSC-22: Kester et al., 1999, J. Biol. Chem. 274:27439–47; Fer: Morris et al., 1990, Cytogenet. Cell. Genet. 53:196–200), differentiation (MASPIN: Zhang et al., 1999, Dev. Biol. 215:278–87; Split hand/foot deleted 1: Crackower et al., 1996, Hum. Mol. Genet. 5:571–9), cell migration (MRP-3: Haelens et al., 1996, Immunobiology 195:499–521; MCP-3: Taub et al., 1995, J. Clin. Invest. 95:1370–6; MCP-2: Taub et al., 1995, J. Clin. Invest. 95:1370–6) and/or apoptosis (B-Raf: Erhardt et al., 1999, Mol. Cell. Biol. 19:530815). These genes, however, were previously not linked to wound healing.

In addition to the known polypeptides of human phospholipase inhibitor GIPL (U.S. Pat. No. 5,948,626), MCP-2 (van Coillie et al., 1997, Genomics 40: 323–331), BAF57 (WO 95/14772) and mouse cystatin C (Solem et al., 1990, Biochem. Biophys. Res. Commun. 172:945–951), closely related polypeptides having a significantly different sequence were identified. Of the known polypeptides of human phospholipase GIPL (U.S. Pat. No. 5,948,626) and human KIAA1247 (WO 99/34004), the sequences of the corresponding mouse polypeptide were identified for the first time.

The polypeptides of these genes do not include the previously known targets of therapies of wound-healing disorders, so that completely new therapeutic approaches result from this invention. Of the remaining identified genes, no description of function yet exists (Table 3).

For the checking or generation of full-length cDNA sequences of the previously described nucleic acids, full-length clones were generated with the aid of colony hybridization (Sambrook et al., 1989, Molecular Cloning: A Laboratory Manual, Cold Spring Harbor, Cold Spring Harbor Laboratory Press, New York, chapter 8–10) and/or PCR-based methods ("RACE", Frohman et al., 1988, Proc. Natl. Acad. Sci. USA 85: 8998–9002, Chenchik et al., 1996, in A Laboratory Guide to RNA: Isolation, Analysis, and Synthesis, Ed. Krieg, Wiley-Liss, pages 272–321; "LDPCR", Barnes, 1994, Proc. Natl. Acad. Sci. USA 91: 2216–20) both for the mouse genes and also for the human genes and the sequence of these clones was determined.

The term "functional variants" of a polypeptide within the meaning of the present invention includes polypeptides which are regulated, for example, like the polypeptides used according to the invention during disease, in particular skin diseases, or in regenerative processes of the skin, but in particular in wound-healing disorders. Functional variants, for example, also include polypeptides which are encoded by a nucleic acid which is isolated from non-skin-specific tissue, e.g. embryonic tissue, but after expression in a cell involved in wound healing or skin disease have the designated functions.

Functional variants within the meaning of the present invention are also polypeptides which have a sequence homology, in particular a sequence identity, of about 70%, preferably about 80%, in particular about 90%, especially about 95%, with the polypeptide having the amino acid sequence according to one of SEQ ID No. 1 to SEQ ID No.

48 and SEQ ID No. 55 to SEQ ID No. 58 and SEQ ID No. 63 to SEQ ID No. 73 and SEQ ID No. 80 to SEQ ID No. 82. Examples of such functional variants are accordingly the polypeptides homologous to a polypeptide useable according to the invention, which originate from organisms other than the human or the mouse, preferably from non-human mammals such as, for example monkeys, pigs and rats. Other examples of functional variants are polypeptides which are encoded by different alleles of the gene, in different individuals or in different organs of an organism.

Sequence identity is understood as degree of identity (=% positives) of two sequences, that in the case of polypeptides can be determined by means of for example BlastP 2.0.1 and in the case of nucleic acids by means of for example BLASTN 2.014, wherein the Filter is set off (Altschul et al., 1997, Nucleic Acids Res., 25:3389–3402).

"Functional Variants" of the polypeptide can also be parts of the polypeptide used according to the invention with at least 6 amino acids length, preferably with at least 8 amino acids length, in particular with at least 12 amino acids length. Also included are deletions of the polypeptides used accordingly to the invention, in the range from about 1–60, preferably from about 1–30, in particular from about 1–15, especially from about 1–5 amino acids. For example, the first amino acid methionine can be absent without the function of the polypeptide being significantly altered.

In order to decide, whether a candidate polypeptide is a functional variant, the activity of the candidate funtional variant polypeptide may be compared with the activity of a polypeptide useable according to the invention in functional assays such as for example single cell or cell culture systems or standard wound healing assays. Assuming that the candidate functional variant polypeptide fulfills the criteria of a functional variant on the level of % sequence identity listed above the candidate funtional variant molecule represents a functional variant if the activity in the functional assays is similar to or identical with the activity exhibited by the polypeptide useable according to the invention.

Such standard wound healing assays comprise for example the application of an expression vector containing a nucleic acid coding for the candidate polypeptide or the application of the candidate polypeptide itself or of an antibody directed against the candidate polypeptide or of an antisense oligonucleotide to punched wounds, and after incubation for example of an expression vector comparing the progress of wound healing of wounds that have been injected with expression vectors containing e.g. the nucleic acid coding for the candidate funtional variant polypeptide, with the progress of wound healing of wounds injected with an expression vector containing the nucleic acid coding for the polypeptide useable according to the invention, or containing a control vector with no insert. Such assays may also be applied test the activity of candidate functional variant polypeptides in the case of disorders of wound healing employing for example badly healing wounds of dexamethasone-treated animals. For example, it was demonstrated that application of the polypeptide-variants PDGF-A and PDGF-B on badly healing rabbit wounds resulted in a comparable wound healing response (J. Surg. Res., 2000, 93:230–236). Similar tests can be carried out for skin disorders, for example Psoriasis. In this case, an expression vector containing a nucleic acid coding for the candidate polypeptide or the candidate polypeptide itself or an antibody directed against the candidate polypeptide or an antisense oligonucleotide are applied to for example human afflicted skin areas transplanted onto SCID mice and the course of the skin disorder, for example the healing, is determined, for example by measuring PASI-score in the case of psoriasis.

The term "coding nucleic acid" relates to a DNA sequence which codes for an isolatable bioactive polypeptide according to the invention or a precursor. The polypeptide can be encoded by a sequence of full length or any part of the coding sequence as long as the specific, for example enzymatic, activity is retained.

It is known that small alterations in the sequence of the nucleic acids described above can be present, for example, due to the degeneration of the genetic code, or that untranslated sequences can be attached to the 5' and/or 3' end of the nucleic acid without its activity being significantly altered. Also included are modifications that are carried out as described below. This invention, therefore, also comprises so-called "variants" of the nucleic acids described above "Variants" are understood as meaning all DNA sequences which are complementary to a DNA sequence, which hybridize with the reference sequence under stringent conditions and have a similar activity to the corresponding polypeptide according to the invention.

"Stringent hybridization conditions" are understood as meaning for example those conditions in which hybridization takes place at 60° C. in 2.5×SSC buffer, followed by a number of washing steps at 37° C. in a lower buffer concentration, and remains stable.

Variants of the nucleic acids can also be parts of the nucleic acids used according to the present invention with at least 8 nucleotides length, preferably with at least 18 nucleotides length, in particular with at least 24 nucleotides length particularly preferred with at least 30 nucleotides, and especially preferred with at least 42 nucleotides.

The term "pharmacologically active substance" in the sense of the present invention is understood as meaning all those molecules, compounds and/or compositions and substance mixtures which can interact under suitable conditions with the nucleic acids, polypeptides or antibodies or antibody fragments described above, if appropriate together with suitable additives and/or auxiliaries. Possible pharmacologically active substances are simple chemical organic or inorganic molecules or compounds, but can also include peptides, proteins or complexes thereof. Examples of pharmacologically active substances are organic molecules that are derived from libraries of compounds that have been analyzed for their pharmacological activity. On account of their interaction, the pharmacologically active substances can influence the function(s) of the nucleic acids, polypeptides or antibodies in vivo or in vitro or alternatively only bind to the nucleic acids, polypeptides or antibodies or antibody fragments described above or enter into other interactions of covalent or non-covalent manner with them.

The term "regulation" is understood, for example, as meaning the raising or lowering of the amount of polypeptide or nucleic acid encoding this. This may occur, for example, on the transcriptional or translational level.

The polypeptides according to the invention can furthermore be characterized in that they are synthetically prepared. Thus, the entire polypeptide or parts thereof can be synthesized, for example, with the aid of the conventional synthesis (Merrifield technique). Parts of the polypeptides according to the invention are particularly suitable to obtain antisera, with whose aid suitable gene expression banks can be searched in order thus to arrive at further functional variants of the polypeptide according to the invention.

Preferentially, the nucleic acids used according to the invention are DNA or RNA, preferably a DNA, in particular a double-stranded DNA. The sequence of the nucleic acids can furthermore be characterized in that it has at least one intron and/or one polyA sequence. The nucleic acids according to the invention can also be used in the form of their antisense sequence.

For the expression of the gene concerned, in general a double-stranded DNA is preferred, the DNA region coding for the polypeptide being particularly preferred. This region begins with the first start codon (ATG) lying in a Kozak sequence (Kozak, 1987, Nucleic. Acids Res. 15: 8125–48) up to the next stop codon (TAG, TGA or TAA), which lies in the same reading frame to the ATG.

A further use of the nucleic acid sequences according to the invention is the construction of anti-sense oligonucleotides (Zheng and Kemeny, 1995, Clin. Exp. Immunol. 100: 380–2; Nellen and Lichtenstein, 1993, Trends Biochem. Sci. 18: 419–23; Stein, 1992, Leukemia 6: 967–74) and/or ribozymes (Amarzguioui, et al. 1998, Cell. Mol. Life Sci. 54: 1175–202; Vaish, et al., 1998, Nucleic Acids Res. 26: 5237–42; Persidis, 1997, Nat. Biotechnol. 15: 921–2; Couture and Stinchcomb, 1996, Trends Genet. 12: 510–5). Using anti-sense oligonucleotides, the stability of the nucleic acid used according to the invention can be decreased and/or the translation of the nucleic acid used according to the invention inhibited. Thus, for example, the expression of the corresponding genes in cells can be decreased both in vivo and in vitro. Oligonuclecotides can therefore be suitable as therapeutics. This strategy is suitable, for example, for skin, epidermal and dermal cells, in particular if the antisense oligonucleotides are complexed with liposomes (Smyth et al., 1997, J. Invest. Dermatol. 108: 523–6; White et al., 1999, J. Invest. Dermatol. 112: 699–705; White et al., 1999, J. Invest. Dermatol. 112: 887–92). For use as a sample or as an "antisense" oligonucleotide, a single-stranded DNA or RNA is preferred.

Furthermore, a nucleic acid which has been prepared synthetically can be used for carrying out the invention. Thus, the nucleic acid according to the invention can be synthesized, for example, chemically with the aid of the DNA sequences described in Tables 3 to 5 and/or with the aid of the protein sequences likewise described in these tables with reference to the genetic code, e.g. according to the phosphotriester method (see, for example, Uhlmann, E. & Peyman, A. (1990) Chemical Reviews, 90, 543–584, No. 4).

As a rule, oligonucleotides are rapidly degraded by endo- or exo-nucleases, in particular by DNases and RNases occurring in the cell. It is therefore advantageous to modify the nucleic acid in order to stabilize it against degradation, so that a high concentration of the nucleic acid is maintained in the cell over a long period (Beigelman et al., 1995, Nucleic Acids Res. 23: 3989–94; Dudycz, 1995, WO 95/11910; Macadam et al., 1998, WO 98/37240; Reese et al., 1997, WO 97/29116). Typically, such a stabilization can be obtained by the introduction of one or more internucleotide phosphorus groups or by the introduction of one or more non-phosphorus internucleotides.

Suitable modified internucleotides are summarized in Uhlmann and Peymann (1990 Chem. Rev. 90, 544) (see also Beigelman et al., 1995 Nucleic Acids Res. 23: 3989–94; Dudycz, 1995, WO 95/11910; Madadam et al., 1998, WO 98/37240; Reese et al., 1997, WO 97/29116). Modified internucleotide phosphate radicals and/or non-phosphorus bridges in a nucleic acid which can be employed in one of the uses according to the invention contain, for example, methyl-phosphonate, phosphorothioate, phosphoramidate, phosphorodithioate, phosphate ester, while non-phosphorus internucleotide analogues, for example, contain siloxane bridges, carbonate bridges, carboxymethyl esters, acetamidate bridges and/or thioether bridges. It is also intended that this modification should improve the stability of a pharmaceutical composition which can be employed in one of the uses according to the invention.

In a further embodiment of the use according to the invention, the nucleic acids are comprised in a vector, preferably in a "shuttle" vector, phagemid, cosmid, expression vector or vector applicable in gene therapy. Furthermore, the above mentioned nucleic acids can be included in "knock-out" gene constructs or expression cassettes.

Preferably, the vector applicable in gene therapy contains wound- or skin-specific regulatory sequences which are functionally associated with the nucleic acid according to the invention.

The expression vectors can be prokaryotic or eukaryotic expression vectors. Examples of prokaryotic expression vectors are, for expression in *E. coli*, e.g. the vectors pGEM or pUC derivatives, examples of eukaryotic expression vectors are for expression in *Saccharomyces cerevisiae*, e.g. the vectors p426Met25 or p426GAL1 (Mumberg et al. (1994) Nucl. Acids Res., 22, 5767–5768), for expression in insect cells, e.g. Baculovirus vectors such as disclosed in EP-B1-0 127 839 or EP-B1-0 549 721, and for expression in mammalian cells, e.g. the vectors Rc/CMV and Rc/RSV or SV40 vectors, which are all generally obtainable.

In general, the expression vectors also contain promoters suitable for the respective host cell, such as, for example, the trp promoter for expression in *E. coli* (see, for example, EP-B1-0 154 133), the MET 25, GAL 1 or ADH2 promoter for expression in yeasts (Russel et al. (1983), J. Biol. Chem. 258, 2674–2682; Mumberg, supra), the Baculovirus polyhedrin promoter, for expression in insect cells (see, for example, EP-B1-0 127 839). For expression in mammalian cells, for example, suitable promoters are those which allow a constitutive, regulatable, tissue-specific, cell-cycle-specific or metabolically specific expression in eukaryotic cells. Regulatable elements according to the present invention are promoters, activator sequences, enhancers, silencers and/or repressor sequences.

Examples of suitable regulatable elements which make possible constitutive expression in eukaryotes are promoters which are recognized by the RNA polymerase III or viral promoters, CMV enhancer, CMV promoter, SV40 promoter or LTR promoters, e.g. from MMTV (mouse mammary tumor virus; Lee et al. (1981) Nature 214, 228–232) and further viral promoter and activator sequences, derived from, for example, HBV, HCV, HSV, HPV, EBV, HTLV or HIV.

Examples of regulatable elements which make possible regulatable expression in eukaryotes are the tetracycline operator in combination with a corresponding repressor (Gossen M. et al. (1994) Curr. Opin. Biotechnol. 5, 516–20).

Preferably, the expression of wound-healing-relevant genes takes place under the control of tissue-specific promoters, wherein skin-specific promoters such as, for example, the human K10 promoter (Bailleul et al., 1990. Cell 62: 697–708), the human K14 promoter (Vassar et al., 1989, Proc. Natl. Acad. Sci. USA 86: 1563–67), the bovine cytokeratin IV promoter (Fuchs et al., 1988; The biology of wool and hair (ed. G. E. Rogers, et al.), pp. 287–309. Chapman and Hall, London/New York) are particularly to be preferred.

Further examples of regulatable elements which make possible tissue-specific expression in eukaryotes are promoters or activator sequences from promoters or enhancers of those genes which code for proteins which are only expressed in certain cell types.

Examples of regulatable elements which make possible cell cycle-specific expression in eukaryotes are promoters of the following genes: cdc25A, cdc25B, cdc25C, cyclin A, cyclin E, cdc2, E2F-1 to E2F-5, B-myb or DHFR (Zwicker J. and Müller R. (1997) Trends Genet. 13, 3–6). The use of cell cycle regulated promoters is particularly preferred in cases, in which expression of the polypeptides or nucleic acids used according to the invention is to be restricted to proliferating cells.

An example of an regulatable element which makes possible the keratinocyte-specific expression in the skin, is the FiRE-element (Jaakkola et al., 2000, Gen. Ther., 7: 1640–1647). The FiRE element is a AP-1-driven, FGF-inducible response element of the Syndecan-1 gene (Jaakkola et al., 1998, FASEB J., 12: 959–9).

Examples of regulatable elements which make possible metabolically specific expression in eukaryotes are promoters which are regulated by hypoxia, by glucose deficiency, by phosphate concentration or by heat shock.

In order to make possible the introduction of nucleic acids as described above and thus the expression of the polypeptide in a eu- or prokaryotic cell by transfection, transformation or infection, the nucleic acid can be present as a plasmid, as part of a viral or non-viral vector. Suitable viral vectors here are particularly: baculoviruses, vaccinia viruses, adenoviruses, adeno-associated viruses and herpesviruses. Suitable non-viral vectors here are particularly: virosomes, liposomes, cationic lipids, or poly-lysine-conjugated DNA.

Examples of vectors having gene therapy activity are virus vectors, for example adenovirus vectors or retroviral vectors (Lindemann et al., 1997, Mol. Med. 3: 466–76; Springer et al., 1998, Mol. Cell. 2: 549–58). Eukaryotic expression vectors are suitable in isolated form for gene therapy use, as naked DNA can penetrate into skin cells on topical application (Hengge et al., 1996, J. Clin. Invest. 97: 2911–6; Yu et al., 1999, J. Invest. Dermatol. 112: 370–5).

Vectors having gene therapy activity can also be obtained by complexing the nucleic acid with liposomes, since a very high transfection efficiency, in particular of skin cells, can thus be achieved (Alexander and Akhurst, 1995, Hum. Mol. Genet. 4: 2279–85). In the case of lipofection, small unilamellar vesicles are prepared from cationic lipids by ultrasonic treatment of the liposome suspension. The DNA is bound ironically to the surface of the liposomes, namely in such a ratio that a positive net charge remains and the plasmid DNA is complexed to 100% of the liposomes. In addition to the lipid mixtures DOTMA (1,2dioleyloxypropyl-3-trimethylammonium bromide) and DPOE (dioleoylphosphati-dylethanolamine) employed by Felgner et al. (1987, supra), meanwhile numerous novel lipid formulations were synthesized and tested for their efficiency in the transfection of various cell lines (Behr et al. 1989, Proc. Natl. Acad. Sci. USA 86: 6982–6986; Felgner et al., 1994, J. Biol. Chem. 269:2550–2561; Gao, X. and Huang, 1991, Biochim. Biophys. Acta 1189:195–203). Examples of the novel lipid formulations are DOTAP N-[1-(2,3-dioleoyloxy)propyl]-N,N,N-trimethylammonium ethyl-sulphate or DOGS (TRANSFECTAM; dioctadecylamidoglycylspermine). Other lipids suitable for transfection in vivo and in vitro are the cationic lipids Cytofectin GS 2888 (U.S. Pat. No. 5,777,153; Lewis et al., 1996, Proc. Natl. Acad. Sci. USA, 93: 3176–3181). Auxiliaries which increase the transfer of nucleic acids into the cell can be, for example, proteins or peptides which are bound to DNA or synthetic peptide-DNA molecules which make possible the transport of the nucleic acid into the nucleus of the cell (Schwartz et al., 1999, Gene Therapy 6:282; Brandén et al., 1999, Nature Biotech. 17:784). Auxiliaries also include molecules which make possible the release of nucleic acids into the cytoplasm of the cell (Planck et al., 1994, J. Biol. Chem. 269:12918; Kichler et al. (1997) Bioconj. Chem. 8:213) or, for example, liposomes (Uhlmann and Peymann, 1990, supra). Another particularly suitable form of gene therapy vectors can be obtained by applying the above described nucleic acid to gold particles and shooting these into tissue, preferably into the skin, or cells with the aid of the so-called gene gun (Wang et al., 1999, J. Invest. Dermatol. 112: 775–81, Tuting et al., 1998, J. Invest. Dermatol. 111: 183–8).

A further form of a vector applicable in gene therapy can be prepared by the introduction of "naked" expression vectors into a biocompatible matrix, for example a collagen matrix. This matrix can be introduced into wounds in order to transfect the immigrating cells with the expression vector and to express the polypeptides according to the invention in the cells (Goldstein and Banadio, U.S. Pat. No. 5,962,427).

For gene therapy use of the above described nucleic acid, it is also advantageous if the part of the nucleic acid which codes for the polypeptide contains one or more non-coding sequences including intron sequences, preferably between promoter and the start codon of the polypeptide, and/or a polyA sequence, in particular the naturally occurring polyA sequence or an SV40 virus polyA sequence, especially at the 3' end of the gene, as a stabilization of the mRNA can be achieved thereby (Palmiter et al., 1991, Proc. Natl. Acad. Sci. USA 88:478–482; Jackson, 1993, Cell 74:9–14).

Knock-out gene constructs are known to the person skilled in the art, for example, from the U.S. Pat. Nos. 5,625,122; 5,698,765; 5,583,278 and 5,750,825.

A further preferred embodiment of the present invention is the use of a cell, preferentially of an autologous or heterologous cell, in particular a skin cell, which is transformed with a vector useable according to the invention or with a knock-out gene construct, for the diagnosis and/or prevention and/or treatment of diseases of skin cells and/or of wound healing and/or of their pathological disorders, and/or for the identification of pharmacologically active substances. Cells can be either prokaryotic or eukaryotic cells; examples of prokaryotic cells are *E. coli* and of eukaryotic cells are *Saccharomyces cerevisiae* or insect cells.

A particularly preferred transformed host cell is a transgenic embryonic non-human stem cell, which is characterized in that it comprises at least one knock-out gene construct and/or an expression cassette as described above. Processes for the transformation of host cells and/or stem cells are well known to the person skilled in the art and include, for example, electroporation or microinjection.

The genome of transgenic non-human mammals comprises at least one knock-out gene construct and/or an expression cassette as described above. Transgenic animals in general show a tissue-specifically increased expression of the nucleic acids and/or polypeptides and can be used for the analysis of wound healing disorders. Thus, for example, an activin A transgenic mouse exhibits improved wound healing (Munz et al., 1999, EMBO J. 18: 5205–15) while a transgenic mouse having a dominantly negative KGF receptor exhibits delayed wound healing (Werner et al., 1994, Science 266: 819–22).

Processes for the preparation of transgenic animals, in particular of transgenic mice, are likewise known to the person skilled in the art from DE 196 25 049 and U.S. Pat. Nos. 4,736,866; 5,625,122; 5,698,765; 5,583,278 and 5,750, 825 and include transgenic animals which can be produced, for example, by means of direct injection of expression vectors (see above) into embryos or spermatocytes or by means of the transfection of expression vectors into embryonic stem cells (Polites and Pinkert: DNA Microinjection and Transgenic Animal Production, page 15 to 68 in Pinkert, 1994: Transgenic animal technology: a laboratory handbook, Academic Press, London, UK; Houdebine, 1997, Harwood Academic Publishers, Amsterdam, The Netherlands; Doetschman: Gene Transfer in Embryonic Stem Cells, page 115 to 146 in Pinkert, 1994, supra; Wood: Retrovirus-Mediated Gene Transfer, page 147 to 176 in Pinkert, 1994, supra; Monastersky: Gene Transfer Technology; Alternative Techniques and Applications, page 177 to 220 in Pinkert, 1994, supra).

If the above described nucleic acids are integrated into so-called "targeting" vectors or "knock-out" gene constructs (Pinkert, 1994, supra), it is possible after transfection of embryonic stem cells and homologous recombination, for example, to generate knock-out mice which, in general, as heterozygous mice, show decreased expression of the nucleic acid, while homozygous mice no longer exhibit expression of the nucleic acid. The animals thus produced can also be used for the analysis of wound healing disorders. Thus, for example, the eNOS (Lee et al., 1999, Am. J. Physiol. 277: H1600–1608), Nf-1 (Atit et al., 1999, J. Invest. Dermatol. 112: 835–42) and osteopontin (Liaw et al., 1998, J. Clin. Invest. 101: 967–71) knock-out mice exhibit impaired wound healing. Here too, a tissue-specific reduction of the expression of wound healing-relevant genes, for example in skin-specific cells using the Cre-loxP system (stat3 knock-out, Sano et al., EMBO J 1999 18: 4657–68), is particularly to be preferred. Transgenic and knock-out cells or animals produced in this way can also be used for the screening and for the identification of pharmacologically active substances vectors having gene therapy activity.

Polypeptides useable according to the invention can be prepared according to generally known recombinant processes. Furthermore, polypeptides useable according to the invention can be isolated from an organism or from tissue or cells and used according to the invention. Thus, it is possible, for example, to purify polypeptides useable according to the invention from mammal tissue, for example from skin or body fluids such as for example blood, serum, saliva, synovial fluid, wound liquid. Furthermore, starting from cells expressing polypeptides useable according to the invention, cell lines can be prepared which can then be used for the isolation of polypeptides useable according to the invention. For example skin cells, such as for example HaCaT cells can be transformed with expression vectors containing nucleic acids useable according to the invention. The expression can be for example constitutive or inducible.

The polypeptide is prepared, for example, by expression of the above described nucleic acids in a suitable expression system, as already mentioned above, according to the methods generally known to the person skilled in the art. Suitable host cells are, for example, the *E. coli* strains DH5, HB101 or BL21, the yeast strain *Saccharomyces cerevisiae,* the insect cell line Lepidoptera, e.g. from *Spodoptera frugiperda,* or the animal cells COS, Vero, 293, HaCaT, and HeLa, which are all generally obtainable.

A further embodiment relates to the use of the polypeptides according to the invention, the polypeptides being employed in the form of a fusion protein. Fusion proteins useable according to the invention can be prepared, for example, by expressing nucleic acids useable according to the invention of a suitable cell.

The fusion proteins useable according to the invention themselves already having the function of a polypeptide of the invention or the specific function being functionally active only after cleavage of the fusion portion. Especially included here are fusion proteins having a proportion of about 1–300, preferably about 1–200, in particular about 1–100, especially about 1–50, foreign amino acids. Examples of such peptide sequences are prokaryotic peptide sequences, which can be derived, for example, from the galactosidase of *E. coli*. Furthermore, viral peptide sequences, such as, for example, of the bacteriophage M13 can also be used in order thus to produce fusion proteins for the phage display process known to the person skilled in the art.

Further preferred examples of peptide sequences for fusion proteins are peptides, that facilitate easier detection of the fusion proteins, these are, for example, "Green-fluorescent-protein" or functional variants thereof (WO 95/07463).

For the purification of the proteins described above (a) further polypeptide(s) (tag) can be attached. Protein tags according to the invention allow, for example, high-affinity absorption to a matrix, stringent washing with suitable buffers without eluting the complex to a noticeable extent and subsequently targeted elution of the absorbed complex. Examples of the protein tags known to the person skilled in the art are a $(His)_6$ tag, a Myc tag, a FLAG tag, a haemagglutinin tag, glutathione transferase (GST) tag, intein having an affinity chitin-binding tag or maltose-binding protein (MBP) tag. These protein tags can be situated N- or C-terminally and/or internally.

A further embodiment of the invention relates to the use of an antibody or an antibody fragment directed against a polypeptide useable according to the invention or a functional variant thereof, preferably of a polyclonal or monoclonal antibody or antibody fragment, for the analysis, diagnosis, prevention and/or treatment of diseases of skin cells, of wound healing and/or disorders of wound healing, and its use for the identification of pharmacologically active substances, if appropriate combined or together with suitable additives and/or auxiliaries.

Thus the local injection, for example, of monoclonal antibodies against TGF beta 1 in the animal model can improve wound healing (Ernst et al., 1996, Gut 39:172–5).

The process for manufacturing an antibody or an antibody fragment is carried out according to methods generally known to the person skilled in the art by immunizing a mammal, for example a rabbit, with said polypeptide or parts thereof having at least 6 amino acid length, preferably having at least 8 amino acid length, in particular having at least 12 amino acid length, if appropriate in the presence of, for example, Freund's adjuvant and/or aluminium hydroxide gels (see, for example, Diamond et al., 1981, The New England Journal of Medicine, 1344–1349). The polyclonal antibodies formed in the animal as a result of an immunological reaction can then be easily isolated from the blood according to generally known methods and purified, for example, by means of column chromatography. Monoclonal antibodies can be produced, for example, according to the known method of Winter & Milstein (Winter, G. & Milstein, C. (1991) Nature, 349, 293–299). As alternatives to the classical antibodies, for example, "anticalins" based on lipocalin can be used (Beste et al., 1999, Proc. Natl. Acad. Sci. USA, 96:1898–1903). The natural ligand-binding sites of the lipocalins, such as the retinol-binding protein or the bilin-binding protein can be modified, for example, by a "combinatorial protein design" approach in a manner such that they bind to selected haptens, for example to the polypeptides useable according to the invention (Skerra, 2000, Biochim. Biophys. Acta 1482:337–50). Further known "scaffolds" are known as alternatives for antibodies for molecular recognition (Skerra, J. Mol. Recognit., 2000, 13:167–187).

The antibody useable according to the invention or the antibody fragment is directed against a polypeptide according to the invention and reacts specifically with the polypeptides according to the invention, where the above mentioned parts of the polypeptide either are immunogenic themselves or can be rendered immunogenic or increased in their immunogenicity by coupling to suitable carriers, such as bovine serum albumin. This antibody useable according to the invention is either polyclonal or monoclonal; a monoclonal antibody is preferred. The term antibody or antibody fragment is understood according to the present invention as also meaning antibodies or antigen-binding parts thereof prepared by genetic engineering and optionally modified, such as chimeric antibodies, humanized antibodies, multifunctional antibodies, bi- or oligospecific antibodies, single-stranded antibodies, F(ab) or F(ab)$_2$ fragments (see, for example, EP-B1–0 368 684, U.S. Pat. Nos. 4,816,567, 4,816,397, WO 88/01649, WO 93/06213, WO 98/24884).

The identified pharmacologically active substances can be used, if appropriate combined or together with suitable additives and/or auxiliaries, for the production of a diagnostic or of a medicament for the prevention, treatment and/or diagnosis of diseases of skin cells and/or in wound healing and/or their pathological disorders.

In order to use nucleic acids as a diagnostic the polymerase chain reaction can be employed as described below. For the use of nucleic acids as a medicament, a vector applicable for gene therapy or antisense nucleotides can be utilized as described.

In order to use other organic or anorganic pharmacologically active substances as a medicament, they can be applied as described above. Antibodies can be utilized as a diagnostic by means of immunological techniques as described above, for example by using antibodies that are labeled with an enzyme. The specific antibody-peptide complex can be determined easily and quickly by means of an enzymatic color-reaction.

In order to use pharmacologically active substances as a diagnostic, substances may contain a detectable marker, for example the substance may be radioactively labeled, fluorescence-labeled or luminescence-labeled. In addition substances may be coupled to enzymes, that allow indirect detection, for example by enzymatic catalysis by means of peroxidase-assay using a chromogenic substrate as described above or by binding of a labeled or detectable antibody. The substances can be brought into contact with the sample and thus the amount of polypeptides useable according to the invention or a functional variant thereof or nucleic acids coding for this or a variant thereof, or a cell containing a polypeptide useable according to the invention or a functional variant thereof or a nucleic acid coding for this, or an antibody directed against a polypeptide useable according to the invention or a fragment thereof, can be determined. The result of the sample, being isolated from an organism to be analyzed, can be compared with the result of a sample, of a healthy or a pathological organism.

The present invention also relates to the use of at least one polypeptide useable according to the invention or a functional variant thereof and/or of a nucleic acid encoding this or a variant thereof, and/or of a cell expressing a polypeptide useable according to the invention or of a functional variant thereof or a nucleic acid encoding this or a variant thereof, and/or of an antibody or an antibody fragment directed against a polypeptide useable according to the invention, optionally combined or together with suitable additives and/or auxiliaries, for the production of a medicament for the prevention and/or treatment of diseases of skin cells, of wound healing and/or their pathological disorders.

The medicament useable according to the invention may be used for the prevention and/or treatment of diseases of skin cells, of wound healing and/or their pathological disorders, wherein at least one polypeptide useable according to the invention or a functional variant thereof or a nucleic acid encoding this, and/or a cell expressing a polypeptide useable according to the invention or a functional variant thereof or a nucleic acid encoding this or a variant thereof, and/or an antibody or an antibody fragment directed against a polypeptide useable according to the invention or a functional variant thereof, if appropriate combined or together with suitable additives and/or auxiliaries, is being employed.

The therapy of the disorders, of skin disorders, of wound healing and/or disorders of wound healing, can be carried out in a conventional manner, e.g. by means of dressings, plasters, compresses or gels which contain the medicaments according to the invention. It is thus possible to administer the pharmaceuticals containing the suitable additives and/or auxiliaries, such as, for example, physiological saline solution, demineralized water, stabilizers, proteinase inhibitors, gel formulations, such as, for example, white petroleum jelly, highly liquid paraffin and/or yellow wax, etc., topically and locally in order to influence wound healing immediately and directly. The administration of the medicaments according to the invention can furthermore also be carried out topically and locally in the area of the wound, if appropriate in the form of liposome complexes or gold particle complexes. Furthermore, the treatment can be carried out by means of a transdermal therapeutic system (TTS), which makes possible a temporally controlled release of the medicaments according to the invention. The treatment by means of the medicaments according to the invention, however, can also be carried out by means of oral dosage forms, such as, for example, tablets or capsules, by means of the mucous membranes, for example the nose or the oral cavity, or in the form of dispositories implanted under the skin. TTS are known for example, from EP 0 944 398 A1, EP0 916 336 A1, EP 0 889 723 A1 or EP 0 852 493 A1.

For gene therapy use in humans, an especially suitable medicament is one which contains the described nucleic acid in naked form or in the form of one of the vectors having gene therapy activity described above or in a form complexed with liposomes or gold particles. The pharmaceutical carrier is, for example, a physiological buffer solution, preferably having a pH of about 6.0–8.0, preferably of about 6.8–7.8, in particular of about 7.4, and/or an osmolarity of about 200–400 milliosmol/liter, preferably of about 290–310 milliosmol/liter. In addition, the pharmaceutical carrier can contain suitable stabilizers, such as nuclease inhibitors, preferably complexing agents such as EDTA and/or other auxiliaries known to the person skilled in the art.

The nucleic acid described is optionally administered in the form of the virus vectors described above in greater detail or as liposome complexes or a gold particle complex, customarily topically and locally in the area of the wound. It is also possible to administer the polypeptide itself with suitable additives and/or auxiliaries, such as physiological saline solution, demineralized water, stabilizers, protease inhibitors, gel formulations, such as white petroleum jelly, highly liquid paraffin and/or yellow wax, etc., in order to affect wound healing immediately and directly.

Examples of disorders of skin cells within the meaning of the invention is understood as psoriasis, eczema, especially atopic eczema, acne, Urticaria, disorders of pigmentation of the skin, especially vitiligo, senile skin, and disorders of hair growth and hair metabolism.

Wound healing within the meaning of the invention is understood as the healing process of a mechanical wound of the skin, such as for example laceration, skin abrasion or excoriation of the skin, for example by means of a permanent load, for example decubitus or necrotic processes, for example *Necrobiosis lipoidica*.

Examples of disorders of wound healing in the meaning of the invention comprise wounds of patients suffering from diabetes or alcoholism, wounds infected with organisms or viruses, ischemic wounds, wounds of patients suffering from arterial disorders, or venous insufficiency, and scars, preferably overshooting scars, especially keloids. Especially preferred badly healing wounds comprise diabetic, neuropathic, venous or arterial ulcers, especially diabetic ulcers.

The present invention furthermore relates to the use of at least one polypeptide useable according to the invention or a functional variant thereof and/or of a nucleic acid encoding this or a variant thereof, and/or of a cell expressing a polypeptide useable according to the invention or a functional variant thereof or a nucleic acid encoding this or a variant thereof, and/or of an antibody or of an antibody fragment directed against a polypeptide useable according to the invention or a functional variant thereof, if appropriate combined or together with suitable additives and/or auxiliaries, for the production of a diagnostic for the diagnosis of diseases of skin cells and/or in wound healing and/or their pathological disorders.

For example, it is possible according to the present invention to prepare a diagnostic based on the polymerase chain reaction (Examples 2, 4 to 7, PCR diagnostic, e.g. according to EP 0 200 362) or an RNase protection assay (see, for instance, Sambrook et al., supra chapter 7, page 7.71–7.78, Werner et al., 1992, Growth Factor and Receptors: A Practical Approach 175–197, Werner, 1998, Proc. Natl. Acad. Sci. U.S.A. 89: 6896–699) with the aid of a nucleic acid as described above. These tests are based on the specific hybridization of a nucleic acids with its complementary counter strand, usually of the corresponding mRNA or its cDNA. The nucleic acid described above can in this case also be modified, such as disclosed, for example, in EP 0 063 879. Preferably a DNA fragment is labeled according to generally known methods by means of suitable reagents, e.g. radioactively with $\alpha$-$P^{32}$-dCTP or non-radioactively with biotin or digoxigenin, and incubated with isolated RNA, which has preferably been bound beforehand to suitable membranes of, for example, cellulose or nylon. With the same amount of investigated RNA from each tissue sample, the amount of mRNA which was specifically labeled by the sample can thus be determined. Alternatively, the determination of mRNA amount can also be carried directly out in tissue sections with the aid of in situ hybridization (Werner et al., 1992, Proc. Natl. Acad. Sci. USA 89: 6896–6900).

The diagnostic useable according to the invention is used for the diagnosis of diseases of skin cells and/or in wound healing and/or their pathological disorders, wherein at least one polypeptide useable according to the invention or a functional variant thereof and/or a nucleic acid encoding this or a variant thereof, and/or a cell expressing a polypeptide useable according to the invention or a functional variant thereof or nucleic acid coding for this or a variant thereof, and/or an antibody or an antibody fragment directed against a polypeptide useable according to the invention or a functional variant thereof, if appropriate combined or together with suitable additives and/or auxiliaries, is employed.

The diagnostic useable according to the invention, can thus also be used to specifically measure the strength of expression in a tissue sample in order to be able to safely diagnose, for example, a wound healing disorder or dermatological disorders (Examples 2, 4 to 7). Such a process is particularly suitable for the early prognosis of disorders.

A preferred diagnostic useable according to the invention contains the described polypeptide or the immunogenic parts thereof described in greater detail above. The polypeptide or the parts thereof, which are preferably bound to a solid phase, e.g. of nitrocellulose or nylon, can be brought into contact in vitro, for example, with the body fluid to be investigated, e.g. wound secretion, in order thus to be able to react, for example, with autoimmune antibodies. The antibody-peptide complex can then be detected, for example, with the aid of labeled anti-human IgG or antihuman IgM antibodies. The labeling involves, for example, an enzyme, such as peroxidase, which catalyses a color reaction. The presence and the amount of autoimmune antibody present can thus be detected easily and rapidly by means of the color reaction.

A further diagnostic useable according to the invention, that is that subject matter of the present invention, contains the antibodies useable according to the invention themselves. With the aid of these antibodies, it is possible, for example, to easily and rapidly investigate a tissue sample as to whether the concerned polypeptide is present in an increased amount in order to thereby obtain an indication of possible disorders, in particular skin disorder, and wound healing disorder. In this case, the antibodies according to the invention are labeled, for example, with an enzyme, as already described above. The specific antibody-peptide complex can thereby be detected easily and also rapidly by means of an enzymatic color reaction.

A further diagnostic useable according to the invention comprises a sample, preferably a DNA sample, and/or primer. This opens up a further possibility of obtaining the described nucleic acids, for example by isolation from a suitable gene bank, for example from a wound-specific gene bank, with the aid of a suitable sample (see, for example, J. Sambrook et al., 1989, Molecular Cloning. A Laboratory Manual 2nd edn., Cold Spring Harbor Laboratory, Cold Spring Harbor, N.Y. Chapter 8 page 8.1 to 8.81, Chapter 9 page 9.47 to 9.58 and Chapter 10 page 10.1 to 10.67).

Suitable samples are, for example, DNA or RNA fragments having a length of about 100–1000 nucleotides, preferably having a length of about 200–500 nucleotides, in particular having a length of about 300–400 nucleotides, whose sequence can be derived from the polypeptides according to SEQ ID No. 1 to SEQ ID No. 48, SEQ ID No. 55 to SEQ ID No. 58 and SEQ ID No. 63 to SEQ ID No. 73 and SEQ ID No. 80 to SEQ ID No. 82 of the sequence protocol and/or with the aid of the cDNA sequences of the database entries indicated in Tables 3 to 5 or with the aid of the sequence protocol according to SEQ ID No. 50 to SEQ ID No. 54 and SEQ ID No. 83 to SEQ ID No. 84.

Alternatively, it is possible with the aid of the derived nucleic acid sequences to synthesize oligonucleotides which are suitable as primers for a polymerase chain reaction.

Using this, the nucleic acid described above or parts of this can be amplified and isolated from cDNA, for example wound-specific cDNA (Example 2). Suitable primers are, for example, DNA fragments having a length of about 10 to 100 nucleotides, preferably having a length of about 15 to 50 nucleotides, in particular having a length of 20 to 30 nucleotides, whose sequence can be derived from the polypeptides according to SEQ ID No. 1 to SEQ ID No. 48, SEQ ID No. 55 to SEQ ID No. 58 and SEQ ID No. 63 to SEQ ID No. 73 and SEQ ID No. 80 to SEQ ID No. 82 of the sequence protocol and/or with the aid of the cDNA sequences of the database entries indicated in Tables 3 to 5 or with the aid of the sequence protocol according to SEQ ID No. 50 to SEQ ID No. 54 and SEQ ID No. 83 to SEQ ID No. 84.

The present invention also relates to the use of at least one antibody or antibody fragment directed against a polypeptide useable according to the invention for the identification of pharmacologically active substances, wherein the antibody/antibodies or antibody fragment(s) is/are bound to a solid phase.

The present invention furthermore relates to the use of at least one polypeptide useable according to the invention or a functional variant thereof and/or of a nucleic acid encoding this or a variant thereof, and/or of a cell expressing a polypeptide useable according to the invention or a functional variant thereof or a nucleic acid coding for this or a variant thereof, and/or of an antibody or an antibody fragment directed against a polypeptide useable according to the invention or a functional variant thereof, if appropriate combined or together with suitable additives and/or auxiliaries, for the production of a test for finding pharmacologically active substances in connection with skin diseases and/or in connection with wound healing, in particular wound healing disorders.

At least one polypeptide useable according to the invention or a functional variant thereof and/or of a nucleic acid encoding this or a variant thereof, and/or of a cell expressing a polypeptide useable according to the invention or a functional variant thereof or a nucleic acid coding for this or a variant thereof, and/or of an antibody or an antibody fragment directed against a polypeptide useable according to the invention or a functional variant thereof, if appropriate combined or together with suitable additives and/or auxiliaries, may be used in the form of a test for finding pharmacologically active substances in connection with diseases of skin cells and/or in wound healing and/or their pathological disorders.

In a preferred embodiment of the invention the test system comprises at least one polypeptide useable according to the invention and/or at least one antibody or antibody fragment useable according to the invention, which is bound to a solid-phase.

In an other preferred embodiment of the invention the test system comprises at least one cell expressing at least one polypeptide useable according to the invention or a nucleic acid coding for this.

A suitable system can be produced, for example, by the stable transformation of epidermal or dermal cells with expression vectors which contain selectable marker genes and the described nucleic acids. In this process, the expression of the described nucleic acids is altered in the cells such that it corresponds to the pathologically disturbed expression in vivo. Anti-sense oligonucleotides which contain the described nucleic acid can also be employed for this purpose. It is therefore of particular advantage for these systems to know the expression behavior of the genes in disturbed regenerative processes, such as disclosed in this application. Often, the pathological behavior of the cells in vitro can thus be mimicked and substances can be sought which reproduce the normal behavior of the cells and which have a therapeutic potential.

Suitable cells for these test systems useable according to the invention are, for example, HaCaT cells, which are generally obtainable, and the expression vector pCMV4 (Anderson et al., 1989, J. Biol. Chem. 264: 8222–9). The nucleic acid as described above can in this case be integrated into the expression vectors both in the sense and in the anti-sense orientation, such that the functional concentration of mRNA of the corresponding genes in the cells is either increased, or is decreased by hybridization with the anti-sense RNA. After the transformation and selection of stable transformants, the cells in culture in general show an altered proliferation, migration and/or differentiation behavior in comparison with control cells. This behavior in vitro is often correlated with the function of the corresponding genes in regenerative processes in the body (Yu et al., 1997, Arch. Dermatol. Res. 289: 352–9; Mils et al., 1997, Oncogene 14: 15555–61; Charvat et al., 1998, Exp Dermatol 7: 184–90; Werner, 1998, Cytokine Growth Factor Rev. 9: 153–65; Mythily et al., 1999, J. Gen. Virol. 80: 1707–13;) and can be detected using tests which are simple and rapid to carry out, such that test systems for pharmacologically active substances based thereon can be constructed. Thus, the proliferation behavior of cells can be detected very rapidly by, for example, the incorporation of labeled nucleotides into the DNA of the cells (see, for example, Savino and Dardenne, 1985, J. Immunol. Methods 85: 221–6; Perros and Weightman, 1991, Cell Prolif. 24: 517–23; Fries and Mitsuhashi, 1995, J. Clin. Lab. Anal. 9: 89–95), by staining the cells with specific stains (Schulz et al., 1994, J. Immunol. Methods 167: 1–13) or by means of immunological processes (Frahm et al., 1998, J. Immunol. Methods 211: 43–50). The migration can be detected simply by the migration index test (Charvat et al., supra) and comparable test systems (Benestad et al., 1987, Cell Tissue Kinet. 20: 109–19, Junger et al., 1993, J. Immunol. Methods 160: 73–9). Suitable differentiation markers are, for example, keratin 6, 10 and 14 and also loricrin and involucrin (Rosenthal et al., 1992, J. Invest. Dermatol. 98: 343–50), whose expression can be easily detected, for example, by means of generally obtainable antibodies.

Another suitable test system systems useable according to the invention is based on the identification of interactions using the so-called two-hybrid system (Fields and Sternglanz, 1994, Trends in Genetics, 10, 286–292; Colas and Brent, 1998 TIBTECH, 16, 355–363). In this test, cells are transformed using expression vectors which express fusion proteins from the polypeptide according to the invention and a DNA binding domain of a transcription factor such as, for example, Gal4 or LexA. The transformed cells additionally contain a reporter gene, whose promoter contains binding sites for the corresponding DNA binding domains. By transformation of a further expression vector which expresses a second fusion protein from a known or unknown polypeptide having an activation domain, for example of Gal4 or *Herpes simplex* virus VP 16, the expression of the reporter gene can be greatly increased if the second fusion protein interacts with the polypeptide according to the invention. This increase in expression can be utilized in order to identify novel pharmacologically active substances, for example by preparing a cDNA library from regenerating tissue for the construction of the second fusion protein. Moreover, this test system can be utilized for the screening of substances which inhibit an interaction between the polypeptide according to the invention and pharmacologically active substance. Such substances decrease the expression of the reporter gene in cells which express fusion proteins of the polypeptide according to the invention and of the pharmacologically active substance (Vidal and Endoh, 1999, Trends in Biotechnology; 17: 374–81). Novel active compounds which can be employed for the therapy of disorders of regenerative processes can thus be rapidly identified.

Furthermore a test system may be based on binding a polypeptide useable according to the invention, or a functional variant thereof and/or a nucleic acid coding for this or a variant thereof, and/or an antibody or an antibody fragment directed against a polypeptide useable according to the invention or a functional variant thereof, to a solid phase and test substances for interactions, for example for binding or for changes of the conformation. Suitable systems such as affinity chromatography and fluorescence spectroscopy are known to the person skilled in the art.

Solid-phase bound polypeptides useable according to the invention, or functional variants thereof or nucleic acids coding for these or variants thereof, or antibodies or antibody fragments directed against polypeptides useable according to the invention or functional variants thereof can also be part of an array.

In a preferred embodiment of the invention at least one polypeptide useable according to the invention or a nucleic acid coding for this, or at least one antibody or antibody fragment useable according to the invention may be used in the form of an array fixated to a carrier, for the annalysis in connection with diseases of skin cells, of wound healing and/or disorders of wound healing.

Processes for the production of arrays by means of solid-phase chemistry and photolabile protecting groups are known from U.S. Pat. No. 5,744,305. Such arrays can also be brought into contact with substances or libraries of substances in order to test the substances for interactions, for example for binding or for changes of the conformation.

A substance to be tested may for example contain a detectable marker, for example a substance which is radioactively labeled, fluorescence-labeled or luminescence-labeled. Furthermore substances may be coupled to proteins, that allow indirect detection, for example by enzymatic catalysis using a peroxidase-assay with a chromogenic substrate or by binding of a detectable antibody. Modifications of the conformation of a polypeptide useable according to the invention can be detected by interaction with a suitable test-substance that for example changes fluorescence of an endogenous tryptophan within the molecule.

Pharmacologically active substances of the polypeptides according to the invention can also be nucleic acids which are isolated by means of selection processes, such as, for example, SELEX (see Jayasena, 1999, Clin. Chem. 45: 1628–50; Klug and Famulok, 1994, M. Mol. Biol. Rep. 20: 97–107; Toole et al., 1996, U.S. Pat. No. 5,582,981). In the SELEX process, typically those molecules which bind to a polypeptide with high affinity (aptamers) are isolated by repeated amplification and selection from a large pool of different, single-stranded RNA molecules. Aptamers can also be synthesized and selected in their enantiomorphic form, for example as the L-ribonucleotide (Nolte et al., 1996, Nat. Biotechnol. 14: 1116–9; Klussmann et al., 1996, Nat. Biotechnol. 14: 1112–5). Thus isolated forms have the advantage that they are not degraded by naturally occurring ribonucleases and therefore have greater stability.

In a preferred embodiment of the invention, a test for identifying pharmacologically active substances is used, where candidate substances are tested for their influence on the expression of at least one nucleic acid useable according to the invention.

Assays for the identification of pharmacologically active substances, which influence the expression of genes are known to the person skilled in the art (see for example Sivaraja et al., 2001, U.S. Pat. No. 6,183,956).

It is possible for example to cultivate cells, which express nucleic acids useable according to the invention, for example HeLa cells as a test system for the analysis of gene expression in vitro. Preferably the cells are skin cells, even more preferably they are keratinocytes, fibroblasts or endothelial cells. A possible test system constitutes the human keratinocyte cell line HaCat which is generally available.

The analysis of gene expression can be performed for example on the mRNA or protein level. Here, the amount of nucleic acid or protein useable according to the invention is measured after the application of one or more candidate substances to the cell culture and is then compared with the amount in a control cell culture. This can be performed for example by hybdridization of an antisense probe which can be used to detect mRNA of target genes useable according to the invention in cell lysates. Quantification can be performed for example by binding of a specific antibody to the mRNA-probe complex (see Stuart and Frank, 1998, U.S. Pat. No. 4,732,847). It is possible to perform the analysis as a high-throughput analysis to test a lot of substances with respect to their suitability as modulator of gene expression of nucleic acids useable according to the invention (Sivaraja et al., 2001, U.S. Pat. No. 6,183,956). The substances to be analysed can be taken from substance libraries (see for example. DE19816414, DE19619373) which contain several thousand, often very heterogeneous substances. Alternatively, the total RNA or mRNA can be isolated from cells and subsequently the absolute or relative amount of mRNA of a target gene useable according to the invention can be determined for example by the use of quantitative RT-PCR (see EP 0 200 362; Wittwer et al., 1997, BioTechniques 22:130–8; Morrison et al., 1998, BioTechniques 24: 954–62) or RNAse Protection Assays (see for example Sambrook et al., 1989, Molecular cloning: A Laboratory Manual, Cold Spring Harbor, Cold Spring Harbor Laboratory Press, New York, chapter 7; EP 0 063 879). Another possibility constitutes the detection of the amount of protein in cell lysate by the use of an antibody which specifically detects the protein useable according to the invention. The quantification can for example be performed by the use of an ELISA or Western blot analysis, which are generally known to a person skilled in the art. To determine the specificity of the substances for the expression of nucleic acids useable according to the invention, the influence of the candidate substances on the target gene expression can be compared to the influence on the expression on other genes, for example genes of the cell metabolism like GAPDH. This can be performed in separately or in parallel to the analysis of the nucleic acids useable according to the invention.

The pharmacologically active substances identified with the aid of the test procedures useable according to the invention can be used, if appropriate combined or together with suitable additives and/or auxiliaries, for the production of a diagnostic or medicament for the diagnosis, prevention and/or treatment of diseases of skin cells, of wound healing and/or their pathological disorders.

A further subject of the invention relates to the use of at least one polypeptide useable according to the invention or of a functional variant thereof and/or of a nucleic acid encoding this or a variant thereof, and/or of an antibody or an antibody fragment directed against a polypeptide useable according to the invention or a functional variant thereof, if appropriate combined or together with suitable additives and/or auxiliaries, for the production of an array attached to a carrier material for analysis in connection with diseases of skin cells and/or of wound healing and/or their pathological disorders.

Processes for preparing such arrays are known, for example, from U.S. Pat. No. 5,744,305 by means of solid-phase chemistry and photolabile protective groups.

The present invention furthermore relates to the use of at least one polypeptide useable according to the invention or a functional variant thereof and/or of a nucleic acid encoding this or a variant thereof, and/or of an antibody or an antibody fragment directed against a polypeptide useable according to the invention or a functional variant thereof, if appropriate combined or together with suitable additives and/or auxiliaries, in the form of an array for analysis in connection with diseases of skin cells, in wound healing and/or their pathological disorders.

For analysis in connection with diseases of skin cells and/or of wound healing and/or their pathological disorders, it is also possible to use, for example, DNA chips and/or protein chips which comprise at least one nucleic acid, at least one polypeptide, and/or at least one antibody or antibody fragment, as described above. DNA chips are disclosed, for example, in U.S. Pat. No. 5,837,832.

The invention will now be further illustrated below with the aid of the figures and examples, without the invention being restricted thereto.

DESCRIPTION OF THE TABLES, FIGURES AND SEQUENCES

Table 1: Tabulation of the differential expression of various genes relevant for wound healing in wounds of 10 weeks old BALB/c mice and in wounds of young (4 weeks of age) and old (12 months) mice, as well as in intact skin and wounds of dexamethasone-treated, badly healing wounds and of control mice.

Table 2: Tabulation of the differential expression of various genes that are relevant for wound healing in intact skin and in wounds of mice with diabetes and of control mice.

Table 3: Tabular survey of polypeptide sequences with unknown biological function that were identified during the analysis of gene expression during wound healing, and their cDNAs and accession numbers or SEQ ID numbers.

Table 4: Tabular survey of the polypeptide sequences with already known and described functions identified in the analysis of gene expression during the wound healing process and their cDNAs and accession numbers or SEQ ID numbers.

Table 5: Tabular survey of the polypeptide sequences with already known and described functions, that were additionally identified in the analysis of gene expression during the wound-healing process, and their cDNAs and accession numbers or SEQ ID numbers.

Table 6: Analysis of the kinetics of wound-relevant genes during wound healing in the mouse by means of "TaqMan analysis".

Table 7: Analysis of the kinetics of wound-relevant genes during wound healing in humans relative to Cyclophilin by means of "TaqMan analysis".

Table 8: Analysis of the expression of genes useable according to the invention in the wound ground and the wound edge relative to intact skin of ulcer patients.

Table 9: Analysis of the expression of genes useable according to the invention in intact skin of healthy persons, as well as in lesional and non-lesional skin of psoriasis patients.

FIG. 1: Autoradiograms of hybridizations of membranes (mouse ATLAS Array, Clontech Laboratories GmbH, Heidelberg) with an identical pattern of applied cDNA fragments using four different samples. All samples were prepared from cDNAs which originated from subtractive hybridizations. A: wound-specific sample (subtraction wound versus intact skin), B: skin-specific sample (subtraction intact skin versus wound), C: sample specific for poorly healing wounds (subtraction wound dexamethasone-treated animals versus wound control animals), D: sample specific for well-healing wounds (subtraction wound control animals versus wound dexamethasone-treated animals). The positions of the TTF-I cDNAs (each loaded twice) are indicated with arrows.

FIG 2: Comparison of the polypeptide sequences of the identified proteins of SW1136 from mouse (murine) (SEQ ID NO: 55) and human (SEQ ID NO: 56). Differences to the human sequence of SW1136 are indicated.

FIG 3: Comparison of the polypeptide sequences of the identified proteins of SW1295 from mouse (murine) (SEQ ID NO: 57) and human (SEQ ID NO: 58). Differences to the human sequence of SW1295 are indicated.

SEQ ID No. 1 to SEQ ID No. 58 and SEQ ID No. 63 to SEQ ID No. 73 and SEQ ID No. 80 to SEQ ID No. 84 show the polypeptide or cDNA sequences useable according to the invention from human or mouse.

SEQ ID No. 59 to SEQ ID No. 62 and SEQ ID No. 74 to SEQ ID No. 79 show DNA sequences of oligonucleotides which were used for the experiments of the present invention.

EXAMPLES

Example 1

Enrichment of Wound-relevant cDNA by Means of Subtractive Hybridization and Identification of TTF-I as Wound-relevant Gene Total RNA was isolated from intact skin and from wound tissue (wounding on the back 1 day before tissue sampling by scissors cut) of BALB/c mice by standard methods (Chomczynski and Sacchi, 1987, Anal. Biochem. 162: 156–159, Chomczynski and Mackey, 1995, Anal. Biochem. 225: 163–164). In order to obtain tissue of mice with poorly healing wounds, BALB/c mice were treated before wounding with dexamethasone (injection of 0.5 mg of dexamethasone in isotonic saline solution per kg of body weight twice per day for 5 days). The RNAs were then transcribed into cDNA with the aid of a reverse transcriptase. The cDNA synthesis was carried out using the "SMART PCR cDNA synthesis kit" from Clontech Laboratories GmbH, Heidelberg, according to the directions of the corresponding manual.

In order to identify those cDNAs which occurred with differing frequency in the cDNA pools, a subtractive hybridization (Diatchenko et al., 1996, Proc. Natl. Acad. Sci. U.S.A. 93: 6025–30) was carried out. This was effected using the "PCR select cDNA subtraction kit" from Clontech Laboratories GmbH, Heidelberg, according to the directions of the corresponding manual, the removal of excess oligonucleotides after the cDNA synthesis being carried out by means of agarose gel electrophoresis. Four cDNA pools were set up, which were enriched for wound-relevant genes, where one pool was enriched for cDNA fragments which are expressed more strongly in the wound tissue in comparison with intact skin ("wound-specific cDNA pool"), one pool was enriched in cDNA fragments which are more strongly expressed in intact skin in comparison with wound tissue ("skin-specific cDNA pool"), one pool was enriched in cDNA fragments which are more strongly expressed in well-healing wounds in comparison with poorly healing wounds ("well healing cDNA pool") and one pool was enriched in cDNA fragments which are more strongly expressed in poorly healing wounds in comparison with well-healing wounds ("poorly healing cDNA pool").

In order to identify those genes which were contained in the cDNA pools relevant to wound healing, the presence of the corresponding cDNAs in the pools was analysed in "reverse Northern blot". Here, the cDNA fragments are immobilized on membranes in the form of arrays of many different cDNAs, and hybridized with a complex mixture of radio-labeled cDNA (Sambrook et al., 1989, Molecular Cloning: A Laboratory Manual, Cold Spring Harbor, Cold Spring Harbor Laboratory Press, New York, Chapter 9 page 9.47 to 9.58 and Chapter 10 page 10.38 to 10.50; Anderson and Young: Quantitative filter hybridisation; in: Nucleic Acids Hybridisation, A Practical Approach, 1985, Eds. Hames and Higgins, IRL Press Ltd.; Oxford, Chapter 4, page 73 to 112). For example, commercially available membranes were used (mouse ATLAS array, Clontech).

For the preparation of suitable hybridization samples, the subtracted cDNA pools were treated with the restriction endonuclease RsaI and purified by means of agarose gel electrophoresis (Sambrook et al., supra, Chapter 6, page 6.1 to 6.35) in order to separate the cDNA synthesis and amplification primer (see manual "PCR-Select cDNA Subtraction Kit", Clontech). The cDNAs were then radio-labeled using the "random hexamer priming" method (Feinberg and Vogelstein, 1983, Anal. Biochem. 132: 6–13) in order to prepare hybridization samples.

The membrane was preincubated in 25 ml of hybridization solution for 30 min at 65° C. (25 mM sodium phosphate, pH=7.5, 125 mM NaCl, 7% SDS). The hybridization sample was denatured at 100° C. for 10 min, then cooled on ice, about 100 CPM ("counts per minute") per ml were added to the hybridization solution and the hybridization was carried out in a hybridization oven for 16 hours at 65° C. The membrane was then washed twice with the hybridization solution without sample at 65° C. for 10 min. The membrane was then washed at 65° C. a number of times for 10 min in each case in wash solution (2.5 mM sodium phosphate, pH=7.5, 12.5 mM NaCl, 0.7% SDS) until it was no longer possible to detect any activity in the solution poured off. The radioactive signals were analyzed using a phosphoimager (BioRad, Quantity One®) (FIG. 1). Those cDNAs were then selected which produced different signal intensities with the various samples. This resulted at the position of TTF-I on the membrane, in a significantly stronger signal intensity with the skin specific cDNA pool in comparison to the wound specific cDNA pool (FIGS. 1A, B). The analysis of the experiment, in which hybridization was performed in parallel with the "poorly healing" cDNA pool and the "well healing" cDNA pool, showed, that the hybridization sample of the "poorly healing" cDNA pool hybridized significantly stronger at the position of TTF-I (FIGS. 1C, D). Therefore, differential expression of TTF-I was observed at two different wound healing states.

Example 2

Verification of the Expression Pattern of TTF-I by Means of "Real-time Quantitative RTPCR"

A verification of the differential expression of the nucleic acids described above as well as the investigation of further wound healing states was carried out by real-time RTPCR in the ABI Prism 7700 sequence detection system (PE Applied Biosystems). The apparatus was equipped with the ABI Prism 7200/7700 SDS software version 1.6.3 (1998). The detection of PCR products was carried out during the amplification of the cDNA with the aid of the stain SYBR Green 1, whose fluorescence is greatly increased by binding to double-stranded DNA (Karlsen et al. 1995, J. Virol. Methods. 55: 153–6; Wittwer et al., 1997, BioTechniques 22: 130–8, Morrison et al., 1998, BioTechniques 24: 954–62). The basis for the quantification is the PCR cycle (threshold cycle, CT value) which is reached when the fluorescence signal exceeds a defined threshold. The analysis is carried out by means of the Δ-CT method (User Bulletin #2, Relative Quantitation of Gene Expression, PE Applied Biosystems, 1997). The abundances of the cDNAs were determined relative to an endogenous reference (GAPDH). The results are shown in Tables 1 and 2.

To obtain tissue from mice with poorly healing wounds, BALB/c mice were treated prior to wounding with dexamethasone (injection of 0.5 mg dexamethasone in isotonic salt solution per kg body weight twice a day for 5 days). To obtain wound tissue from young and old mice, day 1 wounds from 4 weeks and 12 months old BALB/c mice were employed. To obtain wound tissue from mice with diabetes, day 1 wounds of 10 weeks old C57-BL/Ks-db/db/OLa mice were used. Total RNA was obtained from skin and wound tissue as described above and 1 μg of total RNA was subjected to reverse transcription in a thermocycler (GeneAmp PCR system 9700, Perkin Elmer) using the TaqMan reverse transcription reagent kit (Perkin Elmer) according to the recommendations of the manufacturer (SYBR Green PCR and RT-PCR Reagents Protocol, PE Applied Biosystems, 1998). The primers for the amplification of the TTF-I cDNA (TTF-I-Primer 1: CGAGCGCTA-CATTGTCGCT (SEQ ID No. 59), TTF-I-Primer 2: GTCT-TAAATTTGCTTGTGCCCC (SEQ ID No. 60)) and the reference (GAPDH primer 1: ATCAACGGGAAGC-CCATCA (SEQ ID No. 61), GAPDH primer 2: GACAT-ACTCAGCACCGGCCT (SEQ ID No. 62)) were selected with the aid of the Primer Express software for Macintosh PC Version 1.0 (PE Applied Biosystems, P/N 402089, 1998) based on the nucleic acid described above and the known sequence of GAPDH. For the PCR, the SYBR Green PCR Core Reagents Kit (4304886, PE Applied Biosystems) was used. The concentration of the primers in the PCR was initially optimized in the range from 50 nM to 600 nM and the specificity of the PCR was tested by analysis of the length of the amplified products in an agarose gel electrophoresis. The efficiency of the PCR system was then determined by means of a dilution series (User Bulletin #2, Relative Quantitation of Gene Expression, PE Applied Biosystems, 1997). It became apparent that for both cDNAs the efficiency of the amplification was 100%, i.e. at each 1:2 dilution of the cDNA one more cycle was needed in order to exceed the fluorescence threshold value.

For the quantification, each batch of cDNA was amplified from 10 ng of reverse-transcribed total RNA in a total volume of 25 μl. The running conditions for the PCR corresponded to the details of the manufacturer (PE Applied Biosystems, SYBR Green® PCR and RT-PCR Reagents Protocol, 1998). The CT values were analysed and the abundance of TTF-I relative to GAPDH was calculated. On the one hand the decrease of TTF-1 in wounds in comparison to intact skin from control animals as well as of young mice was confirmed (Table 1, compare to FIGS. 1A, B). On the other hand again an increase of expression of TTF-1 was observed in poorly healing wounds of dexamethasone treated mice in comparison to well healing wounds of control animals (Table 1, compare to FIGS. 1B, C). In addition a decrease of TTF-1 could be measured in mice with diabetes (Table 2). Therefore, the regulation of expression of TTF-1 in different wound healing states was verified.

Example 3

Identification of MCP-2 as Gene Relevant for Wounds Using Comparison Counting of Clones in cDNA Libraries Through the Analysis of Restriction Fragment Patterns BALB/c mice were treated with dexamethasone (injection of 0.5 mg dexamethasone per kg body weight twice a day for 5 days) and subsequently wounded to obtain tissue of poorly healing day 1 wounds. The generation of cDNA of the total RNA isolated from the tissue as well as all further steps was performed as described in EP 0 965 642: the cDNA was cloned in defined orientation in a suitable vector and the thus obtained plasmid was transformed into a suitable E. coli strain. 100 E. coli clones respectively were mixed, and the plasmid DNA was isolated. The DNA was separated into three portions and subsequently hydrolized with the restriction endonuclease BglI and labeled with a fluorescent dye. Subsequently each portion was divided into two portions and then hydrolyzed with one of the restriction endonuclease BfaI, DpnI, RsaI, DdeI, AluI and HinfI. The portioned nucleic acids were separated electrophoretically and the pattern of the separated nucleic acids was analyzed. The restriction fragment pattern of clone mixture was compared with the patterns of single cDNA clone analysis and thus the cDNAs were identified. Those nucleic acids were selected which restriction fragment pattern was identified with a different abundance in cDNA pools of poorly healing and well healing wounds. During the analysis of 37000 cDNAs the pattern of MCP-2 (DdeI:196.23±0.3 base pairs; AluI: 67.51±0.5 base pairs; HinfI: 349.88±0.7 base pairs; BfaI: 531.02±2.0 base pairs; DpnI: 245.02±0.3 base pairs; RasI: 254.23±0.3 base pairs) was identified three times in the cDNA pool of poorly healing wounds, while the pattern was not observed in the cDNA pool of well healing wounds.

Example 4

Analysis of the Kinetics of Wound-relevant Genes During Wound Healing in the Mouse by Means of "TaqMan Analysis"

The kinetics of the regulation of the expression of wound-relevant genes during normal wound healing in the mouse was investigated by means of "TaqMan analysis" using the GeneAmp5700 from Applied Biosystems. Normally healing wound biopsies from various time points after wounding and intact skin were obtained from 6 10 week-old BALB/c mice treated with isotonic saline solution by scissors cut as described in Example 1. The RNA was isolated by homogenizing the biopsies in RNAclean buffer (AGS, Heidelberg), to which $\frac{1}{100}$ part by volume of 2-mercaptoethanol had been added using a disperser. The RNA was then extracted by treating with phenol twice by means of acidic phenol saturated with water and extracted in the presence of 1-bromo-3-chloropropane. An isopropanol and an ethanol precipitation were then carried out and the RNA was washed with 75% ethanol. After this, a DNase I digestion of the RNA was carried out. For this, 20 µg of RNA (to 50 µg with DEPC-treated water) were incubated at 37° C. for 20 min with 5.7 µl of transcription buffer (Roche), 1 µl of RNase inhibitor (Roche; 40 U/µl) and 1 µl of DNase I (Roche; 10 U/µl). 1 µl of DNase I was then added again and the mixture was incubated at 37° C. for a further 20 min. The RNA was then treated with phenol, ethanol-precipitated and washed. All above mentioned steps were carried out using DEPC (diethyl pyrocarbonate)-treated solutions or liquids containing no reactive amino groups. cDNA was then prepared from the extracted RNA. This was carried out in the presence of 1×TaqMan RT buffer (Applied Biosystems), 5.5 mM $MgCl_2$ (Perkin Elmer), 500 µM each of dNTPs (Perkin Elmer), 2.5 µM of random hexamers (Perkin Elmer), 1.25 U/µl of MultiScribe Reverse Transcriptase (50 U/µl Perkin Elmer), 0.4 U/µl RNase inhibitor (20 U/µl, Perkin Elmer), 20 µl of RNA (50 ng/µl) and DEPC-treated water (to 100 µl volume). After addition of the RNA and thorough mixing, the solution was divided in 2 0.2 ml wells (50 µl each) and the reverse transcription was carried out in a thermo cycler (10 min at 25° C.; 30 min at 48° C. and 5 min at 95° C.). The cDNA was subsequently quantified by means of quantitative PCR using SYBR green PCR master mixes (Perkin Elmer), a triplicate determination (in each case with target primers and GAPDH primers) being carried out for each cDNA species to be determined. The stock solution for each triplet contained, in a total volume of 57 µl, 37.5 µl of 2×SYBR master mix, 0.75 µl of AmpErase UNG (1 U/µl) and 18.75 µg of DEPC-treated water. Per triplicate determination, 1.5 µl each of forward and reverse primer were added to 57 µl of stock solution in a previously optimized concentration ratio. 60 µl each of the stock solution/primer mixture were mixed with 15 µl of cDNA solution (2 ng/µl) and subdivided into 3 reaction wells. Parallel to this, a stock solution with primers was prepared as a reference for the determination of GAPDH (SEQ ID No. 61 and SEQ ID No. 62), mixed with a further 15 µl of the same cDNA solution and subdivided into 3 reaction wells. In addition, in order to set up a standard curve for the GAPDH-PCR, various cDNA solutions were prepared as a dilution series (4 ng/µl; 2 ng/µl; 1 ng/µl; 0.5 ng/µl and 0.25 ng/µl). 15 µl each of these cDNA solutions were mixed with 60 µl of stock solution/primer mixture for the determination of GAPDH and subdivided into 3 reaction wells. Likewise, a standard curve for the PCR of the genes to be investigated was set up in each case; the same dilutions which were also employed for the GAPDH standard curve were used here. The control used was a PCR batch without cDNA. 15 µl each of DEPC water were added to 60 µl in each case of stock solution/primer mixture of target and GAPDH in each case, mixed and in each case subdivided into 3 reaction wells. The amplification of the batches was carried out in the GeneAmp 5700 (2 min at 50° C.; 10 min at 95° C., followed by 3 cycles of 15 sec at 96° C. and 2 min at 60° C.; then 37 cycles of 15 sec at 95° C. and 1 min at 60° C.). The analysis was carried out by the determination of the relative abundance of each target gene with respect to the GAPDH reference. For this, a standard curve was first set up by plotting the $C_T$ values of the dilution series against the logarithm of the amount of cDNA in the PCR batch (ng of transcribed RNA) and the slope(s) (s) of the straight lines was determined. The efficiency (E) of the PCR then results as follows: $E=10^{-1/s}-1$. The relative abundance (X) of the cDNA species (Y) investigated in relation to GAPDH is then: $X=(1+_{GAPDH})^{C_T(GAPDH)}/(1+E_Y)^{C_T(Y)}$. The numerical values were then standardized by setting the amount of cDNA from intact skin of the 10 week-old BALB/c control animals equal to 1. The relative changes in the target gene expression in various wound healing states are compiled in Table 6. Thus it is clear, for example, in the case of the tyrosine kinase Fer that the expression of skin disease-relevant targets is specifically regulated during wound healing. In this target, even one hour after wounding, a greatly decreased expression of mRNA occurs which lasts during the entire observation period of 14 d. This shows that differential regulation over the entire period of wound healing is essential for the normal course of wound healing.

A similar kinetic, i.e. a reduced expression upon wounding that lasted for days was observed in a plurality of genes, for example for KIAA1247, Cystatin C, SW1136, SW1295, Baf57, TSC-22, Split hand foot deleted 1, Nicotinamid N-Methyl-Transferase, UBC9, tsg101, HMG-14, TAK1 and Golgi-4-transmembrane spanning transporter. This demonstrates that differential regulation of these genes is required over the entire period of wound healing. However complex kinetics have also been observed, for example phospholipase inhibitor exhibited an upregulation of the expression 1 h after wounding as well as 7 and 14 days after wounding. This clearly shows, that the differential expression of phospholipase inhibitor can lead to disorders of the wound healing process directly after wounding as well as during later phases of wound healing and that disorders of the expression and/or activity of phospholipase inhibitor may lead to disorders of the wound healing directly after wounding as well as in later phases of wound healing.

Example 5

Differential Expression of Wound-relevant Genes in Human Wounds

With the aid of the normally healing wounds, it should now be investigated whether a differential regulation of the expression of the genes identified as wound-relevant verified in Example 4 can also be observed in humans. For this, 4 mm biopsies of intact skin were taken from 6 patients as described above, and also 6 mm biopsies from the same patients at the time points T=1 h, 1 d, 5 d and 14 d. The biopsies of a given time point were pooled and the cDNA was isolated as described above. Then the quantification was done by means of TaqMan analysis as described above, except that the abundance of the target species to be determined was determined relative to cyclophilin (EMBL: Y00052). The primers used for this are cyclophilin primer 1: TCTTAACCAC CAGATCATTC CTTCT (SEQ ID No. 78) and cyclophilin primer 2: GGATACTGCG AGCAAATGGG (SEQ ID No. 79). The analysis of the experiment is shown in Table 7. In the case of CCR-1 (CCR-1 Primer 1: CCCAATGGGA ATTCACTCAC C (SEQ ID Nr. 76); CCR-1 Primer 2: GCTTCCACTC TCGTAGGCTT TC (SEQ ID No. 77)), a strong increase in CCR-1 expression until 24 h after wounding followed by a slow decrease in CCR-1 expression was observed in human. This is fully consistent with the kinetics of CCR-1 expression in murine wound biopsies (Table 6). Also, it was possible to show, for example, in the case of the Golgi 4 transmembrane spanning transporter that differential regulation of expression during wound healing can be detected both in the mouse and in man. Thereby, it was thus possible to verify the relevance of the target to wound healing and skin diseases. Also the other genes analyzed showed a differential regulation upon wounding. Thus it was possible to demonstrate that the targets are relevant for wound healing and for skin disorders. The genes showed complex kinetics of expression with transient changes, such as for example in the case of Eps8, Phospholipase Inhibitor, TSC-22, Cathepsin C and HMG-14 as well as a steady increase in expression spanning the time of investigation such as in the case of KIAA1247 and Cystatin C. This demonstrates, that the precise regulation of the expression and/or activity of the targets is essential for the normal course of the wound healing process both in mice and humans.

Example 6

Differential Expression of Wound-relevant Genes in Human Ulcers

In order to show that the genes identified as wound-relevant are differentially regulated not only in normally proceeding wound healing but also in the case of a wound-healing disorder, biopsies from patients having chronic venous ulcers were taken at the same time from intact skin and from the wound ground and the wound edge and were investigated for expression of the target genes. From each group (intact skin, wound edge, wound ground), the biopsies of 6 subjects in each case were pooled. RNA was isolated from all biopsies as described in Example 4 transcribed into cDNA. The quantification of wound healing-relevant cDNAs was carried out also as described in Example 5, the amount of cyclophilin mRNA being used for the calculation of the relative amount of the target gene cDNA. The results of the experiments are compiled in Table 8. Thus, in the case of KIAA 1247, for example, a dysregulation of the expression in the ulcers was found in comparison to the normally healing wound (Table 7): while in the normally healing wound a steady increase in the KIAA1247 was observed, a markedly reduced expression was found at the wound edge. This shows that the differential expression of KIAA1247 is essential not only for wound healing, but that dysregulations can lead to severe wound-healing disorders. The experiment illustrates that KIAA1247 can be used for the diagnosis, prevention and/or treatment of wound-healing disorders and/or skin diseases.

Example 7

Differential Regulation of Genes Useable According to the Invention in Lesional and Non-lesional Skin of Psoriasis Patients in Comparison with Intact Skin of Healthy Patients It should now be verified with the aid of psoriasis patients that genes useable according to the invention play an important part not only in wound healing and wound-healing disorders but also in other skin diseases. For this, 4 mm punch biopsies both of lesional and non-lesional skin were taken from psoriasis patients as described in Example 5. As a control, biopsies of intact skin were taken from healthy subjects. The isolation of the mRNA from the individual biopsies was carried out by embedding the biopsies in tissue freezing medium (Jung), the reduction of the biopsy into pieces using a microtome and the subsequent mRNA isolation by means of Dynabeads-Oligo dT (Dynal). The hackled biopsies were first suspended in lysis-buffer and then homogenized using the Polytron. In order to fragment the genomic DNA, the solution is centrifuged through Qia-Shredder columns and additionally sheared a number of times in a syringe with a needle. The Dynabeads were pretreated according to the instructions of the manufacturer and mixed with the lysis homogenate (250 $\mu$l of the stock suspension), incubated and washed (final volume 250 $\mu$l). The suspension was then divided into one portion each of 240 $\mu$l and of 10 $\mu$l (as a control). For the first strand synthesis, the following components were mixed: 20 $\mu$l of 10×TaqMan RT buffer, 44 $\mu$l of 25 mM MgCl$_2$, 40 $\mu$l of dNTP mix (2.5 mM/dNTP), 87 $\mu$l of DEPC-H$_2$O, 4 $\mu$l of RNase inhibitor (20 U/$\mu$l) and 5 $\mu$l of MultiScribe transcriptase (50 U/µl). 195 µl of the reaction mix were then added to the 240 µl batch and 20 µl to the control batch, mixed and incubated at 48° C. for 45 min. The Dyna-beads were then pelleted in a magnetic particle collector and the supernatant was withdrawn. 20 µl of Tris-HCl buffer were then added and the suspension was incubated at 95° C. for 1 min. The Dynabeads were immediately pelleted in a magnetic particle collector and the mRNA in the supernatant was withdrawn. The cDNA/Dynabeads were then washed 3× with TE buffer. For the second strand synthesis, the cDNA/Dynabeads were washed 2× in 1×EcoPol buffer and a solution of the following components was added: 23 µl of 10×EcoPol buffer; 4.6 µl of dNTP mix (25 mM/dNTP); 11.5 µl of random hexamers; 118.7 µl of DEPC-$H_2O$. The suspension was mixed briefly with the aid of a vortexer and 9.2 µl of Klenow fragment (5 U/µl) were then added. 200 µl of this solution were added to the batch, 20 µl to the control batch, and the suspensions were incubated at 37° C. for 1 h. The DNA was then melted at 94° C. for 1 min and the Dynabeads were pelleted in a magnetic particle collector. The supernatant was transferred to a new reaction vessel and the enzyme was inactivated at 75° C. for 10 min. The sense DNA strands contained in the supernatant were then employed for the TaqMan analysis.

The TaqMan analysis was carried out as described in Example 5, the amount of GAPDH (hGAPDH-Primer 1: CCTCCCCTCTTCAAGGGTCTA (SEQ ID No. 74); hGAPDH-Primer 2: AGGAGTAAGACCCCTGGACCA (SEQ ID Nr. 75) being used for the calculation of the relative abundance of the respective mRNA species in the individual biopsies. Since a far greater amount of total mRNA is isolatable from the skin biopsies of psoriasis patients, in particular from lesional skin, than from intact skin of healthy subjects, a standardization to identical amounts of mRNA is necessary, the amount of GAPDH mRNA being assumed as a housekeeping gene as a marker for the amount of total mRNA. A total of 4 biopsies of intact skin of healthy subjects were analyzed, and also 8 biopsies in each case of lesional and non-lesional skin from psoriasis patients. The abundances of target gene cDNA in the individual groups (intact skin, lesional skin, non-lesional skin) were then standardized to the total amount of the abundances of the cDNAs measured on a microtiter plate. These analyses were carried out for Eps8 (EMBL: U12535); KIAA1247 (GB: AB033073; WO 99/63088) and MASPIN (EMBL: U04313); the average values of the results are compiled in Table 9. It is clear that in both genes useable according to the invention a clear and statistically significant ($p<0.05$, paired t-test) reduced regulation in lesional skin of 8 psoriasis patients is observed compared with non-pathological skin of the same patients in each case. This illustrates that a dysregulation of these genes can lead to skin diseases and that the genes useable according to the invention are therefore suitable for the prevention and/or treatment and/or diagnosis of skin diseases. In the case of psoriasis patients, the aim is to modulate, preferably to activate, the expression and/or activity of KIAA1247 and/or Eps8 and/or MASPIN. Modulation in the skin, in particular the lesional skin, of the psoriasis patients is preferred here.

As exemplified by KIAA1247, the relationship between dysregulation of the gene and psoriatic disease should now be demonstrated. Here, the conductivity of the skin (a measure of the moisture of the skin) was determined as a measurement parameter and compared with the KIAA1247 expression of the gene in this part of the skin. The conductivity of the skin was determined using a corneometer according to the instructions of the manufacturer (Courage and Khazaka Electronics). It was found here that a statistically significant positive correlation ($p=0.000659$, Pearson Product Moment Correlation) is observed between conductivity of the biopsy investigated in each case and the KIAA1247 expression: in very dry biopsies of lesional psoriatic skin having a low conductivity, a correspondingly low KIAA1247 mRNA expression was measured, while in more moist skin, i.e. in non-pathogenic skin of the psoriatic patients and in intact skin of healthy subjects, a markedly stronger KIAA1247 expression is detectable. This verifies the relevance of KIAA1247 expression for the pathogenesis of skin diseases.

It will be apparent to those skilled in the art that various modifications and variations can be made to the compositions and processes of this invention. Thus, it is intended that the present invention cover such modifications and variations, provided they come within the scope of the appended claims and their equivalents.

Priority application DE 10030149.5-41, filed Jun. 20, 2000, and U.S. 60/222,081, filed Aug. 1, 2000 including the specification, drawings, claims and abstract, is hereby incorporated by reference. All publications cited herein are incorporated in their entireties by reference.

TABLE 1

Genes differentially expressed

|  | Intact skin control animals | Wound control animals | Intact skin dexamethasone | Wound dexamethasone |
| --- | --- | --- | --- | --- |
| TTF-1 | 1.00 | 0.81 | 1.00 | 1.31 |
| CCR-1 | 1.00 | 31.84 | 0.45 | 76.74 |
| MASPIN | 1.00 | 0.76 | 1.00 | 1.03 |
| B-Raf | 1.00 | 0.77 | 0.77 | 0.71 |
| Prothymosin alpha | 1.00 | 0.97 | 0.91 | 1.90 |
| Eps8 | 1.00 | 0.70 | 0.60 | 0.20 |
| KIAA1247 | 1.00 | 0.30 | 0.90 | 0.20 |
| Cystatin C | 1.00 | 0.77 | 0.74 | 2.21 |
| SW1136 | 1.00 | 0.83 | 0.58 | 1.43 |
| SW1295 | 1.00 | 0.80 | 0.55 | 4.39 |
| BAF57 | 1.00 | 0.98 | 0.93 | 0.54 |
| EAT/MCL-1 | 1.00 | 1.99 | 0.79 | 2.55 |
| Phospholipase Inhibitor | 1.00 | 0.19 | 1.35 | 0.23 |
| TSC-22 | 1.00 | 0.60 | 0.56 | 2.31 |
| Split hand/foot deleted 1 | 1.00 | 1.89 | 0.98 | 10.53 |
| Gamma Sarcoglycan | 1.00 | 0.47 | 1.51 | 0.46 |
| Nicotinamid N-Methyltransferase | 1.00 | 0.93 | 1.00 | 2.15 |
| Golgi 4-Transmembrane spanning transporter | 1.00 | 0.57 | 0.28 | 2.00 |
| UBC9 | 1.00 | 0.95 | 1.06 | 1.91 |
| Cathepsin C | 1.00 | 1.68 | 1.58 | 1.09 |
| tsg101 | 1.00 | 0.94 | 1.03 | 2.06 |
| DAD-1 | 1.00 | 1.07 | 0.93 | 1.93 |
| HMG-14 | 1.00 | 0.61 | 0.43 | 2.11 |
| TAK1 | 1.00 | 0.64 | 0.90 | 0.46 |
| IL-5Ralpha | 1.00 | 5.89 | 0.84 | 1.12 |
| Fer | 1.00 | 0.72 | 0.46 | 0.33 |
|  | Intact skin young mice | Wound young mice | Intact skin old mice | Wound old mice |
| TTF-1 | 1.87 | 0.78 | 0.84 | 0.65 |
| CCR-1 | 1.07 | 22.22 | 0.84 | 24.18 |
| MASPIN | 2.00 | 0.39 | 1.18 | 0.45 |
| B-Raf | 1.29 | 0.63 | 0.61 | 0.70 |
| Prothymosin alpha | 1.36 | 0.67 | 0.78 | 0.48 |
| Eps8 | 0.80 | 0.40 | 0.60 | 0.60 |
| KIAA1247 | 2.20 | 0.70 | 1.00 | 0.20 |
| Cystatin C | 0.76 | 0.37 | 0.91 | 0.26 |

TABLE 1-continued

Genes differentially expressed

| | | | | |
|---|---|---|---|---|
| SW1136 | 1.05 | 0.33 | 0.44 | 0.26 |
| SW1295 | 0.73 | 0.50 | 0.70 | 0.35 |
| BAF57 | 1.82 | 0.54 | 0.70 | 0.92 |
| EAT/MCL-1 | 2.67 | 1.79 | 1.42 | 1.12 |
| Phospholipase Inhibitor | 6.03 | 0.11 | 0.59 | 0.23 |
| TSC-22 | 1.23 | 0.42 | 0.42 | 0.55 |
| Split hand/foot deleted 1 | 1.48 | 0.94 | 0.83 | 0.55 |
| Gamma Sarcoglycan | 0.43 | 0.48 | 0.44 | 0.14 |
| Nicotinamid N-Methyltransferase | 1.14 | 0.86 | 0.92 | 0.78 |
| Golgi 4-Transmembrane spanning transporter | 0.53 | 0.26 | 0.27 | 0.11 |
| UBC9 | 1.76 | 0.94 | 1.40 | 0.64 |
| Cathepsin C | 2.20 | 1.61 | 0.75 | 0.89 |
| tsg101 | 1.80 | 0.92 | 0.96 | 0.48 |
| DAD-1 | 1.32 | 1.04 | 0.87 | 0.61 |
| HMG-14 | 1.03 | 0.40 | 0.50 | 0.20 |
| TAK1 | 1.75 | 0.74 | 0.93 | 0.74 |
| IL-5Ralpha | 1.38 | 1.66 | 2.61 | 1.74 |
| Fer | 0.48 | 0.22 | 0.40 | 0.37 |

TABLE 2

| Genes differentially expressed | Intact skin control animals | Wound control animals | Intact skin diabetic mice | Wound diabetic mice |
|---|---|---|---|---|
| TTF-1 | 1.00 | 0.61 | 1.57 | 0.54 |
| CCR-1 | 1.00 | 23.51 | 2.26 | 20.66 |
| MASPIN | 1.00 | 0.30 | 1.54 | 0.38 |
| B-Raf | 1.00 | 1.25 | 1.66 | 1.05 |
| Prothymosin alpha | 1.00 | 0.58 | 1.26 | 0.83 |
| Eps8 | 1.00 | 2.50 | 0.70 | 1.40 |
| KIAA1247 | 1.00 | 0.30 | 1.50 | 0.50 |
| Cystatin C | 1.00 | 0.49 | 1.35 | 0.57 |
| SW1136 | 1.00 | 0.31 | 1.15 | 0.48 |
| SW1295 | 1.00 | 0.39 | 1.00 | 0.65 |
| BAF57 | 1.00 | 0.45 | 1.15 | 0.51 |
| EAT/MCL-1 | 1.00 | 1.36 | 1.54 | 1.56 |
| Phospholipase Inhibitor | 1.00 | 0.31 | 1.14 | 0.28 |
| TSC-22 | 1.00 | 0.43 | 1.70 | 0.60 |
| Split hand/foot deleted 1 | 1.00 | 0.41 | 0.35 | 0.79 |
| Gamma Sarcoglycan | 1.00 | 0.04 | 0.33 | 0.08 |
| Nicotinamid N-Methyltransferase | 1.00 | 0.77 | 3.26 | 1.88 |
| Golgi 4-Transmembrane spanning transporter | 1.00 | 0.22 | 0.35 | 0.40 |
| UBC9 | 1.00 | 0.63 | 1.66 | 0.63 |
| Cathepsin C | 1.00 | 0.89 | 0.58 | 0.34 |
| tsg101 | 1.00 | 0.64 | 1.53 | 0.53 |
| DAD-1 | 1.00 | 0.96 | 1.84 | 1.43 |
| HMG-14 | 1.00 | 0.31 | 1.56 | 0.58 |
| TAK1 | 1.00 | 0.35 | 1.30 | 0.46 |
| Fer | 1.00 | 0.27 | 1.35 | 0.31 |

TABLE 3

| No. | NAME | PROTEIN-MOUSE* | Seq ID No. | PROTEIN-HUMAN* | Seq ID No. | CDNA-MOUSE* | CDNA-HUMAN* |
|---|---|---|---|---|---|---|---|
| 1. | SW1136 | Seq ID Nr. 55 | 55 | Seq ID Nr. 56 | 56 | Seq ID Nr. 50 | Seq ID Nr. 51 |
| 2. | SW1295 | Seq ID Nr. 57 | 57 | trembl: Q9Y6H1 | 58 | Seq ID Nr. 52 | EMBL: AF078845 |

*pir: PIR-databank
EMBL: EMBL-databank
trembl: translated EMBL-databank

TABLE 4

| No. | NAME | PROTEIN-MOUSE* | Seq ID No. | PROTEIN-HUMAN* | Seq ID No. | CDNA-MOUSE* | CDNA-HUMAN* |
|---|---|---|---|---|---|---|---|
| 3. | tumor susceptibility gene 101 (TSG101) | SP: Q61187 | 1 | SP: Q99816 | 2 | EMBL: U52945 | EMBL: U82130 |
| 4. | MASPIN | SP: P70124 | 3 | SP: P36952 | 4 | EMBL: U54705 | EMBL: U04313 |
| 5. | Transcription Termination Factor 1 | SP: Q62187 | 5 | SP: Q15361 | 6 | EMBL: X83974 | EMBL: X83973 |
| 6. | B-Raf | SP: P28028 | 7 | SP: P15056 | 8 | GB: M64429 | GB: M95712 |
| 7. | Prothymosin alpha | SP: P26350 | 9 | SP: P06454 | 10 | GB: X56135 | GB: M14630 |
| 8. | Golgi 4-transmembrane spanning transporter (MTP) | SP: Q60961 | 11 | SP: Q15012 | 12 | EMBL: U34259 | EMBL: D14696 |
| 9. | CCR-1 | SP: P51675 | 13 | SP: P32246 | 14 | EMBL: U29678 | EMBL: L09230 |
| 10. | HMG-14 | SP: P18608 | 15 | SP: P05114 | 16 | EMBL: X53476 | EMBL: J02621 |
| 11. | Split hand/Foot deleted 1 | GP: NP_033195 | 17 | SP: Q13437 | 18 | EMBL: U41626 | EMBL: U41515 |
| 12. | TAK1 | SP: P49117 | 19 | SP: P49116 | 20 | EMBL: U11688 | EMBL: U10990 |
| 13. | BAF57 | trembl: O54941 | 31 | trembl: O43539 | 32 | GB: AF035263 | GB: AF035262 |
| 14. | EPS8 | SP: Q08509 | 33 | SP: Q12929 | 34 | EMBL: L21671 | EMBL: U12535 |
| 15. | KIAA1247 | Seq ID Nr. 36 | 35 | GP: BAA86561 | 36 | Seq ID 53 | GB: AB033073 |
| 16. | Phospholipase Inhibitor | Seq ID Nr. 38 | 37 | U.S. Pat. No. 5,948,626 | 38 | Seq ID 54 | U.S. Pat. No. 5,948,626 |
| 17. | EAT/MCL-1 | trembl: P97287 | 39 | SP: Q07820 | 40 | EMBL: U35623 | EMBL: L08246 |
| 18. | TSC-22 | SP: Q00992 | 41 | SP: Q15714 | 42 | EMBL: X62940 | EMBL: U35048 |
| 19. | Gamma-Sarcoglycan | trembl: P82348 | 43 | trembl: Q13326 | 44 | EMBL: AB024922 | EMBL: U34976 |
| 20. | Cystatin C | SP: P21460 | 46 | SP: P01034 | 47 | EMBL: M59470 | EMBL: X05607 |

TABLE 4-continued

| No. | NAME | PROTEIN-MOUSE* | Seq ID No. | PROTEIN-HUMAN* | Seq ID No. | CDNA-MOUSE* | CDNA-HUMAN* |
|---|---|---|---|---|---|---|---|
| 21. | Fer | trembl: P70451 | 63 | SP: P16591 | 64 | EMBL: U76762 | EMBL: J03358 |
| 22. | MRP-3 | SP: P27784 | 65 | SP: P55773 | 66 | EMBL: M58004 | EMBL: U85767 |
| 23. | NNMT | trembl: O55239 | 67 | SP: P40261 | 68 | EMBL: U86105 | EMBL: U08021 |
| 24. | UBC9 | SP: P50550 | 69 | SP: P50550 | 70 | EMBL: X99739 | EMBL: X96427 |

*pir: PIR-databank
EMBL: EMBL-databank
trembl: translated EMBL-databank
GB: GeneBank nucleic acids
GP: GeneBank polypeptide

TABLE 5

| No. | NAME | PROTEIN-MOUSE* | Seq ID No. | PROTEIN-HUMAN* | Seq ID No. | CDNA-MOUSE* | CDNA-HUMAN* |
|---|---|---|---|---|---|---|---|
| 25. | MCP-3 | SP: Q03366 | 21 | SP: P80098 | 22 | EMBL: X70058 | EMBL: X71087 |
| 26. | IL-5Ralpha | SP: P21183 | 23 | SP: Q01344 | 24 | EMBL: D90205 | EMBL: M96652 |
| 27. | DAD-1 | SP: P46966 | 25 | SP: P46966 | 26 | EMBL: U22107 | EMBL: D15057 |
| 29. | MCP-2 | trembl: Q9Z121 | 29 | SP: P80075 | 30 | GB: AB023418 | GB: X99886 |
| 30. | Cathepsin C | SP: P97821 | 72 | SP: P53634 | 73 | GB: U89269 | GB: X87212 |

*pir: PIR-databank
EMBL: EMBL-databank
GB: GeneBank nucleic acid
GP: GeneBank polypeptide
trembl: translated EMBL-databank

TABLE 6

| Differentially expressed genes | Intakt skin | Wound 1 h | Wound 7 h | Wound 15 h | Wound 24 h | Wound 3 d | Wound 5 d | Wound 7 d | Wound 14 d |
|---|---|---|---|---|---|---|---|---|---|
| B-Raf | 1.00 | 1.30 | 0.79 | 0.89 | 0.87 | 0.94 | 1.21 | 0.72 | 0.93 |
| KIAA1247 | 1.00 | 0.67 | 0.53 | 0.30 | 0.31 | 0.44 | 0.67 | 1.11 | 0.97 |
| Cystatin C | 1.00 | 0.78 | 0.69 | 0.69 | 0.60 | 0.68 | 0.88 | 1.05 | 0.89 |
| SW1136 | 1.00 | 0.48 | 0.36 | 0.15 | 0.15 | 0.23 | 0.31 | 0.33 | 0.20 |
| SW1295 | 1.00 | 0.43 | 0.33 | 0.28 | 0.22 | 0.27 | 0.35 | 0.66 | 0.44 |
| BAF57 | 1.00 | 0.76 | 0.57 | 0.54 | 0.42 | 0.67 | 0.93 | 1.19 | 0.94 |
| EAT/MCL-1 | 1.00 | 0.58 | 0.81 | 1.08 | 0.75 | 0.85 | 1.16 | 0.66 | 0.66 |
| Phospholipase Inhibitor | 1.00 | 14.47 | 1.00 | 0.23 | 0.88 | 1.34 | 1.49 | 3.67 | 21.93 |
| TSC-22 | 1.00 | 0.68 | 0.66 | 0.43 | 0.40 | 0.43 | 0.70 | 0.88 | 0.95 |
| Split hand/foot deleted 1 | 1.00 | 0.57 | 0.40 | 0.42 | 0.43 | 0.53 | 0.67 | 0.62 | 0.66 |
| Nicotinamide N-Methyl-transferase | 1.00 | 0.36 | 0.60 | 0.46 | 0.43 | 0.71 | 0.43 | 0.80 | 0.62 |
| Golgi 4-Transmembrane spanning transporter | 1.00 | 0.67 | 0.69 | 0.34 | 0.26 | 0.33 | 0.46 | 0.50 | 0.48 |
| UBC9 | 1.00 | 0.72 | 0.68 | 0.49 | 0.51 | 0.81 | 0.87 | 0.95 | 1.18 |
| Cathepsin C | 1.00 | 0.83 | 0.29 | 0.26 | 1.54 | 0.81 | 1.29 | 1.07 | 3.88 |
| tsg101 | 1.00 | 0.71 | 0.51 | 0.45 | 0.33 | 0.62 | 0.53 | 0.66 | 0.83 |
| DAD-1 | 1.00 | 0.84 | 0.76 | 0.74 | 0.84 | 1.07 | 1.10 | 1.36 | 1.18 |
| HMG-14 | 1.00 | 0.55 | 0.31 | 0.29 | 0.33 | 0.46 | 0.49 | 0.45 | 0.62 |
| TAK1 | 1.00 | 0.49 | 0.62 | 0.28 | 0.39 | 0.54 | 0.64 | 0.71 | 0.65 |
| Fer | 1.00 | 0.17 | 0.15 | 0.09 | 0.13 | 0.17 | 0.22 | 0.25 | 0.08 |
| EPS8 | 1.00 | 0.60 | 1.10 | 1.00 | 0.70 | 0.70 | 1.00 | 0.70 | 0.90 |
| CCR-1 | 1.00 | 1.40 | 5.90 | 19.00 | 17.00 | 16.00 | 13.00 | 5.50 | 3.70 |
| MASPIN | 1.00 | 0.60 | 0.50 | 0.30 | 0.30 | 0.30 | 0.40 | 0.50 | 0.80 |
| TTF-1 | 1.00 | 0.80 | 0.60 | 0.50 | 0.40 | 0.50 | 0.60 | 0.60 | 0.90 |

TABLE 7

| cDNA expression in human biopsies relative to Cyclophilin | Intact skin | wound 1 h | wound 24 h | wound 5 d | wound 14 d |
|---|---|---|---|---|---|
| Eps8 | 1.00 | 1.41 | 0.74 | 1.3 | 1.29 |
| KIAA1247 | 1.00 | 0.92 | 1.22 | 1.02 | 1.58 |
| Phospholipase Inhibitor | 1.00 | 1.24 | 0.64 | 0.57 | 0.85 |
| Cystatin C | 1.00 | 0.86 | 1.27 | 1.79 | 2.33 |
| TSC-22 | 1.00 | 1.34 | 0.91 | 1.29 | 1.98 |
| Golgi 4-Transmembrane spanning transporter | 1.00 | 0.69 | 0.63 | 0.59 | 0.72 |
| Cathepsin C | 1.00 | 0.86 | 2.96 | 4.09 | 2.67 |
| HMG-14 | 1.00 | 1.87 | 0.56 | 0.98 | 0.87 |
| Nicotinamide N-Methyltransferase | 1.00 | 1.74 | 6.20 | 9.74 | 5.15 |
| UBC9 | 1.00 | 0.98 | 1.39 | 1.43 | 1.45 |
| CCR-1 | 1.00 | 1.28 | 10.56 | 7.78 | 5.66 |
| tsg101 | 1.00 | 1.09 | 1.07 | 1.24 | 1.27 |
| MASPIN | 1.00 | 1.62 | 0.38 | 1.11 | 0.61 |
| TTF-1 | 1.00 | 0.55 | 0.95 | 0.74 | 1.45 |
| B-Raf | 1.00 | 1.82 | 0.89 | 1.45 | 1.30 |
| DAD-1 | 1.00 | 0.66 | 1.47 | 1.61 | 1.46 |
| Fer | 1.00 | 8.07 | 0.83 | 3.35 | 5.06 |
| Split hand/foot deleted 1 | 1.00 | 0.98 | 0.79 | 1.31 | 1.20 |
| Gamma Sarcoglycan | 1.00 | 1.13 | 0.29 | 0.67 | 0.89 |
| TAK1 | 1.00 | 1.08 | 0.89 | 1.37 | 1.56 |

TABLE 8

| Gen useable according to the invention | Intact skin of ulcer patients | wound edge of ulcer patients | wound ground of ulcer patients |
|---|---|---|---|
| Eps8 | 1.00 | 0.88 | 0.89 |
| KIAA1247 | 1.00 | 0.38 | 1.1 |
| Phospholipase Inhibitor (Variant SEQ ID Nr. 45) | 1.00 | 0.54 | 0.48 |
| Phospholipase Inhibitor (Variant SEQ ID Nr. 81) | 1.00 | 1.54 | 1.18 |
| Cystatin C | 1.00 | 0.66 | 0.52 |
| TSC-22 | 1.00 | 0.64 | 0.70 |
| Golgi 4-Transmembrane spanning transporter | 1.00 | 1.15 | 0.85 |
| Cathepsin C | 1.00 | 0.6 | 1.07 |
| HMG-14 | 1.00 | 1.64 | 0.87 |
| Nicotinamid N-Methyltransferase | 1.00 | 2.28 | 1.49 |
| UBC9 | 1.00 | 0.72 | 0.74 |
| CCR-1 | 1.00 | 6.00 | 16.80 |
| tsg101 | 1.00 | 0.54 | 0.50 |
| MASPIN | 1.00 | 0.29 | 0.04 |
| TTF-1 | 1.00 | 0.40 | 0.60 |
| B-Raf | 1.00 | 0.76 | 0.31 |
| DAD-1 | 1.00 | 0.97 | 0.65 |
| Fer | 1.00 | 0.80 | 0.26 |
| Split hand/foot deleted 1 | 1.00 | 0.19 | 0.16 |
| Gamma Sarcoglycan | 1.00 | 0.10 | 0.05 |
| TAK1 | 1.00 | 0.27 | 0.41 |

TABLE 9

| | standardized relative amount | | |
|---|---|---|---|
| Gen useable according to the invention | Intact healthy skin | Lesional skin of psoriasis patients | Non-lesional skin of psoriasis patients |
| KIAA1247 | 9.69E−02 | 6.23E−02 | 1.39E−01 |
| Eps8 | 1.10E−01 | 5.36E−02 | 1.41E−01 |
| MASPIN | 7.55E−02 | 8.60E−02 | 1.26E−01 |
| | | | 1.26E−01 |

What is claimed is:

1. A method of diagnosing a skin disorder in a patient, said method comprising determining, in a sample from said patient, the level of a nucleic acid encoding a polypeptide comprising the amino acid sequence of SEQ ID NO: 34, wherein a level of said nucleic acid in said sample from said patient that differs from the level in a control sample indicates that said patient has a skin disorder selected from the group consisting of psoriasis, eczema, acne, Urticaria, disorders of pigmentation of the skin, senile skin, and disorders of hair growth and hair metabolism.

2. A method of diagnosing a wound healing disorder in a patient, said method comprising determining, in a sample from said patient, the level of a nucleic acid encoding a polypeptide comprising the amino acid sequence of SEQ ID NO: 34, wherein a level of said nucleic acid in said sample from said patient that differs from the level in a control sample indicates that said patient has a wound healing disorder selected from the group consisting of wounds of patients suffering from diabetes, wounds of patients suffering from alcoholism, wounds infected with organisms, wounds infected with viruses, ischemic wounds, wounds of patients suffering from arterial disorders, wounds of patients suffering from venous insufficiency, wounds of patients suffering from scars.

3. The method of claim 1 or 2, wherein said sample is a skin biopsy.

* * * * *

UNITED STATES PATENT AND TRADEMARK OFFICE
CERTIFICATE OF CORRECTION

PATENT NO.    : 6,586,185 B2
DATED         : July 1, 2003
INVENTOR(S)   : Wolf et al.

It is certified that error appears in the above-identified patent and that said Letters Patent is hereby corrected as shown below:

Title page,
Item [56], References Cited, FOREIGN PATENT DOCUMENTS, "EP 3724524581" should be -- DE 3724524581 --.

Column 5,
Line 20, "protooncogen" should be -- protooncogene --.
Line 40, "GOGLI" should be -- GOLGI --.

Column 6,
Line 44, "signales" should be -- signals --.

Column 7,
Line 4, "disclosedin" should be -- gdisclosed in --.
Line 42, "gycoprotein" should be -- glycoprotein --.
Line 56, "Cystein" should be -- Cysteine --.

Column 8,
Line 8, "proto-oncogen" should be -- proto-oncogene --.
Line 34, "nicotineamide" should be -- nicotinamide --.

Column 10,
Line 6, "chemoatractant" should be -- chemoattractant --.

Column 13,
Line 28, "funtional" should be  functional --.

Column 15,
Line 26, "Oligonuclecotides" should be -- Oligonucleotides --.

Column 27,
Line 30, "annalysis" should be -- analysis --.

UNITED STATES PATENT AND TRADEMARK OFFICE
CERTIFICATE OF CORRECTION

PATENT NO.   : 6,586,185 B2
DATED        : July 1, 2003
INVENTOR(S)  : Wolf et al.

It is certified that error appears in the above-identified patent and that said Letters Patent is hereby corrected as shown below:

Column 28,
Line 21, "hybdridization" should be -- hybridization --.

Signed and Sealed this

Tenth Day of August, 2004

JON W. DUDAS
*Acting Director of the United States Patent and Trademark Office*

SEQUENCE LISTING

```
<160> NUMBER OF SEQ ID NOS: 84

<210> SEQ ID NO 1
<211> LENGTH: 391
<212> TYPE: PRT
<213> ORGANISM: Mus musculus

<400> SEQUENCE: 1

Met Ala Val Ser Glu Ser Gln Leu Lys Lys Met Met Ser Lys Tyr Lys
1               5                   10                  15

Tyr Arg Asp Leu Thr Val Arg Gln Thr Val Asn Val Ile Ala Met Tyr
            20                  25                  30

Lys Asp Leu Lys Pro Val Leu Asp Ser Tyr Val Phe Asn Asp Gly Ser
        35                  40                  45

Ser Arg Glu Leu Val Asn Leu Thr Gly Thr Ile Pro Val Arg Tyr Arg
    50                  55                  60

Gly Asn Ile Tyr Asn Ile Pro Ile Cys Leu Trp Leu Leu Asp Thr Tyr
```

-continued

```
                65                  70                  75                  80
Pro Tyr Asn Pro Pro Ile Cys Phe Val Lys Pro Thr Ser Ser Met Thr
                    85                  90                  95

Ile Lys Thr Gly Lys His Val Asp Ala Asn Gly Lys Ile Tyr Leu Pro
                100                 105                 110

Tyr Leu His Asp Trp Lys His Pro Arg Ser Glu Leu Leu Glu Leu Ile
                115                 120                 125

Gln Ile Met Ile Val Ile Phe Gly Glu Glu Pro Pro Val Phe Ser Arg
                130                 135                 140

Pro Thr Val Ser Ala Ser Tyr Pro Pro Tyr Thr Ala Thr Gly Pro Pro
145                 150                 155                 160

Asn Thr Ser Tyr Met Pro Gly Met Pro Ser Gly Ile Ser Ala Tyr Pro
                165                 170                 175

Ser Gly Tyr Pro Pro Asn Pro Ser Gly Tyr Pro Gly Cys Pro Tyr Pro
                180                 185                 190

Pro Ala Gly Pro Tyr Pro Ala Thr Thr Ser Ser Gln Tyr Pro Ser Gln
                195                 200                 205

Pro Pro Val Thr Thr Val Gly Pro Ser Arg Asp Gly Thr Ile Ser Glu
                210                 215                 220

Asp Thr Ile Arg Ala Ser Leu Ile Ser Ala Val Ser Asp Lys Leu Arg
225                 230                 235                 240

Trp Arg Met Lys Glu Glu Met Asp Gly Ala Gln Ala Glu Leu Asn Ala
                245                 250                 255

Leu Lys Arg Thr Glu Glu Asp Leu Lys Lys Gly His Gln Lys Leu Glu
                260                 265                 270

Glu Met Val Thr Arg Leu Asp Gln Glu Val Ala Glu Val Asp Lys Asn
                275                 280                 285

Ile Glu Leu Leu Lys Lys Lys Asp Glu Glu Leu Ser Ser Ala Leu Glu
                290                 295                 300

Lys Met Glu Asn Gln Ser Glu Asn Asn Asp Ile Asp Glu Val Ile Ile
305                 310                 315                 320

Pro Thr Ala Pro Leu Tyr Lys Gln Ile Leu Asn Leu Tyr Ala Glu Glu
                325                 330                 335

Asn Ala Ile Glu Asp Thr Ile Phe Tyr Leu Gly Glu Ala Leu Arg Arg
                340                 345                 350

Gly Val Ile Asp Leu Asp Val Phe Leu Lys His Val Arg Leu Leu Ser
                355                 360                 365

Arg Lys Gln Phe Gln Leu Arg Ala Leu Met Gln Lys Ala Arg Lys Thr
                370                 375                 380

Ala Gly Leu Ser Asp Leu Tyr
385                 390

<210> SEQ ID NO 2
<211> LENGTH: 390
<212> TYPE: PRT
<213> ORGANISM: Homo sapiens

<400> SEQUENCE: 2

Met Ala Val Ser Glu Ser Gln Leu Lys Lys Met Val Ser Lys Tyr Lys
1               5                   10                  15

Tyr Arg Asp Leu Thr Val Arg Glu Thr Val Asn Val Ile Thr Leu Tyr
                20                  25                  30

Lys Asp Leu Lys Pro Val Leu Asp Ser Tyr Val Phe Asn Asp Gly Ser
                35                  40                  45
```

Ser Arg Glu Leu Met Asn Leu Thr Gly Thr Ile Pro Val Pro Tyr Arg
 50                  55                  60

Gly Asn Thr Tyr Asn Ile Pro Ile Cys Leu Trp Leu Asp Thr Tyr
 65                  70                  75                  80

Pro Tyr Asn Pro Pro Ile Cys Phe Val Lys Pro Thr Ser Ser Met Thr
                 85                  90                  95

Ile Lys Thr Gly Lys His Val Asp Ala Asn Gly Lys Ile Tyr Leu Pro
             100                 105                 110

Tyr Leu His Glu Trp Lys His Pro Gln Ser Asp Leu Leu Gly Leu Ile
         115                 120                 125

Gln Val Met Ile Val Val Phe Gly Asp Glu Pro Pro Val Phe Ser Arg
130                 135                 140

Pro Ile Ser Ala Ser Tyr Pro Pro Tyr Gln Ala Thr Gly Pro Pro Asn
145                 150                 155                 160

Thr Ser Tyr Met Pro Gly Met Pro Gly Gly Ile Ser Pro Tyr Pro Ser
                165                 170                 175

Gly Tyr Pro Pro Asn Pro Ser Gly Tyr Pro Gly Cys Pro Tyr Pro Pro
            180                 185                 190

Gly Gly Pro Tyr Pro Ala Thr Thr Ser Ser Gln Tyr Pro Ser Gln Pro
        195                 200                 205

Pro Val Thr Thr Val Gly Pro Ser Arg Asp Gly Thr Ile Ser Glu Asp
    210                 215                 220

Thr Ile Arg Ala Ser Leu Ile Ser Ala Val Ser Asp Lys Leu Arg Trp
225                 230                 235                 240

Arg Met Lys Glu Glu Met Asp Arg Ala Gln Ala Glu Leu Asn Ala Leu
                245                 250                 255

Lys Arg Thr Glu Glu Asp Leu Lys Lys Gly His Gln Lys Leu Glu Glu
            260                 265                 270

Met Val Thr Arg Leu Asp Gln Glu Val Ala Glu Val Asp Lys Asn Ile
        275                 280                 285

Glu Leu Leu Lys Lys Lys Asp Glu Glu Leu Ser Ser Ala Leu Glu Lys
    290                 295                 300

Met Glu Asn Gln Ser Glu Asn Asn Asp Ile Asp Glu Val Ile Ile Pro
305                 310                 315                 320

Thr Ala Pro Leu Tyr Lys Gln Ile Leu Asn Leu Tyr Ala Glu Glu Asn
                325                 330                 335

Ala Ile Glu Asp Thr Ile Phe Tyr Leu Gly Glu Ala Leu Arg Arg Gly
            340                 345                 350

Val Ile Asp Leu Asp Val Phe Leu Lys His Val Arg Leu Leu Ser Arg
        355                 360                 365

Lys Gln Phe Gln Leu Arg Ala Leu Met Gln Lys Ala Arg Lys Thr Ala
    370                 375                 380

Gly Leu Ser Asp Leu Tyr
385                 390

<210> SEQ ID NO 3
<211> LENGTH: 375
<212> TYPE: PRT
<213> ORGANISM: Mus musculus

<400> SEQUENCE: 3

Met Asp Ala Leu Arg Leu Ala Asn Ser Ala Phe Ala Val Asp Leu Phe
 1               5                  10                  15

Lys Gln Leu Cys Glu Arg Asp Pro Ala Gly Asn Ile Leu Phe Ser Pro
             20                  25                  30

```
Ile Cys Leu Ser Thr Ser Leu Ser Leu Ala Gln Val Gly Thr Lys Gly
             35                  40                  45

Asp Thr Ala Asn Glu Ile Gly Gln Val Leu His Phe Glu Asn Val Lys
 50                  55                  60

Asp Val Pro Phe Gly Phe Gln Thr Val Thr Ser Asp Val Asn Lys Leu
 65                  70                  75                  80

Ser Ser Phe Tyr Ser Leu Lys Leu Val Lys Arg Leu Tyr Ile Asp Lys
                 85                  90                  95

Ser Leu Asn Pro Ser Thr Glu Phe Ile Ser Ser Thr Lys Arg Pro Tyr
                100                 105                 110

Ala Lys Glu Leu Glu Thr Val Asp Phe Lys Asp Lys Leu Glu Glu Thr
            115                 120                 125

Lys Gly Gln Ile Asn Ser Ser Ile Lys Glu Leu Thr Asp Gly His Phe
130                 135                 140

Glu Asp Ile Leu Ser Glu Asn Ser Ile Ser Asp Gln Thr Lys Ile Leu
145                 150                 155                 160

Val Val Asn Ala Ala Tyr Phe Val Gly Lys Trp Met Lys Lys Phe Pro
                165                 170                 175

Glu Ser Glu Thr Lys Glu Cys Pro Phe Arg Ile Ser Lys Thr Asp Thr
            180                 185                 190

Lys Pro Val Gln Met Met Asn Leu Glu Ala Thr Phe Cys Leu Gly Asn
            195                 200                 205

Ile Asp Asp Ile Ser Cys Lys Ile Ile Glu Leu Pro Phe Gln Asn Lys
            210                 215                 220

His Leu Ser Met Leu Ile Val Leu Pro Lys Asp Val Glu Asp Glu Ser
225                 230                 235                 240

Thr Gly Leu Glu Lys Ile Glu Gln Gln Leu Asn Pro Glu Thr Leu Leu
                245                 250                 255

Gln Trp Thr Asn Pro Ser Thr Met Ala Asn Ala Lys Val Lys Leu Ser
            260                 265                 270

Leu Pro Lys Phe Lys Val Glu Lys Met Ile Asp Pro Lys Ala Ser Leu
            275                 280                 285

Glu Ser Leu Gly Leu Lys Ser Leu Phe Asn Glu Ser Thr Ser Asp Phe
290                 295                 300

Ser Gly Met Ser Glu Thr Lys Gly Val Ser Leu Ser Asn Val Ile His
305                 310                 315                 320

Arg Val Cys Leu Glu Ile Thr Glu Asp Gly Gly Glu Ser Ile Glu Val
                325                 330                 335

Pro Gly Ser Arg Ile Leu Gln His Lys Asp Glu Phe Asn Ala Asp His
            340                 345                 350

Pro Phe Ile Tyr Ile Ile Arg His Asn Lys Thr Arg Asn Ile Ile Phe
                355                 360                 365

Phe Gly Lys Phe Cys Ser Pro
370                 375

<210> SEQ ID NO 4
<211> LENGTH: 375
<212> TYPE: PRT
<213> ORGANISM: Homo sapiens

<400> SEQUENCE: 4

Met Asp Ala Leu Gln Leu Ala Asn Ser Ala Phe Ala Val Asp Leu Phe
 1               5                  10                  15

Lys Gln Leu Cys Glu Lys Glu Pro Leu Gly Asn Val Leu Phe Ser Pro
```

```
                    20                  25                  30
Ile Cys Leu Ser Thr Ser Leu Ser Leu Ala Gln Val Gly Ala Lys Gly
                35                  40                  45

Asp Thr Ala Asn Glu Ile Gly Gln Val Leu His Phe Glu Asn Val Lys
     50                  55                  60

Asp Ile Pro Phe Gly Phe Gln Thr Val Thr Ser Asp Val Asn Lys Leu
 65                  70                  75                  80

Ser Ser Phe Tyr Ser Leu Lys Leu Ile Lys Arg Leu Tyr Val Asp Lys
                 85                  90                  95

Ser Leu Asn Leu Ser Thr Glu Phe Ile Ser Ser Thr Lys Arg Pro Tyr
                100                 105                 110

Ala Lys Glu Leu Glu Thr Val Asp Phe Lys Asp Lys Leu Glu Glu Thr
            115                 120                 125

Lys Gly Gln Ile Asn Asn Ser Ile Lys Asp Leu Thr Asp Gly His Phe
        130                 135                 140

Glu Asn Ile Leu Ala Asp Asn Ser Val Asn Asp Gln Thr Lys Ile Leu
145                 150                 155                 160

Val Val Asn Ala Ala Tyr Phe Val Gly Lys Trp Met Lys Lys Phe Pro
                165                 170                 175

Glu Ser Glu Thr Lys Glu Cys Pro Phe Arg Leu Asn Lys Thr Asp Thr
            180                 185                 190

Lys Pro Val Gln Met Met Asn Met Glu Ala Thr Phe Cys Met Gly Asn
        195                 200                 205

Ile Asp Ser Ile Asn Cys Lys Ile Ile Glu Leu Pro Phe Gln Asn Lys
    210                 215                 220

His Leu Ser Met Phe Ile Leu Leu Pro Lys Asp Val Glu Asp Glu Ser
225                 230                 235                 240

Thr Gly Leu Glu Lys Ile Glu Lys Gln Leu Asn Ser Glu Ser Leu Ser
                245                 250                 255

Gln Trp Thr Asn Pro Ser Thr Met Ala Asn Ala Lys Val Lys Leu Ser
            260                 265                 270

Ile Pro Lys Phe Lys Val Glu Lys Met Ile Asp Pro Lys Ala Cys Leu
        275                 280                 285

Glu Asn Leu Gly Leu Lys His Ile Phe Ser Glu Asp Thr Ser Asp Phe
    290                 295                 300

Ser Gly Met Ser Glu Thr Lys Gly Val Ala Leu Ser Asn Val Ile His
305                 310                 315                 320

Lys Val Cys Leu Glu Ile Thr Glu Asp Gly Gly Asp Ser Ile Glu Val
                325                 330                 335

Pro Gly Ala Arg Ile Leu Gln His Lys Asp Glu Leu Asn Ala Asp His
            340                 345                 350

Pro Phe Ile Tyr Ile Ile Arg His Asn Lys Thr Arg Asn Ile Ile Phe
        355                 360                 365

Phe Gly Lys Phe Cys Ser Pro
    370                 375

<210> SEQ ID NO 5
<211> LENGTH: 833
<212> TYPE: PRT
<213> ORGANISM: Mus musculus

<400> SEQUENCE: 5

Met Lys Gly Gly Thr Ser Lys Phe Lys Thr His Thr Glu Thr Leu Tyr
 1               5                  10                  15
```

Lys Lys Lys Lys Trp Ser Ser Val Ser Glu Lys Arg Pro Gln Lys Cys
                20                  25                  30

Pro Ser Gln Cys Leu Glu Ser Lys Gln Pro Gln Val Ser Val Leu Gly
            35                  40                  45

Lys Arg Arg Arg Ala Ser Gln Thr Pro Ala Gln Glu Thr Leu Glu Ser
        50                  55                  60

Glu Trp Pro Gln Lys Ala Lys Lys Lys Arg Arg Gly Glu Pro Gln
65                  70                  75                  80

Thr Pro Thr Gln Glu Ser Leu Glu Ser Gln Pro Pro Val Ser Leu
                    85                  90                  95

Leu Gly Lys Arg Arg Arg Glu Ser Gln Thr Pro Ala Gln Glu Asn Ser
                100                 105                 110

Glu Ser Glu Gln Pro Arg Lys Ala Lys Arg Arg Lys Lys Arg Lys
            115                 120                 125

Gly Ser Gln Gln Pro Thr Ser Ser Leu Leu Lys Thr Pro Glu Thr Phe
        130                 135                 140

Leu Lys Ala Lys Lys Thr Thr Ser Ala His Lys Lys Lys Asn Ser
145                 150                 155                 160

Val Leu Glu Val Asp Met Glu Thr Gly Ile Ile Leu Val Asp Lys Glu
                    165                 170                 175

Asn Met Glu Asn Leu Leu Glu Thr Ser Arg Lys Asp Val Asp Ile Val
                180                 185                 190

Tyr Val Asp Met Ser Lys Gly Gln Arg Ser Ala Lys Val Arg Glu Thr
            195                 200                 205

Gly Glu Leu Pro Ala Ala Lys Pro Gln Glu His Gly Cys Arg Glu Leu
        210                 215                 220

Leu Gly Asp Val Arg Ser Arg Lys Lys Gln Lys His Leu Gln Lys Val
225                 230                 235                 240

Ala Pro Trp Asp Val Val Gln Gly Ser Gln Pro Glu Ser Ile Ser Leu
                    245                 250                 255

Pro Pro Ser Glu Pro Leu Ser Ser Glu Asp Leu Glu Gly Lys Ser Thr
                260                 265                 270

Glu Ala Ala Val Phe Cys Lys Arg Ser Leu Lys Lys Asn Val Phe Arg
            275                 280                 285

Ser Gln Glu Leu Glu Pro Ile Pro Asp Ser Leu Asp Asp Ser Glu Thr
        290                 295                 300

Ile Ser Glu Arg Leu Asp Ser Thr His His Gly Gly Ala Val Gly Ala
305                 310                 315                 320

Gly Glu Cys Glu Ser Thr Lys Glu Ser His Ser Ile Lys Lys Ser
                    325                 330                 335

Lys Lys Lys Lys His Lys Ser Val Ala Leu Ala Thr Ser Ser Asp Ser
                340                 345                 350

Ala Ser Val Thr Asp Ser Lys Ala Lys Asn Ala Leu Val Asp Ser Ser
            355                 360                 365

Glu Gly Ser Gly Ala Val Arg Glu Glu Asp Val Asp His Arg Pro Ala
        370                 375                 380

Glu Ala Glu Ala Gln Ala Cys Ser Thr Glu Lys His Arg Glu Ala Met
385                 390                 395                 400

Gln Arg Leu Glu Pro Thr His Glu Glu Ser Asn Ser Glu Ser Ala
                    405                 410                 415

Ser Asn Ser Ala Ala Arg His Ile Ser Glu Asp Arg Arg Glu Ser Asp
                420                 425                 430

Asp Ser Asp Val Asp Leu Gly Ser Ala Val Arg Gln Leu Arg Glu Phe

```
            435                 440                 445
Ile Pro Asp Ile Gln Glu Arg Ala Ala Thr Thr Ile Arg Arg Met Tyr
    450                 455                 460

Arg Asp Asp Leu Gly Leu Phe Lys Glu Phe Lys Ala Gln Gly Val Ala
465                 470                  475                 480

Ile Arg Phe Gly Lys Phe Ser Ala Lys Glu Asn Lys Gln Ile Glu Lys
                485                 490                 495

Asn Val Gln Asp Phe Leu Ser Leu Thr Gly Ile Glu Ser Ala Asp Lys
            500                 505                 510

Leu Leu Tyr Thr Asp Arg Tyr Pro Glu Glu Lys Thr Leu Ile Thr Asn
        515                 520                 525

Leu Lys Arg Lys His Ala Phe Arg Leu His Ile Gly Lys Gly Ile Ala
    530                 535                 540

Arg Pro Trp Lys Leu Val Tyr Tyr Arg Ala Lys Lys Ile Phe Asp Val
545                 550                 555                 560

Asn Asn Tyr Lys Gly Arg Tyr Asn Glu Glu Asp Thr Lys Lys Leu Lys
                565                 570                 575

Ala Tyr His Ser Leu His Gly Asn Asp Trp Lys Ile Gly Ala Met
            580                 585                 590

Val Ala Arg Ser Ser Leu Ser Val Ala Leu Lys Phe Ser Gln Ile Gly
        595                 600                 605

Gly Thr Arg Asn Gln Gly Ala Trp Ser Lys Ala Glu Thr Gln Arg Leu
    610                 615                 620

Ile Lys Ala Val Glu Asp Val Ile Leu Lys Lys Met Ser Pro Gln Glu
625                 630                 635                 640

Leu Arg Glu Leu Asp Ser Lys Leu Gln Glu Asp Pro Glu Gly Arg Leu
                645                 650                 655

Ser Ile Val Arg Glu Lys Leu Tyr Lys Gly Ile Ser Trp Val Glu Val
            660                 665                 670

Glu Ala Arg Val Glu Thr Arg Asn Trp Met Gln Cys Lys Ser Lys Trp
        675                 680                 685

Thr Glu Ile Leu Thr Lys Arg Met Thr His Gly Gly Phe Val Tyr Arg
    690                 695                 700

Gly Val Asn Ala Leu Gln Ala Lys Ile Thr Leu Ile Glu Arg Leu Tyr
705                 710                 715                 720

Glu Leu Asn Val Asn Asp Ala Asn Glu Ile Asp Trp Glu Asp Leu Cys
                725                 730                 735

Ser Ala Ile Gly Asp Val Pro Pro Phe Val Gln Ala Lys Phe Tyr
            740                 745                 750

Lys Leu Lys Ala Ala Cys Val Pro Phe Trp Gln Lys Lys Thr Phe Pro
        755                 760                 765

Glu Ile Ile Asp Tyr Leu Tyr Lys Asn Ser Leu Pro Leu Leu Lys Glu
    770                 775                 780

Lys Leu Asp Lys Lys Met Lys Lys Lys Asp Gly Gln Ile Gln Thr Pro
785                 790                 795                 800

Ala Ala Pro Lys Gln Asp Phe Leu Phe Lys Asp Ile Phe His Cys Asp
                805                 810                 815

Asp Asp Ser Asp Glu Gly Ser Pro Glu Glu Pro Ser Ala Ser Asp Val
            820                 825                 830

Gln

<210> SEQ ID NO 6
<211> LENGTH: 886
```

```
<212> TYPE: PRT
<213> ORGANISM: Homo sapiens

<400> SEQUENCE: 6

Met Glu Gly Glu Ser Ser Arg Phe Glu Ile His Thr Pro Val Ser Asp
 1               5                  10                  15

Lys Lys Lys Lys Lys Cys Ser Ile His Lys Glu Arg Pro Gln Lys His
             20                  25                  30

Ser His Glu Ile Phe Arg Asp Ser Ser Leu Val Asn Glu Gln Ser Gln
         35                  40                  45

Ile Thr Arg Arg Lys Lys Arg Lys Lys Asp Phe Gln His Leu Ile Ser
     50                  55                  60

Ser Pro Leu Lys Lys Ser Arg Ile Cys Asp Glu Thr Ala Asn Ala Thr
 65                  70                  75                  80

Ser Thr Leu Lys Lys Arg Lys Lys Arg Tyr Ser Ala Leu Glu Val
                 85                  90                  95

Asp Glu Glu Ala Gly Val Thr Val Leu Val Asp Lys Glu Asn Ile
                100                 105                 110

Asn Asn Thr Pro Lys His Phe Arg Lys Asp Val Asp Val Cys Val
            115                 120                 125

Asp Met Ser Ile Glu Gln Lys Leu Pro Arg Lys Pro Lys Thr Asp Lys
130                 135                 140

Phe Gln Val Leu Ala Lys Ser His Ala His Lys Ser Glu Ala Leu His
145                 150                 155                 160

Ser Lys Val Arg Glu Lys Lys Asn Lys His Gln Arg Lys Ala Ala
                165                 170                 175

Ser Trp Glu Ser Gln Arg Ala Arg Asp Thr Leu Pro Gln Ser Glu Ser
                180                 185                 190

His Gln Glu Glu Ser Trp Leu Ser Val Gly Pro Gly Gly Glu Ile Thr
            195                 200                 205

Glu Leu Pro Ala Ser Ala His Lys Asn Lys Ser Lys Lys Lys Lys
    210                 215                 220

Lys Ser Ser Asn Arg Glu Tyr Glu Thr Leu Ala Met Pro Glu Gly Ser
225                 230                 235                 240

Gln Ala Gly Arg Glu Ala Gly Thr Asp Met Gln Glu Ser Gln Pro Thr
                245                 250                 255

Val Gly Leu Asp Asp Glu Thr Pro Gln Leu Leu Gly Pro Thr His Lys
            260                 265                 270

Lys Lys Ser Lys Lys Lys Lys Lys Ser Asn His Gln Glu Phe
    275                 280                 285

Glu Ala Leu Ala Met Pro Glu Gly Ser Gln Val Gly Ser Glu Val Gly
    290                 295                 300

Ala Asp Met Gln Glu Ser Arg Pro Ala Val Gly Leu His Gly Glu Thr
305                 310                 315                 320

Ala Gly Ile Pro Ala Pro Ala Tyr Lys Asn Lys Ser Lys Lys Lys
                325                 330                 335

Lys Lys Ser Asn His Gln Glu Phe Glu Ala Val Ala Met Pro Glu Ser
            340                 345                 350

Leu Glu Ser Ala Tyr Pro Glu Gly Ser Gln Val Gly Ser Glu Val Gly
            355                 360                 365

Thr Val Glu Gly Ser Thr Ala Leu Lys Gly Phe Lys Glu Ser Asn Ser
        370                 375                 380

Thr Lys Lys Lys Ser Lys Lys Arg Lys Leu Thr Ser Val Lys Arg Ala
385                 390                 395                 400
```

```
Arg Val Ser Gly Asp Asp Phe Ser Val Pro Ser Lys Asn Ser Glu Ser
            405                 410                 415

Thr Leu Phe Asp Ser Val Glu Gly Asp Gly Ala Met Met Glu Glu Gly
            420                 425                 430

Val Lys Ser Arg Pro Arg Gln Lys Lys Thr Gln Ala Cys Leu Ala Ser
            435                 440                 445

Lys His Val Gln Glu Ala Pro Arg Leu Glu Pro Ala Asn Glu Glu His
            450                 455                 460

Asn Val Glu Thr Ala Glu Asp Ser Glu Ile Arg Tyr Leu Ser Ala Asp
465                 470                 475                 480

Ser Gly Asp Ala Asp Asp Ser Asp Ala Asp Leu Gly Ser Ala Val Lys
            485                 490                 495

Gln Leu Gln Glu Phe Ile Pro Asn Ile Lys Asp Arg Ala Thr Ser Thr
            500                 505                 510

Ile Lys Arg Met Tyr Arg Asp Asp Leu Glu Arg Phe Lys Glu Phe Lys
            515                 520                 525

Ala Gln Gly Val Ala Ile Lys Phe Gly Lys Phe Ser Val Lys Glu Asn
            530                 535                 540

Lys Gln Leu Glu Lys Asn Val Glu Asp Phe Leu Ala Leu Thr Gly Ile
545                 550                 555                 560

Glu Ser Ala Asp Lys Leu Leu Tyr Thr Asp Arg Tyr Pro Glu Glu Lys
            565                 570                 575

Ser Val Ile Thr Asn Leu Lys Arg Arg Tyr Ser Phe Arg Leu His Ile
            580                 585                 590

Gly Arg Asn Ile Ala Arg Pro Trp Lys Leu Ile Tyr Tyr Arg Ala Lys
            595                 600                 605

Lys Met Phe Asp Val Asn Asn Tyr Lys Gly Arg Tyr Ser Glu Gly Asp
            610                 615                 620

Thr Glu Lys Leu Lys Met Tyr His Ser Leu Leu Gly Asn Asp Trp Lys
625                 630                 635                 640

Thr Ile Gly Glu Met Val Ala Arg Arg Ser Leu Ser Val Ala Leu Lys
            645                 650                 655

Phe Ser Gln Ile Ser Ser Gln Arg Asn Arg Gly Ala Trp Ser Lys Ser
            660                 665                 670

Glu Thr Arg Lys Leu Ile Lys Ala Val Glu Glu Val Ile Leu Lys Lys
            675                 680                 685

Met Ser Pro Gln Glu Leu Lys Glu Val Asp Ser Lys Leu Gln Glu Asn
            690                 695                 700

Pro Glu Ser Cys Leu Ser Ile Val Arg Glu Lys Leu Tyr Lys Gly Ile
705                 710                 715                 720

Ser Trp Val Glu Val Glu Ala Lys Val Gln Thr Arg Asn Trp Met Gln
            725                 730                 735

Cys Lys Ser Lys Trp Thr Glu Ile Leu Thr Lys Arg Met Thr Asn Gly
            740                 745                 750

Arg Arg Ile Tyr Tyr Gly Met Asn Ala Leu Arg Ala Lys Val Ser Leu
            755                 760                 765

Ile Glu Arg Leu Tyr Glu Ile Asn Val Glu Asp Thr Asn Glu Ile Asp
            770                 775                 780

Trp Glu Asp Leu Ala Ser Ala Ile Gly Asp Val Pro Pro Ser Tyr Val
785                 790                 795                 800

Gln Thr Lys Phe Ser Arg Leu Lys Ala Val Tyr Val Pro Phe Trp Gln
            805                 810                 815
```

```
Lys Lys Thr Phe Pro Glu Ile Ile Asp Tyr Leu Tyr Glu Thr Thr Leu
            820                 825                 830

Pro Leu Leu Lys Glu Lys Leu Glu Lys Met Met Glu Lys Lys Gly Thr
            835                 840                 845

Lys Ile Gln Thr Pro Ala Ala Pro Lys Gln Val Phe Pro Phe Arg Asp
            850                 855                 860

Ile Phe Tyr Tyr Glu Asp Asp Ser Glu Gly Gly His Arg Lys Arg
865                 870                 875                 880

Lys Arg Arg Gly Ile Pro
                885

<210> SEQ ID NO 7
<211> LENGTH: 659
<212> TYPE: PRT
<213> ORGANISM: Mus musculus

<400> SEQUENCE: 7

Met Glu Gly Gly Cys Gly Glu Gly Gly Gly Thr Gly Ser Gly Arg
  1               5                  10                  15

Ser Ala Ala Ala Arg Arg Ala Gly Arg Met Arg Pro Arg Ala Gln
             20                  25                  30

Gly Pro Asp Ser Glu Ser Gly Gly Glu Ala Ser Arg Leu Asn Leu Leu
             35                  40                  45

Asp Thr Cys Ala Val Cys His Gln Asn Ile Gln Ser Arg Val Pro Lys
 50                  55                  60

Leu Leu Pro Cys Leu His Ser Phe Cys Gln Arg Cys Leu Pro Ala Pro
 65                  70                  75                  80

Gln Arg Tyr Leu Met Leu Thr Ala Pro Ala Leu Gly Ser Ala Glu Thr
             85                  90                  95

Pro Pro Pro Ala Pro Ala Pro Ala Pro Gly Ser Pro Ala Gly
            100                 105                 110

Gly Pro Ser Pro Phe Ala Thr Gln Val Gly Val Ile Arg Cys Pro Val
            115                 120                 125

Cys Ser Gln Glu Cys Ala Glu Arg His Ile Ile Asp Asn Phe Phe Val
            130                 135                 140

Lys Asp Thr Thr Glu Val Pro Ser Ser Thr Val Glu Lys Ser Asn Gln
145                 150                 155                 160

Val Cys Thr Ser Cys Glu Asp Asn Ala Glu Ala Asn Gly Phe Cys Val
                165                 170                 175

Glu Cys Val Glu Trp Leu Cys Lys Thr Cys Ile Arg Ala His Gln Arg
            180                 185                 190

Val Lys Phe Thr Lys Asp His Thr Val Arg Gln Lys Glu Glu Val Ser
            195                 200                 205

Pro Glu Ala Val Gly Val Thr Ser Gln Arg Pro Val Phe Cys Pro Phe
    210                 215                 220

His Lys Lys Glu Gln Leu Lys Leu Tyr Cys Glu Thr Cys Asp Lys Leu
225                 230                 235                 240

Thr Cys Arg Asp Cys Gln Leu Leu Glu His Lys Glu His Arg Tyr Gln
                245                 250                 255

Phe Ile Glu Glu Ala Phe Gln Asn Gln Lys Val Ile Ile Asp Thr Leu
            260                 265                 270

Ile Thr Lys Leu Met Glu Lys Thr Lys Tyr Ile Lys Tyr Thr Gly Asn
            275                 280                 285

Gln Ile Gln Asn Arg Ile Ile Glu Ile Asn Gln Asn Gln Lys Gln Val
            290                 295                 300
```

Glu Gln Asp Ile Lys Val Ala Ile Phe Thr Leu Met Val Glu Ile Asn
305                 310                 315                 320

Lys Lys Gly Lys Ala Leu Leu His Gln Leu Glu Lys Thr Leu Gly Arg
            325                 330                 335

Arg Asp Ser Ser Asp Asp Trp Glu Ile Pro Asp Gly Gln Ile Thr Val
            340                 345                 350

Gly Gln Arg Ile Gly Ser Gly Ser Phe Gly Thr Val Tyr Lys Gly Lys
            355                 360                 365

Trp His Gly Asp Val Ala Val Lys Met Leu Asn Val Thr Ala Pro Thr
        370                 375                 380

Pro Gln Gln Leu Gln Ala Phe Lys Asn Glu Val Gly Val Leu Arg Lys
385                 390                 395                 400

Thr Arg His Val Asn Ile Leu Leu Phe Met Gly Tyr Ser Thr Lys Pro
                405                 410                 415

Gln Leu Ala Ile Val Thr Gln Trp Cys Glu Gly Ser Ser Leu Tyr His
                420                 425                 430

His Leu His Ile Ile Glu Thr Lys Phe Glu Met Ile Lys Leu Ile Asp
            435                 440                 445

Ile Ala Arg Gln Thr Ala Gln Gly Met Asp Tyr Leu His Ala Lys Ser
450                 455                 460

Ile Ile His Arg Asp Leu Lys Ser Asn Asn Ile Phe Leu His Glu Asp
465                 470                 475                 480

Leu Thr Val Lys Ile Gly Asp Phe Gly Leu Ala Thr Val Lys Ser Arg
                485                 490                 495

Trp Ser Gly Ser His Gln Phe Glu Gln Leu Ser Gly Ser Ile Leu Trp
            500                 505                 510

Met Ala Pro Glu Val Ile Arg Met Gln Asp Lys Asn Pro Tyr Ser Phe
        515                 520                 525

Gln Ser Asp Val Tyr Ala Phe Gly Ile Val Leu Tyr Glu Leu Met Thr
            530                 535                 540

Gly Gln Leu Pro Tyr Ser Asn Ile Asn Asn Arg Asp Gln Ile Ile Phe
545                 550                 555                 560

Met Val Gly Arg Gly Tyr Leu Ser Pro Asp Leu Ser Lys Val Arg Ser
                565                 570                 575

Asn Cys Pro Lys Ala Met Lys Arg Leu Met Ala Glu Cys Leu Lys Lys
            580                 585                 590

Lys Arg Asp Glu Arg Pro Leu Phe Pro Gln Ile Leu Ala Ser Ile Glu
            595                 600                 605

Leu Leu Ala Arg Ser Leu Pro Lys Ile His Arg Ser Ala Ser Glu Pro
610                 615                 620

Ser Leu Asn Arg Ala Gly Phe Gln Thr Glu Asp Phe Ser Leu Tyr Ala
625                 630                 635                 640

Cys Ala Ser Pro Lys Thr Pro Ile Gln Ala Gly Gly Tyr Gly Gly Phe
                645                 650                 655

Pro Val His

<210> SEQ ID NO 8
<211> LENGTH: 765
<212> TYPE: PRT
<213> ORGANISM: Homo sapiens

<400> SEQUENCE: 8

Met Ala Ala Leu Ser Gly Gly Gly Gly Gly Gly Ala Glu Pro Gly Gln
1               5                   10                  15

-continued

```
Ala Leu Phe Asn Gly Asp Met Glu Pro Glu Ala Gly Ala Gly Arg Pro
                20                  25                  30
Ala Ala Ser Ser Ala Ala Asp Pro Ala Ile Pro Glu Glu Val Trp Asn
            35                  40                  45
Ile Lys Gln Met Ile Lys Leu Thr Gln Glu His Ile Glu Ala Leu Leu
        50                  55                  60
Asp Lys Phe Gly Gly Glu His Asn Pro Pro Ser Ile Tyr Leu Glu Ala
65                  70                  75                  80
Tyr Glu Glu Tyr Thr Ser Lys Leu Asp Ala Leu Gln Gln Arg Glu Gln
                85                  90                  95
Gln Leu Leu Glu Ser Leu Gly Asn Gly Thr Asp Phe Ser Val Ser Ser
            100                 105                 110
Ser Ala Ser Met Asp Thr Val Thr Ser Ser Ser Ser Ser Ser Leu Ser
        115                 120                 125
Val Leu Pro Ser Ser Leu Ser Val Phe Gln Asn Pro Thr Asp Val Ala
130                 135                 140
Arg Ser Asn Pro Lys Ser Pro Gln Lys Pro Ile Val Arg Val Phe Leu
145                 150                 155                 160
Pro Asn Lys Gln Arg Thr Val Val Pro Ala Arg Cys Gly Val Thr Val
                165                 170                 175
Arg Asp Ser Leu Lys Lys Ala Leu Met Met Arg Gly Leu Ile Pro Glu
            180                 185                 190
Cys Cys Ala Val Tyr Arg Ile Gln Asp Gly Glu Lys Lys Pro Ile Gly
        195                 200                 205
Trp Asp Thr Asp Ile Ser Trp Leu Thr Gly Glu Glu Leu His Val Glu
    210                 215                 220
Val Leu Glu Asn Val Pro Leu Thr Thr His Asn Phe Val Arg Lys Thr
225                 230                 235                 240
Phe Phe Thr Leu Ala Phe Cys Asp Phe Cys Arg Lys Leu Leu Phe Gln
                245                 250                 255
Gly Phe Arg Cys Gln Thr Cys Gly Tyr Lys Phe His Gln Arg Cys Ser
            260                 265                 270
Thr Glu Val Pro Leu Met Cys Val Asn Tyr Asp Gln Leu Asp Leu Leu
        275                 280                 285
Phe Val Ser Lys Phe Phe Glu His His Pro Ile Pro Gln Glu Glu Ala
    290                 295                 300
Ser Leu Ala Glu Thr Ala Leu Thr Ser Gly Ser Ser Pro Ser Ala Pro
305                 310                 315                 320
Ala Ser Asp Ser Ile Gly Pro Gln Ile Leu Thr Ser Pro Ser Pro Ser
                325                 330                 335
Lys Ser Ile Pro Ile Pro Gln Pro Phe Arg Pro Ala Asp Glu Asp His
            340                 345                 350
Arg Asn Gln Phe Gly Gln Arg Asp Arg Ser Ser Ser Ala Pro Asn Val
        355                 360                 365
His Ile Asn Thr Ile Glu Pro Val Asn Ile Asp Asp Leu Ile Arg Asp
    370                 375                 380
Gln Gly Phe Arg Gly Asp Gly Gly Ser Thr Thr Gly Leu Ser Ala Thr
385                 390                 395                 400
Pro Pro Ala Ser Leu Pro Gly Ser Leu Thr Asn Val Lys Ala Leu Gln
                405                 410                 415
Lys Ser Pro Gly Pro Gln Arg Glu Arg Lys Ser Ser Ser Ser Ser Glu
            420                 425                 430
```

```
Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Ile Leu Ala Ser Ile Glu Leu Leu Ala Arg Ser Leu
705                 710                 715                 720

Pro Lys Ile His Arg Ser Ala Ser Glu Pro Ser Leu Asn Arg Ala Gly
                725                 730                 735

Phe Gln Thr Glu Asp Phe Ser Leu Tyr Ala Cys Ala Ser Pro Lys Thr
            740                 745                 750

Pro Ile Gln Ala Gly Gly Tyr Gly Ala Phe Pro Val His
        755                 760                 765

<210> SEQ ID NO 9
<211> LENGTH: 111
<212> TYPE: PRT
<213> ORGANISM: Mus musculus

<400> SEQUENCE: 9

Met Ser Asp Ala Ala Val Asp Thr Ser Ser Glu Ile Thr Thr Lys Asp
 1               5                  10                  15

Leu Lys Glu Lys Lys Glu Val Val Glu Glu Ala Glu Asn Gly Arg Asp
                20                  25                  30

Ala Pro Ala Asn Gly Asn Ala Gln Asn Glu Glu Asn Gly Glu Gln Glu
            35                  40                  45
```

-continued

Ala Asp Asn Glu Val Asp Glu Glu Glu Gly Gly Glu Glu
         50                  55                  60

Glu Glu Glu Glu Glu Gly Asp Gly Glu Glu Asp Gly Asp Glu Asp
65                  70                  75                  80

Glu Glu Ala Glu Ala Pro Thr Gly Lys Arg Val Ala Glu Asp Glu
             85                  90                  95

Asp Asp Asp Val Asp Thr Lys Lys Gln Lys Thr Glu Glu Asp Asp
                100                 105                 110

<210> SEQ ID NO 10
<211> LENGTH: 111
<212> TYPE: PRT
<213> ORGANISM: Homo sapiens

<400> SEQUENCE: 10

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
            20                  25                  30

Ala Pro Ala Asn Gly Asn Ala Glu Asn Glu Glu Asn Gly Glu Gln Glu
         35                  40                  45

Ala Asp Asn Glu Val Asp Glu Glu Glu Glu Gly Gly Glu Glu Glu
         50                  55                  60

Glu Glu Glu Glu Glu Gly Asp Gly Glu Glu Asp Gly Asp Glu Asp
65                  70                  75                  80

Glu Glu Ala Glu Ser Ala Thr Gly Lys Arg Ala Ala Glu Asp Asp Glu
             85                  90                  95

Asp Asp Asp Val Asp Thr Lys Lys Gln Lys Thr Asp Glu Asp Asp
                100                 105                 110

<210> SEQ ID NO 11
<211> LENGTH: 233
<212> TYPE: PRT
<213> ORGANISM: Mus musculus

<400> SEQUENCE: 11

Met Val Ser Met Thr Phe Lys Arg Ser Arg Ser Asp Arg Phe Tyr Ser
1               5                   10                  15

Thr Arg Cys Cys Gly Cys Phe His Val Arg Thr Gly Thr Ile Ile Leu
            20                  25                  30

Gly Thr Trp Tyr Met Val Val Asn Leu Leu Met Ala Ile Leu Leu Thr
         35                  40                  45

Val Glu Val Thr His Pro Asn Ser Met Pro Ala Val Asn Ile Gln Tyr
50                  55                  60

Glu Val Ile Gly Asn Tyr Tyr Ser Ser Glu Arg Met Ala Asp Asn Ala
65                  70                  75                  80

Cys Val Leu Phe Ala Val Ser Val Leu Met Phe Ile Ile Ser Ser Met
             85                  90                  95

Leu Val Tyr Gly Ala Ile Ser Tyr Gln Val Gly Trp Leu Ile Pro Phe
            100                 105                 110

Phe Cys Tyr Arg Leu Phe Asp Phe Val Leu Ser Cys Leu Val Ala Ile
            115                 120                 125

Ser Ser Leu Thr Tyr Leu Pro Arg Ile Lys Glu Tyr Leu Asp Gln Leu
        130                 135                 140

Pro Asp Phe Pro Tyr Lys Asp Asp Leu Leu Ala Leu Asp Ser Ser Cys
145                 150                 155                 160

Leu Leu Phe Ile Val Leu Val Phe Phe Val Phe Ile Ile Phe Lys
            165                 170                 175

Ala Tyr Leu Ile Asn Cys Val Trp Asn Cys Tyr Lys Tyr Ile Asn Asn
            180                 185                 190

Arg Asn Val Pro Glu Ile Ala Val Tyr Pro Ala Phe Glu Thr Pro Pro
        195                 200                 205

Gln Tyr Val Leu Pro Thr Tyr Glu Met Ala Val Lys Ile Pro Glu Lys
        210                 215                 220

Glu Pro Pro Pro Tyr Leu Pro Ala
225                 230

<210> SEQ ID NO 12
<211> LENGTH: 233
<212> TYPE: PRT
<213> ORGANISM: Homo sapiens

<400> SEQUENCE: 12

Met Val Ser Met Ser Phe Lys Arg Asn Arg Ser Asp Arg Phe Tyr Ser
1               5                   10                  15

Thr Arg Cys Cys Gly Cys Cys His Val Arg Thr Gly Thr Ile Ile Leu
            20                  25                  30

Gly Thr Trp Tyr Met Val Val Asn Leu Leu Met Ala Ile Leu Leu Thr
        35                  40                  45

Val Glu Val Thr His Pro Asn Ser Met Pro Ala Val Asn Ile Gln Tyr
50                  55                  60

Glu Val Ile Gly Asn Tyr Tyr Ser Ser Glu Arg Met Ala Asp Asn Ala
65                  70                  75                  80

Cys Val Leu Phe Ala Val Ser Val Leu Met Phe Ile Ile Ser Ser Met
                85                  90                  95

Leu Val Tyr Gly Ala Ile Ser Tyr Gln Val Gly Trp Leu Ile Pro Phe
            100                 105                 110

Phe Cys Tyr Arg Leu Phe Asp Phe Val Leu Ser Cys Leu Val Ala Ile
        115                 120                 125

Ser Ser Leu Thr Tyr Leu Pro Arg Ile Lys Glu Tyr Leu Asp Gln Leu
    130                 135                 140

Pro Asp Phe Pro Tyr Lys Asp Asp Leu Leu Ala Leu Asp Ser Ser Cys
145                 150                 155                 160

Leu Leu Phe Ile Val Leu Val Phe Phe Ala Leu Phe Ile Ile Phe Lys
                165                 170                 175

Ala Tyr Leu Ile Asn Cys Val Trp Asn Cys Tyr Lys Tyr Ile Asn Asn
            180                 185                 190

Arg Asn Val Pro Glu Ile Ala Val Tyr Pro Ala Phe Glu Ala Pro Pro
        195                 200                 205

Gln Tyr Val Leu Pro Thr Tyr Glu Met Ala Val Lys Met Pro Glu Lys
        210                 215                 220

Glu Pro Pro Pro Tyr Leu Pro Ala
225                 230

<210> SEQ ID NO 13
<211> LENGTH: 355
<212> TYPE: PRT
<213> ORGANISM: Mus musculus

<400> SEQUENCE: 13

Met Glu Ile Ser Asp Phe Thr Glu Ala Tyr Pro Thr Thr Thr Glu Phe
1               5                   10                  15

```
Asp Tyr Gly Asp Ser Thr Pro Cys Gln Lys Thr Ala Val Arg Ala Phe
            20                  25                  30

Gly Ala Gly Leu Leu Pro Pro Leu Tyr Ser Leu Val Phe Ile Ile Gly
            35                  40                  45

Val Val Gly Asn Val Leu Met Ile Leu Val Leu Met Gln His Arg Arg
        50                  55                  60

Leu Gln Ser Met Thr Ser Ile Tyr Leu Phe Asn Leu Ala Val Ser Asp
65                  70                  75                  80

Leu Val Phe Leu Phe Thr Leu Pro Phe Trp Ile Asp Tyr Lys Leu Lys
                85                  90                  95

Asp Asp Trp Ile Phe Gly Asp Ala Met Cys Lys Leu Leu Ser Gly Phe
            100                 105                 110

Tyr Tyr Leu Gly Leu Tyr Ser Glu Ile Phe Phe Ile Ile Leu Leu Thr
            115                 120                 125

Ile Asp Arg Tyr Leu Ala Ile Val His Ala Val Phe Ala Leu Arg Ala
        130                 135                 140

Arg Thr Val Thr Leu Gly Ile Ile Thr Ser Ile Ile Thr Trp Ala Leu
145                 150                 155                 160

Ala Ile Leu Ala Ser Met Pro Ala Leu Tyr Phe Phe Lys Ala Gln Trp
                165                 170                 175

Glu Phe Thr His Arg Thr Cys Ser Pro His Phe Pro Tyr Lys Ser Leu
            180                 185                 190

Lys Gln Trp Lys Arg Phe Gln Ala Leu Lys Leu Asn Leu Leu Gly Leu
            195                 200                 205

Ile Leu Pro Leu Leu Val Met Ile Ile Cys Tyr Ala Gly Ile Ile Arg
        210                 215                 220

Ile Leu Leu Arg Arg Pro Ser Glu Lys Lys Val Lys Ala Val Arg Leu
225                 230                 235                 240

Ile Phe Ala Ile Thr Leu Leu Phe Phe Leu Leu Trp Thr Pro Tyr Asn
                245                 250                 255

Leu Ser Val Phe Val Ser Ala Phe Gln Asp Val Leu Phe Thr Asn Gln
            260                 265                 270

Cys Glu Gln Ser Lys His Leu Asp Leu Ala Met Gln Val Thr Glu Val
            275                 280                 285

Ile Ala Tyr Thr His Cys Cys Val Asn Pro Ile Ile Tyr Val Phe Val
        290                 295                 300

Gly Glu Arg Phe Trp Lys Tyr Leu Arg Gln Leu Phe Gln Arg His Val
305                 310                 315                 320

Ala Ile Pro Leu Ala Lys Trp Leu Pro Phe Leu Ser Val Asp Gln Leu
                325                 330                 335

Glu Arg Thr Ser Ser Ile Ser Pro Ser Thr Gly Glu His Glu Leu Ser
            340                 345                 350

Ala Gly Phe
        355

<210> SEQ ID NO 14
<211> LENGTH: 355
<212> TYPE: PRT
<213> ORGANISM: Homo sapiens

<400> SEQUENCE: 14

Met Glu Thr Pro Asn Thr Thr Glu Asp Tyr Asp Thr Thr Thr Glu Phe
1               5                   10                  15

Asp Tyr Gly Asp Ala Thr Pro Cys Gln Lys Val Asn Glu Arg Ala Phe
```

```
            20                  25                  30
Gly Ala Gln Leu Leu Pro Pro Leu Tyr Ser Leu Val Phe Val Ile Gly
                35                  40                  45
Leu Val Gly Asn Ile Leu Val Val Leu Val Leu Val Gln Tyr Lys Arg
 50                  55                  60
Leu Lys Asn Met Thr Ser Ile Tyr Leu Leu Asn Leu Ala Ile Ser Asp
 65                  70                  75                  80
Leu Leu Phe Leu Phe Thr Leu Pro Phe Trp Ile Asp Tyr Lys Leu Lys
                85                  90                  95
Asp Asp Trp Val Phe Gly Asp Ala Met Cys Lys Ile Leu Ser Gly Phe
            100                 105                 110
Tyr Tyr Thr Gly Leu Tyr Ser Glu Ile Phe Phe Ile Ile Leu Leu Thr
            115                 120                 125
Ile Asp Arg Tyr Leu Ala Ile Val His Ala Val Phe Ala Leu Arg Ala
    130                 135                 140
Arg Thr Val Thr Phe Gly Val Ile Thr Ser Ile Ile Trp Ala Leu
145                 150                 155                 160
Ala Ile Leu Ala Ser Met Pro Gly Leu Tyr Phe Ser Lys Thr Gln Trp
                165                 170                 175
Glu Phe Thr His His Thr Cys Ser Leu His Phe Pro His Glu Ser Leu
            180                 185                 190
Arg Glu Trp Lys Leu Phe Gln Ala Leu Lys Leu Asn Leu Phe Gly Leu
        195                 200                 205
Val Leu Pro Leu Leu Val Met Ile Ile Cys Tyr Thr Gly Ile Ile Lys
            210                 215                 220
Ile Leu Leu Arg Arg Pro Asn Glu Lys Lys Ser Lys Ala Val Arg Leu
225                 230                 235                 240
Ile Phe Val Ile Met Ile Ile Phe Phe Leu Phe Trp Thr Pro Tyr Asn
                245                 250                 255
Leu Thr Ile Leu Ile Ser Val Phe Gln Asp Phe Leu Phe Thr His Glu
            260                 265                 270
Cys Glu Gln Ser Arg His Leu Asp Leu Ala Val Gln Val Thr Glu Val
        275                 280                 285
Ile Ala Tyr Thr His Cys Cys Val Asn Pro Val Ile Tyr Ala Phe Val
        290                 295                 300
Gly Glu Arg Phe Arg Lys Tyr Leu Arg Gln Leu Phe His Arg Arg Val
305                 310                 315                 320
Ala Val His Leu Val Lys Trp Leu Pro Phe Leu Ser Val Asp Arg Leu
                325                 330                 335
Glu Arg Val Ser Ser Thr Ser Pro Ser Thr Gly Glu His Glu Leu Ser
            340                 345                 350
Ala Gly Phe
        355

<210> SEQ ID NO 15
<211> LENGTH: 96
<212> TYPE: PRT
<213> ORGANISM: Mus musculus

<400> SEQUENCE: 15

Met Pro Lys Arg Lys Val Ser Ala Asp Gly Ala Ala Lys Ala Glu Pro
  1               5                  10                  15
Lys Arg Arg Ser Ala Arg Leu Ser Ala Lys Pro Ala Pro Ala Lys Val
                20                  25                  30
```

Asp Ala Lys Pro Lys Lys Ala Ala Gly Lys Asp Lys Ala Ser Asp Lys
         35                  40                  45

Lys Val Gln Ile Lys Gly Lys Arg Gly Ala Lys Gly Lys Gln Ala Asp
 50                  55                  60

Val Ala Asp Gln Gln Thr Thr Glu Leu Pro Ala Glu Asn Gly Glu Thr
 65                  70                  75                  80

Glu Asn Gln Ser Pro Ala Ser Glu Glu Lys Glu Ala Lys Ser Asp
                 85                  90                  95

<210> SEQ ID NO 16
<211> LENGTH: 100
<212> TYPE: PRT
<213> ORGANISM: Homo sapiens

<400> SEQUENCE: 16

Met Pro Lys Arg Lys Val Ser Ser Ala Glu Gly Ala Ala Lys Glu Glu
 1               5                  10                  15

Pro Lys Arg Arg Ser Ala Arg Leu Ser Ala Lys Pro Ala Pro Lys Val
                 20                  25                  30

Glu Ala Lys Pro Lys Lys Ala Ala Lys Asp Lys Ser Ser Asp Lys
         35                  40                  45

Lys Val Gln Thr Lys Gly Lys Arg Gly Ala Lys Gly Lys Gln Ala Glu
 50                  55                  60

Val Ala Asn Gln Glu Thr Lys Glu Asp Leu Pro Ala Glu Asn Gly Glu
 65                  70                  75                  80

Thr Lys Thr Glu Glu Ser Pro Ala Ser Asp Glu Ala Gly Glu Lys Glu
                 85                  90                  95

Ala Lys Ser Asp
         100

<210> SEQ ID NO 17
<211> LENGTH: 70
<212> TYPE: PRT
<213> ORGANISM: Mus musculus

<400> SEQUENCE: 17

Met Ser Glu Lys Lys Gln Pro Val Asp Leu Gly Leu Leu Glu Glu Asp
 1               5                  10                  15

Asp Glu Phe Glu Glu Phe Pro Ala Glu Asp Trp Ala Gly Leu Asp Glu
                 20                  25                  30

Asp Glu Asp Ala His Val Trp Glu Asp Asn Trp Asp Asp Asp Asn Val
         35                  40                  45

Glu Asp Asp Phe Ser Asn Gln Leu Arg Ala Glu Leu Glu Lys His Gly
 50                  55                  60

Tyr Lys Met Glu Thr Ser
 65                  70

<210> SEQ ID NO 18
<211> LENGTH: 70
<212> TYPE: PRT
<213> ORGANISM: Homo sapiens

<400> SEQUENCE: 18

Met Ser Glu Lys Lys Gln Pro Val Asp Leu Gly Leu Leu Glu Glu Asp
 1               5                  10                  15

Asp Glu Phe Glu Glu Phe Pro Ala Glu Asp Trp Ala Gly Leu Asp Glu
                 20                  25                  30

Asp Glu Asp Ala His Val Trp Glu Asp Asn Trp Asp Asp Asp Asn Val

```
            35                  40                  45
Glu Asp Asp Phe Ser Asn Gln Leu Arg Ala Glu Leu Glu Lys His Gly
        50                  55                  60
Tyr Lys Met Glu Thr Ser
 65                  70

<210> SEQ ID NO 19
<211> LENGTH: 596
<212> TYPE: PRT
<213> ORGANISM: Mus musculus

<400> SEQUENCE: 19

Met Thr Ser Pro Ser Pro Arg Ile Gln Ile Ile Ser Thr Asp Ser Ala
 1               5                  10                  15

Val Ala Ser Pro Gln Arg Ile Gln Ile Val Thr Asp Gln Gln Thr Gly
                20                  25                  30

Gln Lys Ile Gln Ile Val Thr Ala Val Asp Ala Ser Gly Ser Ser Lys
            35                  40                  45

Gln Gln Phe Ile Leu Thr Ser Pro Asp Gly Ala Gly Thr Gly Lys Val
        50                  55                  60

Ile Leu Ala Ser Pro Glu Thr Ser Ser Ala Lys Gln Leu Ile Phe Thr
 65                  70                  75                  80

Thr Ser Asp Asn Leu Val Pro Gly Arg Ile Gln Ile Val Thr Asp Ser
                85                  90                  95

Ala Ser Val Glu Arg Leu Leu Gly Lys Ala Asp Val Gln Arg Pro Gln
                100                 105                 110

Val Val Glu Tyr Cys Val Val Cys Gly Asp Lys Ala Ser Gly Arg His
            115                 120                 125

Tyr Gly Ala Val Ser Cys Glu Gly Cys Lys Gly Phe Phe Lys Arg Ser
        130                 135                 140

Val Arg Lys Asn Leu Thr Tyr Ser Cys Arg Ser Ser Gln Asp Cys Ile
145                 150                 155                 160

Ile Asn Lys His His Arg Asn Arg Cys Gln Phe Cys Arg Leu Lys Lys
                165                 170                 175

Cys Leu Glu Met Gly Met Lys Met Glu Ser Val Gln Ser Glu Arg Lys
                180                 185                 190

Pro Phe Asp Val Gln Arg Glu Lys Pro Ser Asn Cys Ala Ala Ser Thr
            195                 200                 205

Glu Lys Ile Tyr Ile Arg Lys Asp Leu Arg Ser Pro Leu Ile Ala Thr
        210                 215                 220

Pro Thr Phe Val Ala Asp Lys Asp Gly Ala Arg Gln Thr Gly Leu Leu
225                 230                 235                 240

Asp Pro Gly Met Leu Val Asn Ile Gln Gln Pro Leu Ile Arg Glu Asp
                245                 250                 255

Gly Thr Val Leu Leu Ala Ala Asp Ser Lys Ala Glu Thr Ser Gln Gly
                260                 265                 270

Ala Leu Gly Thr Leu Ala Asn Val Val Thr Ser Leu Ala Asn Leu Ser
            275                 280                 285

Glu Ser Leu Asn Asn Gly Asp Ala Ser Glu Met Gln Pro Glu Asp Gln
        290                 295                 300

Ser Ala Ser Glu Ile Thr Arg Ala Phe Asp Thr Leu Ala Lys Ala Leu
305                 310                 315                 320

Asn Thr Thr Asp Ser Ala Ser Pro Pro Ser Leu Ala Asp Gly Ile Asp
                325                 330                 335
```

```
Ala Ser Gly Gly Gly Ser Ile His Val Ile Ser Arg Asp Gln Ser Thr
            340                 345                 350

Pro Ile Ile Glu Val Glu Gly Pro Leu Leu Ser Asp Thr His Val Thr
            355                 360                 365

Phe Lys Leu Thr Met Pro Ser Pro Met Pro Glu Tyr Leu Asn Val His
            370                 375                 380

Tyr Ile Cys Glu Ser Ala Ser Arg Leu Leu Phe Leu Ser Met His Trp
385                 390                 395                 400

Ala Arg Ser Ile Pro Ala Phe Gln Ala Leu Gly Gln Asp Cys Asn Thr
                405                 410                 415

Ser Leu Val Arg Ala Cys Trp Asn Glu Leu Phe Thr Leu Gly Leu Ala
                420                 425                 430

Gln Cys Ala Gln Val Met Ser Leu Ser Thr Ile Leu Ala Ala Ile Val
            435                 440                 445

Asn His Leu Gln Asn Ser Ile Gln Glu Asp Lys Leu Ser Gly Asp Arg
            450                 455                 460

Ile Lys Gln Val Met Glu His Ile Trp Lys Leu Gln Glu Phe Cys Asn
465                 470                 475                 480

Ser Met Ala Lys Leu Asp Ile Asp Gly Tyr Glu Tyr Ala Tyr Leu Lys
                485                 490                 495

Ala Ile Val Leu Phe Ser Pro Asp His Pro Gly Leu Thr Gly Thr Ser
            500                 505                 510

Gln Ile Glu Lys Phe Gln Glu Lys Ala Gln Met Glu Leu Gln Asp Tyr
            515                 520                 525

Val Gln Lys Thr Tyr Ser Glu Asp Thr Tyr Arg Leu Ala Arg Ile Leu
            530                 535                 540

Val Arg Leu Pro Ala Leu Arg Leu Met Ser Ser Asn Ile Thr Glu Glu
545                 550                 555                 560

Leu Phe Phe Thr Gly Leu Ile Gly Asn Val Ser Ile Asp Ser Ile Ile
                565                 570                 575

Pro Tyr Ile Leu Lys Met Glu Thr Ala Glu Tyr Asn Gly Gln Ile Thr
                580                 585                 590

Gly Ala Ser Leu
            595

<210> SEQ ID NO 20
<211> LENGTH: 596
<212> TYPE: PRT
<213> ORGANISM: Homo sapiens

<400> SEQUENCE: 20

Met Thr Ser Pro Ser Pro Arg Ile Gln Ile Ser Thr Asp Ser Ala
 1               5                  10                  15

Val Ala Ser Pro Gln Arg Ile Gln Ile Val Thr Asp Gln Gln Thr Gly
                20                  25                  30

Gln Lys Ile Gln Ile Val Thr Ala Val Asp Ala Ser Gly Ser Pro Lys
            35                  40                  45

Gln Gln Phe Ile Leu Thr Ser Pro Asp Gly Ala Gly Thr Gly Lys Val
            50                  55                  60

Ile Leu Ala Ser Pro Glu Thr Ser Ser Ala Lys Gln Leu Ile Phe Thr
65                  70                  75                  80

Thr Ser Asp Asn Leu Val Pro Gly Arg Ile Gln Ile Val Thr Asp Ser
                85                  90                  95

Ala Ser Val Glu Arg Leu Leu Gly Lys Thr Asp Val Gln Arg Pro Gln
                100                 105                 110
```

```
Val Val Glu Tyr Cys Val Val Cys Gly Asp Lys Ala Ser Gly Arg His
            115                 120                 125

Tyr Gly Ala Val Ser Cys Glu Gly Cys Lys Gly Phe Phe Lys Arg Ser
        130                 135                 140

Val Arg Lys Asn Leu Thr Tyr Ser Cys Arg Ser Asn Gln Asp Cys Ile
145                 150                 155                 160

Ile Asn Lys His His Arg Asn Arg Cys Gln Phe Cys Arg Leu Lys Lys
                165                 170                 175

Cys Leu Glu Met Gly Met Lys Met Glu Ser Val Gln Ser Glu Arg Lys
            180                 185                 190

Pro Phe Asp Val Gln Arg Glu Lys Pro Ser Asn Cys Ala Ala Ser Thr
            195                 200                 205

Glu Lys Ile Tyr Ile Arg Lys Asp Leu Arg Ser Pro Leu Ile Ala Thr
            210                 215                 220

Pro Thr Phe Val Ala Asp Lys Asp Gly Ala Arg Gln Thr Gly Leu Leu
225                 230                 235                 240

Asp Pro Gly Met Leu Val Asn Ile Gln Gln Pro Leu Ile Arg Glu Asp
                245                 250                 255

Gly Thr Val Leu Leu Ala Thr Asp Ser Lys Ala Glu Thr Ser Gln Gly
            260                 265                 270

Ala Leu Gly Thr Leu Ala Asn Val Val Thr Ser Leu Ala Asn Leu Ser
            275                 280                 285

Glu Ser Leu Asn Asn Gly Asp Thr Ser Glu Ile Gln Pro Glu Asp Gln
            290                 295                 300

Ser Ala Ser Glu Ile Thr Arg Ala Phe Asp Thr Leu Ala Lys Ala Leu
305                 310                 315                 320

Asn Thr Thr Asp Ser Ser Ser Pro Ser Leu Ala Asp Gly Ile Asp
                325                 330                 335

Thr Ser Gly Gly Gly Ser Ile His Val Ile Ser Arg Asp Gln Ser Thr
            340                 345                 350

Pro Ile Ile Glu Val Glu Gly Pro Leu Leu Ser Asp Thr His Val Thr
            355                 360                 365

Phe Lys Leu Thr Met Pro Ser Pro Met Pro Glu Tyr Leu Asn Val His
            370                 375                 380

Tyr Ile Cys Glu Ser Ala Ser Arg Leu Leu Phe Leu Ser Met His Trp
385                 390                 395                 400

Ala Arg Ser Ile Pro Ala Phe Gln Ala Leu Gly Gln Asp Cys Asn Thr
                405                 410                 415

Ser Leu Val Arg Ala Cys Trp Asn Glu Leu Phe Thr Leu Gly Leu Ala
            420                 425                 430

Gln Cys Ala Gln Val Met Ser Leu Ser Thr Ile Leu Ala Ala Ile Val
            435                 440                 445

Asn His Leu Gln Asn Ser Ile Gln Glu Asp Lys Leu Ser Gly Asp Arg
            450                 455                 460

Ile Lys Gln Val Met Glu His Ile Trp Lys Leu Gln Glu Phe Cys Asn
465                 470                 475                 480

Ser Met Ala Lys Leu Asp Ile Asp Gly Tyr Glu Tyr Ala Tyr Leu Lys
                485                 490                 495

Ala Ile Val Leu Phe Ser Pro Asp His Pro Gly Leu Thr Ser Thr Ser
            500                 505                 510

Gln Ile Glu Lys Phe Gln Glu Lys Ala Gln Met Glu Leu Gln Asp Tyr
            515                 520                 525
```

```
Val Gln Lys Thr Tyr Ser Glu Asp Thr Tyr Arg Leu Ala Arg Ile Leu
        530                 535                 540

Val Arg Leu Pro Ala Leu Arg Leu Met Ser Ser Asn Ile Thr Glu Glu
545                 550                 555                 560

Leu Phe Phe Thr Gly Leu Ile Gly Asn Val Ser Ile Asp Ser Ile Ile
                565                 570                 575

Pro Tyr Ile Leu Lys Met Glu Thr Ala Glu Tyr Asn Gly Gln Ile Thr
                580                 585                 590

Gly Ala Ser Leu
            595

<210> SEQ ID NO 21
<211> LENGTH: 97
<212> TYPE: PRT
<213> ORGANISM: Mus musculus

<400> SEQUENCE: 21

Met Arg Ile Ser Ala Thr Leu Leu Cys Leu Leu Leu Ile Ala Ala Ala
1               5                   10                  15

Phe Ser Ile Gln Val Trp Ala Gln Pro Asp Gly Pro Asn Ala Ser Thr
            20                  25                  30

Cys Cys Tyr Val Lys Lys Gln Lys Ile Pro Lys Arg Asn Leu Lys Ser
        35                  40                  45

Tyr Arg Arg Ile Thr Ser Ser Arg Cys Pro Trp Glu Ala Val Ile Phe
    50                  55                  60

Lys Thr Lys Lys Gly Met Glu Val Cys Ala Glu Ala His Gln Lys Trp
65                  70                  75                  80

Val Glu Glu Ala Ile Ala Tyr Leu Asp Met Lys Thr Pro Thr Pro Lys
                85                  90                  95

Pro

<210> SEQ ID NO 22
<211> LENGTH: 99
<212> TYPE: PRT
<213> ORGANISM: Homo sapiens

<400> SEQUENCE: 22

Met Lys Ala Ser Ala Ala Leu Leu Cys Leu Leu Leu Thr Ala Ala Ala
1               5                   10                  15

Phe Ser Pro Gln Gly Leu Ala Gln Pro Val Gly Ile Asn Thr Ser Thr
            20                  25                  30

Thr Cys Cys Tyr Arg Phe Ile Asn Lys Lys Ile Pro Lys Gln Arg Leu
        35                  40                  45

Glu Ser Tyr Arg Arg Thr Thr Ser Ser His Cys Pro Arg Glu Ala Val
    50                  55                  60

Ile Phe Lys Thr Lys Leu Asp Lys Glu Ile Cys Ala Asp Pro Thr Gln
65                  70                  75                  80

Lys Trp Val Gln Asp Phe Met Lys His Leu Asp Lys Lys Thr Gln Thr
                85                  90                  95

Pro Lys Leu

<210> SEQ ID NO 23
<211> LENGTH: 415
<212> TYPE: PRT
<213> ORGANISM: Mus musculus

<400> SEQUENCE: 23
```

-continued

```
Met Val Pro Val Leu Leu Ile Leu Val Gly Ala Leu Ala Thr Leu Gln
1               5                   10                  15

Ala Asp Leu Leu Asn His Lys Lys Phe Leu Leu Pro Pro Val Asn
        20                  25                  30

Phe Thr Ile Lys Ala Thr Gly Leu Ala Gln Val Leu Leu His Trp Asp
            35                  40                  45

Pro Asn Pro Asp Gln Glu Gln Arg His Val Asp Leu Glu Tyr His Val
    50                  55                  60

Lys Ile Asn Ala Pro Gln Glu Asp Glu Tyr Asp Thr Arg Lys Thr Glu
65                  70                  75                  80

Ser Lys Cys Val Thr Pro Leu His Glu Gly Phe Ala Ala Ser Val Arg
                85                  90                  95

Thr Ile Leu Lys Ser Ser His Thr Thr Leu Ala Ser Ser Trp Val Ser
                100                 105                 110

Ala Glu Leu Lys Ala Pro Pro Gly Ser Pro Gly Thr Ser Val Thr Asn
            115                 120                 125

Leu Thr Cys Thr Thr His Thr Val Val Ser Ser His Thr His Leu Arg
    130                 135                 140

Pro Tyr Gln Val Ser Leu Arg Cys Thr Trp Leu Val Gly Lys Asp Ala
145                 150                 155                 160

Pro Glu Asp Thr Gln Tyr Phe Leu Tyr Tyr Arg Phe Gly Val Leu Thr
                165                 170                 175

Glu Lys Cys Gln Glu Tyr Ser Arg Asp Ala Leu Asn Arg Asn Thr Ala
            180                 185                 190

Cys Trp Phe Pro Arg Thr Phe Ile Asn Ser Lys Gly Phe Glu Gln Leu
        195                 200                 205

Ala Val His Ile Asn Gly Ser Ser Lys Arg Ala Ala Ile Lys Pro Phe
210                 215                 220

Asp Gln Leu Phe Ser Pro Leu Ala Ile Asp Gln Val Asn Pro Pro Arg
225                 230                 235                 240

Asn Val Thr Val Glu Ile Glu Ser Asn Ser Leu Tyr Ile Gln Trp Glu
                245                 250                 255

Lys Pro Leu Ser Ala Phe Pro Asp His Cys Phe Asn Tyr Glu Leu Lys
            260                 265                 270

Ile Tyr Asn Thr Lys Asn Gly His Ile Gln Lys Glu Lys Leu Ile Ala
        275                 280                 285

Asn Lys Phe Ile Ser Lys Ile Asp Asp Val Ser Thr Tyr Ser Ile Gln
    290                 295                 300

Val Arg Ala Ala Val Ser Ser Pro Cys Arg Met Pro Gly Arg Trp Gly
305                 310                 315                 320

Glu Trp Ser Gln Pro Ile Tyr Val Gly Lys Glu Arg Lys Ser Leu Val
                325                 330                 335

Glu Trp His Leu Ile Val Leu Pro Thr Ala Ala Cys Phe Val Leu Leu
            340                 345                 350

Ile Phe Ser Leu Ile Cys Arg Val Cys His Leu Trp Thr Arg Leu Phe
        355                 360                 365

Pro Pro Val Pro Ala Pro Lys Ser Asn Ile Lys Asp Leu Pro Val Val
    370                 375                 380

Thr Glu Tyr Glu Lys Pro Ser Asn Glu Thr Lys Ile Glu Val Val His
385                 390                 395                 400

Cys Val Glu Glu Val Gly Phe Glu Val Met Gly Asn Ser Thr Phe
                405                 410                 415
```

-continued

```
<210> SEQ ID NO 24
<211> LENGTH: 420
<212> TYPE: PRT
<213> ORGANISM: Homo sapiens

<400> SEQUENCE: 24

Met Ile Ile Val Ala His Val Leu Leu Ile Leu Leu Gly Ala Thr Glu
 1               5                  10                  15

Ile Leu Gln Ala Asp Leu Leu Pro Asp Glu Lys Ile Ser Leu Leu Pro
            20                  25                  30

Pro Val Asn Phe Thr Ile Lys Val Thr Gly Leu Ala Gln Val Leu Leu
        35                  40                  45

Gln Trp Lys Pro Asn Pro Asp Gln Glu Gln Arg Asn Val Asn Leu Glu
 50                  55                  60

Tyr Gln Val Lys Ile Asn Ala Pro Lys Glu Asp Asp Tyr Glu Thr Arg
 65                  70                  75                  80

Ile Thr Glu Ser Lys Cys Val Thr Ile Leu His Lys Gly Phe Ser Ala
                85                  90                  95

Ser Val Arg Thr Ile Leu Gln Asn Asp His Ser Leu Leu Ala Ser Ser
            100                 105                 110

Trp Ala Ser Ala Glu Leu His Ala Pro Pro Gly Ser Pro Gly Thr Ser
        115                 120                 125

Ile Val Asn Leu Thr Cys Thr Thr Asn Thr Thr Glu Asp Asn Tyr Ser
130                 135                 140

Arg Leu Arg Ser Tyr Gln Val Ser Leu His Cys Thr Trp Leu Val Gly
145                 150                 155                 160

Thr Asp Ala Pro Glu Asp Thr Gln Tyr Phe Leu Tyr Tyr Arg Tyr Gly
                165                 170                 175

Ser Trp Thr Glu Glu Cys Gln Glu Tyr Ser Lys Asp Thr Leu Gly Arg
            180                 185                 190

Asn Ile Ala Cys Trp Phe Pro Arg Thr Phe Ile Leu Ser Lys Gly Arg
        195                 200                 205

Asp Trp Leu Ser Val Leu Val Asn Gly Ser Ser Lys His Ser Ala Ile
    210                 215                 220

Arg Pro Phe Asp Gln Leu Phe Ala Leu His Ala Ile Asp Gln Ile Asn
225                 230                 235                 240

Pro Pro Leu Asn Val Thr Ala Glu Ile Glu Gly Thr Arg Leu Ser Ile
                245                 250                 255

Gln Trp Glu Lys Pro Val Ser Ala Phe Pro Ile His Cys Phe Asp Tyr
            260                 265                 270

Glu Val Lys Ile His Asn Thr Arg Asn Gly Tyr Leu Gln Ile Glu Lys
        275                 280                 285

Leu Met Thr Asn Ala Phe Ile Ser Ile Ile Asp Asp Leu Ser Lys Tyr
    290                 295                 300

Asp Val Gln Val Arg Ala Ala Val Ser Ser Met Cys Arg Glu Ala Gly
305                 310                 315                 320

Leu Trp Ser Glu Trp Ser Gln Pro Ile Tyr Val Gly Asn Asp Glu His
                325                 330                 335

Lys Pro Leu Arg Glu Trp Phe Val Ile Val Met Ala Thr Ile Cys
            340                 345                 350

Phe Ile Leu Leu Ile Leu Ser Leu Ile Cys Lys Ile Cys His Leu Trp
        355                 360                 365

Ile Lys Leu Phe Pro Pro Ile Pro Ala Pro Lys Ser Asn Ile Lys Asp
    370                 375                 380
```

Leu Phe Val Thr Thr Asn Tyr Glu Lys Ala Gly Ser Ser Glu Thr Glu
385                 390                 395                 400

Ile Glu Val Ile Cys Tyr Ile Glu Lys Pro Gly Val Glu Thr Leu Glu
                405                 410                 415

Asp Ser Val Phe
            420

<210> SEQ ID NO 25
<211> LENGTH: 113
<212> TYPE: PRT
<213> ORGANISM: Mus musculus

<400> SEQUENCE: 25

Met Ser Ala Ser Val Val Ser Val Ile Ser Arg Phe Leu Glu Glu Tyr
1               5                   10                  15

Leu Ser Ser Thr Pro Gln Arg Leu Lys Leu Leu Asp Gly Tyr Leu Leu
                20                  25                  30

Tyr Ile Leu Leu Thr Gly Ala Leu Gln Phe Gly Tyr Cys Leu Leu Val
                35                  40                  45

Gly Thr Phe Pro Phe Asn Ser Phe Leu Ser Gly Phe Ile Ser Cys Val
    50                  55                  60

Gly Ser Phe Ile Leu Ala Val Cys Leu Arg Ile Gln Ile Asn Pro Gln
65                  70                  75                  80

Asn Lys Ala Asp Phe Gln Gly Ile Ser Pro Glu Arg Ala Phe Ala Asp
                85                  90                  95

Phe Leu Phe Gly Ser Thr Ile Leu His Leu Val Val Met Asn Phe Val
                100                 105                 110

Gly

<210> SEQ ID NO 26
<211> LENGTH: 113
<212> TYPE: PRT
<213> ORGANISM: Homo sapiens

<400> SEQUENCE: 26

Met Ser Ala Ser Val Val Ser Val Ile Ser Arg Phe Leu Glu Glu Tyr
1               5                   10                  15

Leu Ser Ser Thr Pro Gln Arg Leu Lys Leu Leu Asp Ala Tyr Leu Leu
                20                  25                  30

Tyr Ile Leu Leu Thr Gly Ala Leu Gln Phe Gly Tyr Cys Leu Leu Val
                35                  40                  45

Gly Thr Phe Pro Phe Asn Ser Phe Leu Ser Gly Phe Ile Ser Cys Val
    50                  55                  60

Gly Ser Phe Ile Leu Ala Val Cys Leu Arg Ile Gln Ile Asn Pro Gln
65                  70                  75                  80

Asn Lys Ala Asp Phe Gln Gly Ile Ser Pro Glu Arg Ala Phe Ala Asp
                85                  90                  95

Phe Leu Phe Ala Ser Thr Ile Leu His Leu Val Val Met Asn Phe Val
                100                 105                 110

Gly

<210> SEQ ID NO 27
<211> LENGTH:
<212> TYPE:
<213> ORGANISM:

<400> SEQUENCE: 27

000

<210> SEQ ID NO 28
<211> LENGTH:
<212> TYPE:
<213> ORGANISM:

<400> SEQUENCE: 28

000

<210> SEQ ID NO 29
<211> LENGTH: 97
<212> TYPE: PRT
<213> ORGANISM: Mus musculus

<400> SEQUENCE: 29

```
Met Lys Ile Tyr Ala Val Leu Leu Cys Leu Leu Leu Ile Ala Val Pro
  1               5                  10                  15

Val Ser Pro Glu Lys Leu Thr Gly Pro Asp Lys Ala Pro Val Thr Cys
              20                  25                  30

Cys Phe His Val Leu Lys Leu Lys Ile Pro Leu Arg Val Leu Lys Ser
          35                  40                  45

Tyr Glu Arg Ile Asn Asn Ile Gln Cys Pro Met Glu Ala Val Val Phe
     50                  55                  60

Gln Thr Lys Gln Gly Met Ser Leu Cys Val Asp Pro Thr Gln Lys Trp
 65                  70                  75                  80

Val Ser Glu Tyr Met Glu Ile Leu Asp Gln Lys Ser Gln Ile Leu Gln
                 85                  90                  95

Pro
```

SEQ ID NO 30
LENGTH: 99
TYPE: PRT
ORGANISM: Homo sapiens

SEQUENCE: 30

```
Met Lys Val Ser Ala Ala Leu Leu Cys Leu Leu Leu Met Ala Ala Thr
  1               5                  10                  15

Phe Ser Pro Gln Gly Leu Ala Gln Pro Asp Ser Val Ser Ile Pro Ile
              20                  25                  30

Thr Cys Cys Phe Asn Val Ile Asn Arg Lys Ile Pro Ile Gln Arg Leu
          35                  40                  45

Glu Ser Tyr Thr Arg Ile Thr Asn Ile Gln Cys Pro Lys Glu Ala Val
     50                  55                  60

Ile Phe Lys Thr Gln Arg Gly Lys Glu Val Cys Ala Asp Pro Lys Glu
 65                  70                  75                  80

Arg Trp Val Arg Asp Ser Met Lys His Leu Asp Gln Ile Phe Gln Asn
                 85                  90                  95

Leu Lys Pro
```

<210> SEQ ID NO 31
<211> LENGTH: 411
<212> TYPE: PRT
<213> ORGANISM: Mus musculus

<400> SEQUENCE: 31

```
Met Ser Lys Arg Pro Ser Tyr Ala Pro Pro Thr Pro Ala Pro Ala
  1               5                  10                  15
```

```
Thr Gln Met Pro Ser Thr Pro Gly Phe Val Gly Tyr Asn Pro Tyr Ser
            20                  25                  30

His Leu Ala Tyr Asn Asn Tyr Arg Leu Gly Gly Asn Pro Gly Thr Asn
        35                  40                  45

Ser Arg Val Thr Ala Ser Ser Gly Ile Thr Ile Pro Lys Pro Pro Lys
50                  55                  60

Pro Pro Asp Lys Pro Leu Met Pro Tyr Met Arg Tyr Ser Arg Lys Val
65                  70                  75                  80

Trp Asp Gln Val Lys Ala Ser Asn Pro Asp Leu Lys Leu Trp Glu Ile
                85                  90                  95

Gly Lys Ile Ile Gly Gly Met Trp Arg Asp Leu Thr Asp Glu Glu Lys
                100                 105                 110

Gln Glu Tyr Leu Asn Glu Tyr Glu Ala Glu Lys Ile Glu Tyr Asn Glu
            115                 120                 125

Ser Met Lys Ala Tyr His Asn Ser Pro Ala Tyr Leu Ala Tyr Ile Asn
        130                 135                 140

Ala Lys Ser Arg Ala Glu Ala Ala Leu Glu Glu Glu Ser Arg Gln Arg
145                 150                 155                 160

Gln Ser Arg Met Glu Lys Gly Glu Pro Tyr Met Ser Ile Gln Pro Ala
                165                 170                 175

Glu Asp Pro Asp Asp Tyr Asp Asp Gly Phe Ser Met Lys His Thr Ala
                180                 185                 190

Thr Ala Arg Phe Gln Arg Asn His Arg Leu Ile Ser Glu Ile Leu Ser
            195                 200                 205

Glu Ser Val Val Pro Asp Val Arg Ser Val Val Thr Thr Ala Arg Met
210                 215                 220

Gln Val Leu Lys Arg Gln Val Gln Ser Leu Met Val His Gln Arg Lys
225                 230                 235                 240

Leu Glu Ala Glu Leu Leu Gln Ile Glu Glu Arg His Gln Glu Lys Lys
                245                 250                 255

Arg Lys Phe Leu Glu Ser Thr Asp Ser Phe Asn Asn Glu Leu Lys Arg
            260                 265                 270

Leu Cys Gly Leu Lys Val Glu Val Asp Met Glu Lys Ile Ala Ala Glu
        275                 280                 285

Ile Ala Gln Ala Glu Glu Gln Ala Arg Lys Arg Gln Glu Glu Arg Glu
    290                 295                 300

Lys Glu Ala Ala Glu Gln Ala Glu Arg Ser Gln Ser Ser Met Ala Pro
305                 310                 315                 320

Glu Glu Glu Gln Val Ala Asn Lys Ala Glu Lys Lys Asp Glu Glu
                325                 330                 335

Ser Ile Pro Met Glu Thr Glu Glu Thr His Leu Glu Asp Thr Ala Glu
                340                 345                 350

Ser Gln Gln Asn Gly Glu Glu Gly Thr Ser Thr Pro Glu Asp Lys Glu
            355                 360                 365

Ser Gly Gln Glu Gly Val Asp Ser Met Glu Val Glu Gly Thr Ser Asp
        370                 375                 380

Ser Asn Thr Gly Ser Glu Ser Asn Ser Ala Thr Val Glu Glu Pro Pro
385                 390                 395                 400

Thr Asp Pro Val Pro Glu Asp Glu Lys Lys Glu
                405                 410

<210> SEQ ID NO 32
<211> LENGTH: 411
```

-continued

```
<212> TYPE: PRT
<213> ORGANISM: Homo sapiens

<400> SEQUENCE: 32

Met Ser Lys Arg Pro Ser Tyr Ala Pro Pro Thr Pro Ala Pro Ala
1               5                  10                  15

Thr Gln Met Pro Ser Thr Pro Gly Phe Val Gly Tyr Asn Pro Tyr Ser
            20                  25                  30

His Leu Ala Tyr Asn Asn Tyr Arg Leu Gly Gly Asn Pro Gly Thr Asn
        35                  40                  45

Ser Arg Val Thr Ala Ser Ser Gly Ile Thr Ile Pro Lys Pro Pro Lys
    50                  55                  60

Pro Pro Asp Lys Pro Leu Met Pro Tyr Met Arg Tyr Ser Arg Lys Val
65              70                  75                  80

Trp Asp Gln Val Lys Ala Ser Asn Pro Asp Leu Lys Leu Trp Glu Ile
                85                  90                  95

Gly Lys Ile Ile Gly Gly Met Trp Arg Asp Leu Thr Asp Glu Lys
                100                 105                 110

Gln Glu Tyr Leu Asn Glu Tyr Glu Ala Glu Lys Ile Glu Tyr Asn Glu
            115                 120                 125

Ser Met Lys Ala Tyr His Asn Ser Pro Ala Tyr Leu Ala Tyr Ile Asn
    130                 135                 140

Ala Lys Ser Arg Ala Glu Ala Ala Leu Glu Glu Ser Arg Gln Arg
145                 150                 155                 160

Gln Ser Arg Met Glu Lys Gly Glu Pro Tyr Met Ser Ile Gln Pro Ala
                165                 170                 175

Glu Asp Pro Asp Asp Tyr Asp Asp Gly Phe Ser Met Lys His Thr Ala
            180                 185                 190

Thr Ala Arg Phe Gln Arg Asn His Arg Leu Ile Ser Glu Ile Leu Ser
        195                 200                 205

Glu Ser Val Val Pro Asp Val Arg Ser Val Val Thr Thr Ala Arg Met
    210                 215                 220

Gln Val Leu Lys Arg Gln Val Gln Ser Leu Met Val His Gln Arg Lys
225                 230                 235                 240

Leu Glu Ala Glu Leu Leu Gln Ile Glu Glu Arg His Gln Glu Lys Lys
                245                 250                 255

Arg Lys Phe Leu Glu Ser Thr Asp Ser Phe Asn Asn Glu Leu Lys Arg
            260                 265                 270

Leu Cys Gly Leu Lys Val Glu Val Asp Met Glu Lys Ile Ala Ala Glu
        275                 280                 285

Ile Ala Gln Ala Glu Glu Gln Ala Arg Lys Arg Gln Glu Glu Arg Glu
    290                 295                 300

Lys Glu Ala Ala Glu Gln Ala Glu Arg Ser Gln Ser Ser Ile Val Pro
305                 310                 315                 320

Glu Glu Glu Gln Ala Ala Asn Lys Gly Glu Glu Lys Lys Asp Asp Glu
                325                 330                 335

Asn Ile Pro Met Glu Thr Glu Thr His Leu Glu Glu Thr Thr Glu
            340                 345                 350

Ser Gln Gln Asn Gly Glu Glu Gly Thr Ser Thr Pro Glu Asp Lys Glu
        355                 360                 365

Ser Gly Gln Glu Gly Val Asp Ser Met Ala Glu Gly Thr Ser Asp
    370                 375                 380

Ser Asn Thr Gly Ser Glu Ser Asn Ser Ala Thr Val Glu Glu Pro Pro
385                 390                 395                 400
```

```
Thr Asp Pro Ile Pro Glu Asp Glu Lys Lys Glu
                405                 410

<210> SEQ ID NO 33
<211> LENGTH: 821
<212> TYPE: PRT
<213> ORGANISM: Mus musculus

<400> SEQUENCE: 33

Met Asn Gly His Met Ser Asn Arg Ser Ser Gly Tyr Gly Val Tyr Pro
1               5                   10                  15

Ser Gln Leu Asn Gly Tyr Gly Ser Ser Pro Pro Tyr Ser Gln Met Asp
            20                  25                  30

Arg Glu His Ser Ser Arg Thr Ser Ala Lys Ala Leu Tyr Glu Gln Arg
        35                  40                  45

Lys Asn Tyr Ala Arg Asp Ser Val Ser Ser Val Ser Asp Val Ser Gln
    50                  55                  60

Tyr Arg Val Glu His Leu Thr Thr Phe Val Leu Asp Arg Lys Asp Ala
65                  70                  75                  80

Met Ile Thr Val Glu Asp Gly Ile Arg Lys Leu Lys Leu Leu Asp Ala
                85                  90                  95

Lys Gly Lys Val Trp Thr Gln Asp Met Ile Leu Gln Val Asp Asp Arg
            100                 105                 110

Ala Val Ser Leu Ile Asp Leu Glu Ser Lys Asn Glu Leu Glu Asn Phe
        115                 120                 125

Pro Leu Asn Thr Ile Ser His Cys Gln Ala Val Val His Ala Cys Ser
    130                 135                 140

Tyr Asp Ser Ile Leu Ala Leu Val Cys Lys Glu Pro Thr Gln Ser Lys
145                 150                 155                 160

Pro Asp Leu His Leu Phe Gln Cys Asp Glu Val Lys Ala Asn Leu Ile
                165                 170                 175

Ser Glu Asp Ile Glu Ser Ala Ile Ser Asp Ser Lys Gly Gly Lys Gln
            180                 185                 190

Lys Arg Arg Pro Glu Ala Leu Arg Met Ile Ala Lys Ala Asp Pro Gly
        195                 200                 205

Ile Pro Pro Pro Arg Ala Pro Ala Pro Val Pro Pro Gly Thr Val
    210                 215                 220

Thr Gln Val Asp Val Arg Ser Arg Val Ala Ala Trp Ser Ala Trp Ala
225                 230                 235                 240

Ala Asp Gln Gly Asp Phe Glu Lys Pro Arg Gln Tyr His Glu Gln Glu
                245                 250                 255

Glu Thr Pro Glu Met Met Ala Ala Arg Ile Asp Arg Asp Val Gln Ile
            260                 265                 270

Leu Asn His Ile Leu Asp Asp Ile Glu Phe Phe Ile Thr Lys Leu Gln
        275                 280                 285

Lys Ala Ala Glu Ala Phe Ser Glu Leu Ser Lys Arg Lys Lys Ser Lys
    290                 295                 300

Lys Ser Lys Arg Lys Gly Pro Gly Glu Gly Val Leu Thr Leu Arg Ala
305                 310                 315                 320

Lys Pro Pro Pro Pro Asp Glu Phe Val Asp Cys Phe Gln Lys Phe Lys
                325                 330                 335

His Gly Phe Asn Leu Leu Ala Lys Leu Lys Ser His Ile Gln Asn Pro
            340                 345                 350

Ser Ala Ser Asp Leu Val His Phe Leu Phe Thr Pro Leu Asn Met Val
```

-continued

```
            355                 360                 365
Val Gln Ala Thr Gly Gly Pro Glu Leu Ala Ser Ser Val Leu Ser Pro
        370                 375                 380
Leu Leu Thr Lys Asp Thr Val Asp Phe Leu Asn Tyr Thr Ala Thr Ala
385                 390                 395                 400
Glu Glu Arg Lys Leu Trp Met Ser Leu Gly Asp Ser Trp Val Lys Val
                405                 410                 415
Arg Ala Glu Trp Pro Lys Glu Gln Phe Ile Pro Pro Tyr Val Pro Arg
                420                 425                 430
Phe Arg Asn Gly Trp Glu Pro Met Leu Asn Phe Met Gly Ala Pro
                435                 440                 445
Thr Glu Gln Asp Met Tyr Gln Leu Ala Glu Ser Val Ala Asn Ala Glu
        450                 455                 460
His Gln Arg Lys Gln Asp Ser Lys Arg Leu Ser Thr Glu His Ser Asn
465                 470                 475                 480
Val Ser Asp Tyr Pro Pro Ala Asp Gly Tyr Ala Tyr Ser Ser Ser Met
                485                 490                 495
Tyr His Arg Gly Pro His Ala Asp His Gly Glu Ala Ala Met Pro Phe
                500                 505                 510
Lys Ser Thr Pro Asn His Gln Val Asp Arg Asn Tyr Asp Ala Val Lys
                515                 520                 525
Thr Gln Pro Lys Lys Tyr Ala Lys Ser Lys Tyr Asp Phe Val Ala Arg
        530                 535                 540
Asn Ser Ser Glu Leu Ser Val Met Lys Asp Val Leu Glu Ile Leu
545                 550                 555                 560
Asp Asp Arg Arg Gln Trp Trp Lys Val Arg Asn Ala Ser Gly Asp Ser
                565                 570                 575
Gly Phe Val Pro Asn Asn Ile Leu Asp Ile Met Arg Thr Pro Glu Ser
                580                 585                 590
Gly Val Gly Arg Ala Asp Pro Tyr Thr His Thr Ile Gln Lys Gln
                595                 600                 605
Arg Thr Glu Tyr Gly Leu Arg Ser Ala Asp Thr Pro Ser Ala Pro Ser
        610                 615                 620
Pro Pro Pro Thr Pro Ala Pro Val Pro Val Pro Leu Pro Pro Ser Val
625                 630                 635                 640
Pro Ala Pro Val Ser Val Pro Lys Val Pro Ala Asp Val Thr Arg Gln
                645                 650                 655
Asn Ser Ser Ser Ser Asp Ser Gly Gly Ser Ile Val Arg Asp Ser Gln
                660                 665                 670
Arg Tyr Lys Gln Leu Pro Val Asp Arg Arg Lys Ser Gln Met Glu Glu
                675                 680                 685
Val Gln Asp Glu Leu Phe Gln Arg Leu Thr Ile Gly Arg Ser Ala Ala
        690                 695                 700
Gln Arg Lys Phe His Val Pro Arg Gln Asn Val Pro Val Ile Asn Ile
705                 710                 715                 720
Thr Tyr Asp Ser Ser Pro Glu Glu Val Lys Thr Trp Leu Gln Ser Lys
                725                 730                 735
Gly Phe Asn Pro Val Thr Val Asn Ser Leu Gly Val Leu Asn Gly Ala
                740                 745                 750
Gln Leu Phe Ser Leu Asn Lys Asp Glu Leu Arg Ser Val Cys Pro Glu
                755                 760                 765
Gly Ala Arg Val Phe Asn Gln Ile Thr Val Gln Lys Ala Ala Leu Glu
                770                 775                 780
```

```
Asp Ser Asn Gly Ser Ser Glu Leu Gln Glu Ile Met Arg Arg Gln
785                 790                 795                 800

Glu Lys Ile Ser Ala Ala Ala Ser Asp Ser Gly Val Glu Ser Phe Asp
            805                 810                 815

Glu Gly Ser Ser His
            820

<210> SEQ ID NO 34
<211> LENGTH: 822
<212> TYPE: PRT
<213> ORGANISM: Homo sapiens

<400> SEQUENCE: 34

Met Asn Gly His Ile Ser Asn His Pro Ser Ser Phe Gly Met Tyr Pro
1               5                   10                  15

Ser Gln Met Asn Gly Tyr Gly Ser Ser Pro Thr Phe Ser Gln Thr Asp
            20                  25                  30

Arg Glu His Gly Ser Lys Thr Ser Ala Lys Ala Leu Tyr Glu Gln Arg
            35                  40                  45

Lys Asn Tyr Ala Arg Asp Ser Val Ser Val Ser Asp Ile Ser Gln
    50                  55                  60

Tyr Arg Val Glu His Leu Thr Thr Phe Val Leu Asp Arg Lys Asp Ala
65                  70                  75                  80

Met Ile Thr Val Asp Asp Gly Ile Arg Lys Leu Lys Leu Leu Asp Ala
                85                  90                  95

Lys Gly Lys Val Trp Thr Gln Asp Met Ile Leu Gln Val Asp Asp Arg
            100                 105                 110

Ala Val Ser Leu Ile Asp Leu Glu Ser Lys Asn Glu Leu Glu Asn Phe
            115                 120                 125

Pro Leu Asn Thr Ile Gln His Cys Gln Ala Val Met His Ser Cys Ser
    130                 135                 140

Tyr Asp Ser Val Leu Ala Leu Val Cys Lys Glu Pro Thr Gln Asn Lys
145                 150                 155                 160

Pro Asp Leu His Leu Phe Gln Cys Asp Glu Val Lys Ala Asn Leu Ile
                165                 170                 175

Ser Glu Asp Ile Glu Ser Ala Ile Ser Asp Ser Lys Gly Gly Lys Gln
            180                 185                 190

Lys Arg Arg Pro Asp Ala Leu Arg Met Ile Ser Asn Ala Asp Pro Ser
    195                 200                 205

Ile Pro Pro Pro Arg Ala Pro Ala Pro Pro Gly Thr Val
    210                 215                 220

Thr Gln Val Asp Val Arg Ser Arg Val Ala Ala Trp Ser Ala Trp Ala
225                 230                 235                 240

Ala Asp Gln Gly Asp Phe Glu Lys Pro Arg Gln Tyr His Glu Gln Glu
                245                 250                 255

Glu Thr Pro Glu Met Met Ala Ala Arg Ile Asp Arg Asp Val Gln Ile
            260                 265                 270

Leu Asn His Ile Leu Asp Asp Ile Glu Phe Phe Ile Thr Lys Leu Gln
    275                 280                 285

Lys Ala Ala Glu Ala Phe Ser Glu Leu Ser Lys Arg Lys Lys Asn Lys
    290                 295                 300

Lys Gly Lys Arg Lys Gly Pro Gly Glu Gly Val Leu Thr Leu Arg Ala
305                 310                 315                 320

Lys Pro Pro Pro Pro Asp Glu Phe Leu Asp Cys Phe Gln Lys Phe Lys
```

-continued

```
                325                 330                 335
His Gly Phe Asn Leu Leu Ala Lys Leu Lys Ser His Ile Gln Asn Pro
            340                 345                 350

Ser Ala Ala Asp Leu Val His Phe Leu Phe Thr Pro Leu Asn Met Val
            355                 360                 365

Val Gln Ala Thr Gly Gly Pro Glu Leu Ala Ser Ser Val Leu Ser Pro
370                 375                 380

Leu Leu Asn Lys Asp Thr Ile Asp Phe Leu Asn Tyr Thr Val Asn Gly
385                 390                 395                 400

Asp Glu Arg Gln Leu Trp Met Ser Leu Gly Thr Trp Met Lys Ala
                405                 410                 415

Arg Ala Glu Trp Pro Lys Glu Gln Phe Ile Pro Pro Tyr Val Pro Arg
            420                 425                 430

Phe Arg Asn Gly Trp Glu Pro Pro Met Leu Asn Phe Met Gly Ala Thr
            435                 440                 445

Met Glu Gln Asp Leu Tyr Gln Leu Ala Glu Ser Val Ala Asn Val Ala
450                 455                 460

Glu His Gln Arg Lys Gln Glu Ile Lys Arg Leu Ser Thr Glu His Ser
465                 470                 475                 480

Ser Val Ser Glu Tyr His Pro Ala Asp Gly Tyr Ala Phe Ser Ser Asn
            485                 490                 495

Ile Tyr Thr Arg Gly Ser His Leu Asp Gln Gly Glu Ala Ala Val Ala
            500                 505                 510

Phe Lys Pro Thr Ser Asn Arg His Ile Asp Arg Asn Tyr Glu Pro Leu
            515                 520                 525

Lys Thr Gln Pro Lys Lys Tyr Ala Lys Ser Lys Tyr Asp Phe Val Ala
            530                 535                 540

Arg Asn Asn Ser Glu Leu Ser Val Leu Lys Asp Ile Leu Glu Ile
545                 550                 555                 560

Leu Asp Asp Arg Lys Gln Trp Trp Lys Val Arg Asn Ala Ser Gly Asp
                565                 570                 575

Ser Gly Phe Val Pro Asn Asn Ile Leu Asp Ile Val Arg Pro Pro Glu
            580                 585                 590

Ser Gly Leu Gly Arg Ala Asp Pro Tyr Thr His Thr Ile Gln Lys
            595                 600                 605

Gln Arg Met Glu Tyr Gly Pro Arg Pro Ala Asp Thr Pro Ala Pro
            610                 615                 620

Ser Pro Pro Thr Pro Ala Pro Val Pro Val Pro Leu Pro Pro Ser
625                 630                 635                 640

Thr Pro Ala Pro Val Pro Val Ser Lys Val Pro Ala Asn Ile Thr Arg
            645                 650                 655

Gln Asn Ser Ser Ser Asp Ser Gly Gly Ser Ile Val Arg Asp Ser
            660                 665                 670

Gln Arg His Lys Gln Leu Pro Val Asp Arg Lys Ser Gln Met Glu
            675                 680                 685

Glu Val Gln Asp Glu Leu Ile His Arg Leu Thr Ile Gly Arg Ser Ala
            690                 695                 700

Ala Gln Lys Lys Phe His Val Pro Arg Gln Asn Val Pro Val Ile Asn
705                 710                 715                 720

Ile Thr Tyr Asp Ser Thr Pro Glu Asp Val Lys Thr Trp Leu Gln Ser
                725                 730                 735

Lys Gly Phe Asn Pro Val Thr Val Asn Ser Leu Gly Val Leu Asn Gly
                740                 745                 750
```

-continued

```
Ala Gln Leu Phe Ser Leu Asn Lys Asp Glu Leu Arg Thr Val Cys Pro
        755                 760                 765

Glu Gly Ala Arg Val Tyr Ser Gln Ile Thr Val Gln Lys Ala Ala Leu
        770                 775                 780

Glu Asp Ser Ser Gly Ser Ser Glu Leu Gln Glu Ile Met Arg Arg Arg
785                 790                 795                 800

Gln Glu Lys Ile Ser Ala Ala Ser Asp Ser Gly Val Glu Ser Phe
                805                 810                 815

Asp Glu Gly Ser Ser His
            820

<210> SEQ ID NO 35
<211> LENGTH: 470
<212> TYPE: PRT
<213> ORGANISM: Mus musculus
<220> FEATURE:
<221> NAME/KEY: VARIANT
<222> LOCATION: 371
<223> OTHER INFORMATION: Xaa= any amino acid

<400> SEQUENCE: 35

Met Leu Val Glu Thr Gly Glu Leu Asp Asn Thr Tyr Ile Leu Tyr Thr
 1               5                  10                  15

Ala Asp His Gly Tyr His Ile Gly Gln Phe Gly Leu Val Lys Gly Lys
                20                  25                  30

Ser Met Pro Tyr Glu Phe Asp Ile Arg Val Pro Phe Tyr Val Arg Gly
            35                  40                  45

Pro Asn Val Glu Ala Gly Ser Leu Asn Pro His Ile Val Leu Asn Ile
        50                  55                  60

Asp Leu Gly Pro His His Thr Gly Tyr Arg Trp Thr Gly His Pro Cys
65                  70                  75                  80

Arg His Gly Arg Glu Val Tyr Ser Gln Thr Thr Gly Leu Arg Ala Ala
                85                  90                  95

Ser Glu Pro Val Pro Leu Glu Lys Glu Ala Glu Gly Leu Gly Glu Thr
            100                 105                 110

Pro Ser Trp Trp Arg Glu Ala Asn Leu Leu His Lys Arg Glu Gly Asp
        115                 120                 125

Lys Val Asn Ala Gln Glu Glu Asn Phe Leu Pro Lys Tyr Gln Arg Val
    130                 135                 140

Lys Asp Leu Cys Gln Arg Ala Glu Tyr Gln Thr Ala Cys Glu Gln Leu
145                 150                 155                 160

Gly Gln Lys Trp Gln Cys Val Glu Asp Ala Ser Gly Thr Leu Lys Leu
                165                 170                 175

His Lys Cys Lys Gly Pro Met Arg Phe Gly Gly Gly Gly Ser Arg
            180                 185                 190

Ala Leu Ser Asn Leu Val Pro Lys Tyr Asp Gly Gln Ser Ser Glu Ala
        195                 200                 205

Cys Ser Cys Asp Ser Gly Gly Gly Asp Tyr Lys Leu Gly Leu Ala
    210                 215                 220

Gly Arg Arg Lys Leu Phe Lys Lys Tyr Lys Thr Ser Tyr Ala Arg
225                 230                 235                 240

Asn Arg Ser Ile Arg Ser Val Ala Ile Glu Val Asp Gly Glu Ile Tyr
                245                 250                 255

His Val Gly Leu Asp Thr Val Pro Gln Pro Arg Asn Leu Ser Lys Pro
            260                 265                 270
```

```
His Trp Pro Gly Ala Pro Glu Asp Gln Asp Lys Asp Gly Gly Ser
            275                 280                 285

Phe Ser Gly Thr Gly Gly Leu Pro Asp Tyr Ser Ala Pro Asn Pro Ile
        290                 295                 300

Lys Val Thr His Arg Cys Tyr Ile Leu Glu Asn Asp Thr Val Gln Cys
305                 310                 315                 320

Asp Leu Asp Leu Tyr Lys Ser Leu Gln Ala Trp Lys Asp His Lys Leu
                325                 330                 335

His Ile Asp His Glu Ile Glu Thr Leu Gln Asn Lys Ile Lys Asn Leu
            340                 345                 350

Arg Glu Val Arg Gly His Leu Lys Lys Arg Pro Glu Glu Cys Asp
        355                 360                 365

Cys His Xaa Ile Ser Tyr His Ser Gln His Lys Gly Arg Leu Lys His
        370                 375                 380

Lys Gly Ser Ser Leu His Pro Phe Arg Lys Gly Leu Gln Glu Lys Asp
385                 390                 395                 400

Lys Val Trp Leu Leu Arg Asp Arg Asn Ala Arg Arg Asn Cys Ala Thr
                405                 410                 415

Ala Gln Thr Ala Ala Glu Gln Arg Tyr Val Gln His Ala Arg Pro His
            420                 425                 430

Val Leu Tyr Pro Arg Gln Pro Pro Leu Ala Asp Gly Ala Thr Leu Asp
        435                 440                 445

Ala Gly Ala Val Leu Arg Leu His Gln Arg Gln Gln His Val Leu
    450                 455                 460

Val Leu Glu Asp His Lys
465                 470

<210> SEQ ID NO 36
<211> LENGTH: 690
<212> TYPE: PRT
<213> ORGANISM: Homo sapiens

<400> SEQUENCE: 36

Glu Lys His Gly Ser Asp Tyr Ser Lys Asp Tyr Leu Thr Asp Leu Ile
1               5                   10                  15

Thr Asn Asp Ser Val Ser Phe Phe Arg Thr Ser Lys Lys Met Tyr Pro
            20                  25                  30

His Arg Pro Val Leu Met Val Ile Ser His Ala Ala Pro His Gly Pro
        35                  40                  45

Glu Asp Ser Ala Pro Gln Tyr Ser Arg Leu Phe Pro Asn Ala Ser Gln
    50                  55                  60

His Ile Thr Pro Ser Tyr Asn Tyr Ala Pro Asn Pro Asp Lys His Trp
65                  70                  75                  80

Ile Met Arg Tyr Thr Gly Pro Met Lys Pro Ile His Met Glu Phe Thr
                85                  90                  95

Asn Met Leu Gln Arg Lys Arg Leu Gln Thr Leu Met Ser Val Asp Asp
            100                 105                 110

Ser Met Glu Thr Ile Tyr Asn Met Leu Val Glu Thr Gly Glu Leu Asp
        115                 120                 125

Asn Thr Tyr Ile Val Tyr Thr Ala Asp His Gly Tyr His Ile Gly Gln
    130                 135                 140

Phe Gly Leu Val Lys Gly Lys Ser Met Pro Tyr Glu Phe Asp Ile Arg
145                 150                 155                 160

Val Pro Phe Tyr Val Arg Gly Pro Asn Val Glu Ala Gly Cys Leu Asn
                165                 170                 175
```

-continued

```
Pro His Ile Val Leu Asn Ile Asp Leu Ala Pro Thr Ile Leu Asp Ile
            180                 185                 190
Ala Gly Leu Asp Ile Pro Ala Asp Met Asp Gly Lys Ser Ile Leu Lys
            195                 200                 205
Leu Leu Asp Thr Glu Arg Pro Val Asn Arg Phe His Leu Lys Lys Lys
            210                 215                 220
Met Arg Val Trp Arg Asp Ser Phe Leu Val Glu Arg Gly Lys Leu Leu
225                 230                 235                 240
His Lys Arg Asp Asn Asp Lys Val Asp Ala Gln Glu Glu Asn Phe Leu
                245                 250                 255
Pro Lys Tyr Gln Arg Val Lys Asp Leu Cys Gln Arg Ala Glu Tyr Gln
            260                 265                 270
Thr Ala Cys Glu Gln Leu Gly Gln Lys Trp Gln Cys Val Glu Asp Ala
            275                 280                 285
Thr Gly Lys Leu Lys Leu His Lys Cys Lys Gly Pro Met Arg Leu Gly
            290                 295                 300
Gly Ser Arg Ala Leu Ser Asn Leu Val Pro Lys Tyr Tyr Gly Gln Gly
305                 310                 315                 320
Ser Glu Ala Cys Thr Cys Asp Ser Gly Asp Tyr Lys Leu Ser Leu Ala
                325                 330                 335
Gly Arg Arg Lys Lys Leu Phe Lys Lys Lys Tyr Lys Ala Ser Tyr Val
            340                 345                 350
Arg Ser Arg Ser Ile Arg Ser Val Ala Ile Glu Val Asp Gly Arg Val
            355                 360                 365
Tyr His Val Gly Leu Gly Asp Ala Ala Gln Pro Arg Asn Leu Thr Lys
            370                 375                 380
Arg His Trp Pro Gly Ala Pro Glu Asp Gln Asp Asp Lys Asp Gly Gly
385                 390                 395                 400
Asp Phe Ser Gly Thr Gly Gly Leu Pro Asp Tyr Ser Ala Ala Asn Pro
                405                 410                 415
Ile Lys Val Thr His Arg Cys Tyr Ile Leu Glu Asn Asp Thr Val Gln
            420                 425                 430
Cys Asp Leu Asp Leu Tyr Lys Ser Leu Gln Ala Trp Lys Asp His Lys
            435                 440                 445
Leu His Ile Asp His Glu Ile Glu Thr Leu Gln Asn Lys Ile Lys Asn
            450                 455                 460
Leu Arg Glu Val Arg Gly His Leu Lys Lys Arg Pro Glu Glu Cys
465                 470                 475                 480
Asp Cys His Lys Ile Ser Tyr His Thr Gln His Lys Gly Arg Leu Lys
                485                 490                 495
His Arg Gly Ser Ser Leu His Pro Phe Arg Lys Gly Leu Gln Glu Lys
            500                 505                 510
Asp Lys Val Trp Leu Leu Arg Glu Gln Lys Arg Lys Lys Leu Arg
            515                 520                 525
Lys Leu Leu Lys Arg Leu Gln Asn Asn Asp Thr Cys Ser Met Pro Gly
            530                 535                 540
Leu Thr Cys Phe Thr His Asp Asn Gln His Trp Gln Thr Ala Pro Phe
545                 550                 555                 560
Trp Thr Leu Gly Pro Phe Cys Ala Cys Thr Ser Ala Asn Asn Thr
                565                 570                 575
Tyr Trp Cys Met Arg Thr Ile Asn Glu Thr His Asn Phe Leu Phe Cys
            580                 585                 590
```

```
Glu Phe Ala Thr Gly Phe Leu Glu Tyr Phe Asp Leu Asn Thr Asp Pro
            595                 600                 605

Tyr Gln Leu Met Asn Ala Val Asn Thr Leu Asp Arg Asp Val Leu Asn
    610                 615                 620

Gln Leu His Val Gln Leu Met Glu Leu Arg Ser Cys Lys Gly Tyr Lys
625                 630                 635                 640

Gln Cys Asn Pro Arg Thr Arg Asn Met Asp Leu Gly Leu Lys Asp Gly
                645                 650                 655

Gly Ser Tyr Glu Gln Tyr Arg Gln Phe Gln Arg Arg Lys Trp Pro Glu
            660                 665                 670

Met Lys Arg Pro Ser Ser Lys Ser Leu Gly Gln Leu Trp Glu Gly Trp
            675                 680                 685

Glu Gly
    690

<210> SEQ ID NO 37
<211> LENGTH: 212
<212> TYPE: PRT
<213> ORGANISM: Mus musculus

<400> SEQUENCE: 37

Met Ile Leu Phe Arg Arg His Arg Thr Phe Leu Leu Ala Phe Thr Leu
1               5                   10                  15

Leu Cys Thr Leu Leu Gly Leu Gly Cys Pro Leu Thr Cys Glu Val Cys
            20                  25                  30

Lys Gly Ser Gly His Thr Cys Ser Gly Lys Met Lys Thr Cys Glu Asp
        35                  40                  45

Gly Lys Asp Ala Cys Val Val Leu Val Ser Glu Ser Ser Thr Lys Gly
    50                  55                  60

Arg Lys Ser Val Asn Thr Phe Lys Ala Cys Met Lys Tyr Lys Asp Cys
65                  70                  75                  80

Tyr Ser Gly Phe Val Ser Thr Thr Met Thr Pro Ser Asp Tyr Met Val
                85                  90                  95

Ser Asn Ala His Cys Cys Gln Ser Asp Gly Cys Asn Ser Gly Ser Val
            100                 105                 110

Pro Pro Pro Leu Asn Asn Arg Thr Glu Asn Gly Leu Met Cys Pro Ser
        115                 120                 125

Cys Ile Ala Pro Phe Gln Glu Thr Cys Pro Gly Thr Gln Ala Ala Arg
    130                 135                 140

Cys Val Gly Arg Glu Thr His Cys Ile Tyr Phe Ala Gly Asn Val Gln
145                 150                 155                 160

Ala Gly Ile Ile His Thr Lys Phe Ala Thr Arg Gly Cys Ala Thr Glu
                165                 170                 175

Ser Ala Cys His Thr Lys Ala Gly Ala Glu Val Pro Ser Ala Phe Tyr
            180                 185                 190

Leu Tyr Phe Leu Arg Arg Ala Asp Cys Leu Pro Ala Pro Tyr Pro Pro
        195                 200                 205

Gly Arg Gly Glu
    210

<210> SEQ ID NO 38
<211> LENGTH: 204
<212> TYPE: PRT
<213> ORGANISM: Homo sapiens

<400> SEQUENCE: 38
```

Met Arg Leu Ser Arg Arg Pro Glu Thr Phe Leu Leu Ala Phe Val Leu
1               5                   10                  15

Leu Cys Thr Leu Leu Gly Leu Gly Cys Pro Leu His Cys Glu Ile Cys
            20                  25                  30

Thr Ala Ala Gly Ser Arg Cys His Gly Gln Met Lys Thr Cys Ser Ser
        35                  40                  45

Asp Lys Asp Thr Cys Val Leu Leu Val Gly Lys Ala Thr Ser Lys Gly
    50                  55                  60

Lys Glu Leu Val His Thr Tyr Lys Gly Cys Ile Arg Ser Gln Asp Cys
65                  70                  75                  80

Tyr Ser Gly Val Ile Ser Thr Thr Met Gly Pro Lys Asp His Met Val
                85                  90                  95

Thr Ser Ser Phe Cys Cys Gln Ser Asp Gly Cys Asn Ser Ala Phe Leu
            100                 105                 110

Ser Val Pro Leu Thr Asn Leu Thr Glu Asn Gly Leu Met Cys Pro Ala
            115                 120                 125

Cys Thr Ala Ser Phe Arg Asp Lys Cys Met Gly Pro Met Thr His Cys
        130                 135                 140

Thr Gly Lys Glu Asn His Cys Val Ser Leu Ser Gly His Val Gln Ala
145                 150                 155                 160

Gly Ile Phe Lys Pro Arg Phe Ala Met Arg Gly Cys Ala Thr Glu Ser
                165                 170                 175

Met Cys Phe Thr Lys Pro Gly Ala Glu Val Pro Thr Gly Thr Asn Val
            180                 185                 190

Leu Phe Leu His His Ile Glu Cys Thr His Ser Pro
        195                 200

<210> SEQ ID NO 39
<211> LENGTH: 331
<212> TYPE: PRT
<213> ORGANISM: Mus musculus

<400> SEQUENCE: 39

Met Phe Gly Leu Arg Arg Asn Ala Val Ile Gly Leu Asn Leu Tyr Cys
1               5                   10                  15

Gly Gly Ala Ser Leu Gly Ala Gly Gly Ser Pro Ala Gly Ala Arg
            20                  25                  30

Leu Val Ala Glu Glu Ala Lys Ala Arg Arg Glu Gly Gly Glu Ala
        35                  40                  45

Ala Leu Leu Pro Gly Ala Arg Val Ala Arg Pro Pro Val Gly
    50                  55                  60

Ala Glu Asp Pro Asp Val Thr Ala Ser Ala Glu Arg Arg Leu His Lys
65                  70                  75                  80

Ser Pro Gly Leu Leu Ala Val Pro Pro Glu Glu Met Ala Ala Ser Ala
                85                  90                  95

Ala Ala Ala Ile Val Ser Pro Glu Glu Leu Asp Gly Cys Glu Pro
            100                 105                 110

Glu Ala Ile Gly Lys Arg Pro Ala Val Leu Pro Leu Leu Glu Arg Val
        115                 120                 125

Ser Glu Ala Ala Lys Ser Ser Gly Ala Asp Gly Ser Leu Pro Ser Thr
    130                 135                 140

Pro Pro Pro Pro Glu Glu Glu Asp Asp Leu Tyr Arg Gln Ser Leu
145                 150                 155                 160

Glu Ile Ile Ser Arg Tyr Leu Arg Glu Gln Ala Thr Gly Ser Lys Asp

-continued

```
                165                 170                 175
Ser Lys Pro Leu Gly Glu Ala Gly Ala Gly Arg Arg Ala Leu Glu
            180                 185                 190

Thr Leu Arg Arg Val Gly Asp Gly Val Gln Arg Asn His Glu Thr Ala
        195                 200                 205

Phe Gln Gly Met Leu Arg Lys Leu Asp Ile Lys Asn Glu Gly Asp Val
        210                 215                 220

Lys Ser Phe Ser Arg Val Met Val His Val Phe Lys Asp Gly Val Thr
225                 230                 235                 240

Asn Trp Gly Arg Ile Val Thr Leu Ile Ser Phe Gly Ala Phe Val Ala
                245                 250                 255

Lys His Leu Lys Ser Val Asn Gln Glu Ser Phe Ile Glu Pro Leu Ala
                260                 265                 270

Glu Thr Ile Thr Asp Val Leu Val Arg Thr Lys Arg Asp Trp Leu Val
                275                 280                 285

Lys Gln Arg Gly Trp Asp Gly Phe Val Glu Phe Phe His Val Gln Asp
290                 295                 300

Leu Glu Gly Gly Ile Arg Asn Val Leu Leu Ala Phe Ala Gly Val Ala
305                 310                 315                 320

Gly Val Gly Ala Gly Leu Ala Tyr Leu Ile Arg
                325                 330

<210> SEQ ID NO 40
<211> LENGTH: 350
<212> TYPE: PRT
<213> ORGANISM: Homo sapiens

<400> SEQUENCE: 40

Met Phe Gly Leu Lys Arg Asn Ala Val Ile Gly Leu Asn Leu Tyr Cys
 1               5                  10                  15

Gly Gly Ala Gly Leu Gly Ala Gly Ser Gly Gly Ala Thr Arg Pro Gly
                20                  25                  30

Gly Arg Leu Leu Ala Thr Glu Lys Glu Ala Ser Ala Arg Arg Glu Ile
            35                  40                  45

Gly Gly Gly Glu Ala Gly Ala Val Ile Gly Gly Ser Ala Gly Ala Ser
        50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
                100                 105                 110

Ala Pro Ala Ala Asp Ala Ile Met Ser Pro Glu Glu Glu Leu Asp Gly
            115                 120                 125

Tyr Glu Pro Glu Pro Leu Gly Lys Arg Pro Ala Val Leu Pro Leu Leu
        130                 135                 140

Glu Leu Val Gly Glu Ser Gly Asn Asn Thr Ser Thr Asp Gly Ser Leu
145                 150                 155                 160

Pro Ser Thr Pro Pro Pro Ala Glu Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205
```

```
Ala Leu Glu Thr Leu Arg Arg Val Gly Asp Gly Val Gln Arg Asn His
        210                 215                 220

Glu Thr Val Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
                260                 265                 270

Phe Val Ala Lys His Leu Lys Thr Ile Asn Gln Glu Ser Cys Ile Glu
            275                 280                 285

Pro Leu Ala Glu Ser Ile Thr Asp Val Leu Val Arg Thr Lys Arg Asp
        290                 295                 300

Trp Leu Val Lys Gln Arg Gly Trp Asp Gly Phe Val Glu Phe Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
                340                 345                 350

<210> SEQ ID NO 41
<211> LENGTH: 143
<212> TYPE: PRT
<213> ORGANISM: Mus musculus

<400> SEQUENCE: 41

Met Lys Ser Gln Trp Cys Arg Pro Val Ala Met Asp Leu Gly Val Tyr
1               5                   10                  15

Gln Leu Arg His Phe Ser Ile Ser Phe Leu Ser Ser Leu Leu Gly Thr
            20                  25                  30

Glu Asn Ala Ser Val Arg Leu Asp Asn Ser Ser Gly Ala Ser Val Val
        35                  40                  45

Ala Ile Asp Asn Lys Ile Glu Gln Ala Met Asp Leu Val Lys Ser His
    50                  55                  60

Leu Met Tyr Ala Val Arg Glu Glu Val Glu Val Leu Lys Glu Gln Ile
65                  70                  75                  80

Lys Glu Leu Ile Glu Lys Asn Ser Gln Leu Glu Gln Glu Asn Asn Leu
                85                  90                  95

Leu Lys Thr Leu Ala Ser Pro Glu Gln Leu Ala Gln Phe Gln Ala Gln
            100                 105                 110

Leu Gln Thr Gly Ser Pro Pro Ala Thr Thr Gln Pro Gln Gly Thr Thr
        115                 120                 125

Gln Pro Pro Ala Gln Pro Ala Ser Gln Gly Ser Gly Ser Thr Ala
    130                 135                 140

<210> SEQ ID NO 42
<211> LENGTH: 144
<212> TYPE: PRT
<213> ORGANISM: Homo sapiens

<400> SEQUENCE: 42

Met Lys Ser Gln Trp Cys Arg Pro Val Ala Met Asp Leu Gly Val Tyr
1               5                   10                  15

Gln Leu Arg His Phe Ser Ile Ser Phe Leu Ser Ser Leu Leu Gly Thr
            20                  25                  30

Glu Asn Ala Ser Val Arg Leu Asp Asn Ser Ser Ser Gly Ala Ser Val
        35                  40                  45
```

```
Val Ala Ile Asp Asn Lys Ile Glu Gln Ala Met Asp Leu Val Lys Ser
    50                  55                  60

His Leu Met Tyr Ala Val Arg Glu Val Glu Val Leu Lys Glu Gln
 65                  70                  75                  80

Ile Lys Glu Leu Ile Glu Lys Asn Ser Gln Leu Glu Gln Asn Asn
                    85                  90                  95

Leu Leu Lys Thr Leu Ala Ser Pro Glu Gln Leu Ala Gln Phe Gln Ala
                100                 105                 110

Gln Leu Gln Thr Gly Ser Pro Pro Ala Thr Thr Gln Pro Gln Gly Thr
            115                 120                 125

Thr Gln Pro Pro Ala Gln Pro Ala Ser Gln Gly Ser Gly Pro Thr Ala
    130                 135                 140

<210> SEQ ID NO 43
<211> LENGTH: 291
<212> TYPE: PRT
<213> ORGANISM: Mus musculus

<400> SEQUENCE: 43

Met Val Arg Glu Gln Tyr Thr Thr Val Thr Glu Gly Thr His Ile Glu
  1               5                  10                  15

Arg Pro Glu Asn Gln His Ile Tyr Lys Ile Gly Ile Tyr Gly Trp Arg
                 20                  25                  30

Lys Arg Cys Leu Tyr Leu Phe Val Leu Leu Leu Ala Ile Leu Val
                 35                  40                  45

Val Asn Leu Ala Leu Thr Ile Trp Ile Leu Lys Val Met Trp Phe Ser
    50                  55                  60

Pro Ile Gly Met Gly His Leu His Val Thr Ala Asp Gly Leu Arg Leu
 65                  70                  75                  80

Glu Gly Glu Ser Glu Phe Leu Phe Pro Leu Tyr Ala Lys Glu Ile Arg
                 85                  90                  95

Ser Arg Val Asp Ser Ser Leu Leu Gln Ser Thr Gln Asn Val Thr
                100                 105                 110

Val Ser Ala Arg Asn Ser Glu Gly Glu Val Thr Gly Arg Val Lys Val
            115                 120                 125

Gly Ala Gln Met Val Glu Val Gln Ser Gln His Phe Gln Ile Asn Ser
    130                 135                 140

Glu Asp Gly Lys Pro Leu Phe Ser Ala Glu Glu Gln Asp Val Val Val
145                 150                 155                 160

Gly Thr Gly Arg Leu Arg Val Thr Gly Pro Glu Gly Ala Leu Phe Glu
                165                 170                 175

His Ser Val Glu Thr Pro Leu Val Arg Ala Asp Pro Phe Gln Asp Leu
                180                 185                 190

Arg Leu Glu Ser Pro Thr Arg Ser Leu Ser Met Asp Ala Pro Arg Gly
                195                 200                 205

Val His Val Lys Ala Asn Ala Gly Lys Leu Glu Ala Leu Ser Gln Met
    210                 215                 220

Asp Ile Ile Leu Gln Ser Ser Glu Gly Val Leu Val Leu Asp Ala Glu
225                 230                 235                 240

Thr Val Gly Leu Thr Lys Leu Lys Gln Gly Thr Gln Gly Pro Ala Gly
                245                 250                 255

Ser Ser Asn Gly Phe Tyr Glu Ile Cys Ala Cys Pro Asp Gly Lys Leu
                260                 265                 270

Tyr Leu Ser Met Ala Gly Glu Val Thr Thr Cys Glu Glu His Ser His
                275                 280                 285
```

Val Cys Leu
    290

<210> SEQ ID NO 44
<211> LENGTH: 291
<212> TYPE: PRT
<213> ORGANISM: Homo sapiens

<400> SEQUENCE: 44

Met Val Arg Glu Gln Tyr Thr Thr Ala Thr Glu Gly Ile Cys Ile Glu
1               5                   10                  15

Arg Pro Glu Asn Gln Tyr Val Tyr Lys Ile Gly Ile Tyr Gly Trp Arg
            20                  25                  30

Lys Arg Cys Leu Tyr Leu Phe Val Leu Leu Leu Ile Ile Leu Val
        35                  40                  45

Val Asn Leu Ala Leu Thr Ile Trp Ile Leu Lys Val Met Trp Phe Ser
    50                  55                  60

Pro Ala Gly Met Gly His Leu Cys Val Thr Lys Asp Gly Leu Arg Leu
65              70                  75                  80

Glu Gly Glu Ser Glu Phe Leu Phe Pro Leu Tyr Ala Lys Glu Ile His
                85                  90                  95

Ser Arg Val Asp Ser Ser Leu Leu Leu Gln Ser Thr Gln Asn Val Thr
            100                 105                 110

Val Asn Ala Arg Asn Ser Glu Gly Glu Val Thr Gly Arg Leu Lys Val
        115                 120                 125

Gly Pro Lys Met Val Glu Val Gln Asn Gln Gln Phe Gln Ile Asn Ser
    130                 135                 140

Asn Asp Gly Lys Pro Leu Phe Thr Val Asp Glu Lys Glu Val Val Val
145                 150                 155                 160

Gly Thr Asp Lys Leu Arg Val Thr Gly Pro Glu Gly Ala Leu Phe Glu
                165                 170                 175

His Ser Val Glu Thr Pro Leu Val Arg Ala Asp Pro Phe Gln Asp Leu
            180                 185                 190

Arg Leu Glu Ser Pro Thr Arg Ser Leu Ser Met Asp Ala Pro Arg Gly
        195                 200                 205

Val His Ile Gln Ala His Ala Gly Lys Ile Glu Ala Leu Ser Gln Met
    210                 215                 220

Asp Ile Leu Phe His Ser Ser Asp Gly Met Leu Val Leu Asp Ala Glu
225                 230                 235                 240

Thr Val Cys Leu Pro Lys Leu Val Gln Gly Thr Trp Gly Pro Ser Gly
                245                 250                 255

Ser Ser Gln Ser Leu Tyr Glu Ile Cys Val Cys Pro Asp Gly Lys Leu
            260                 265                 270

Tyr Leu Ser Val Ala Gly Val Ser Thr Thr Cys Gln Glu His Ser His
        275                 280                 285

Ile Cys Leu
    290

<210> SEQ ID NO 45
<211> LENGTH: 228
<212> TYPE: PRT
<213> ORGANISM: Homo sapiens

<400> SEQUENCE: 45

Met Trp Val Gln Thr Arg Pro Ser Ser Ala Ser Tyr Lys Ser Trp Gly
1               5                   10                  15

-continued

```
Pro Gly Thr Ala Asp Thr His Thr Met Arg Leu Ser Arg Arg Pro Glu
             20                  25                  30

Thr Phe Leu Leu Ala Phe Val Leu Leu Cys Thr Leu Leu Gly Leu Gly
             35                  40                  45

Cys Pro Leu His Cys Glu Ile Cys Thr Ala Ala Gly Ser Arg Cys His
             50                  55                  60

Gly Gln Met Lys Thr Cys Ser Ser Asp Lys Asp Thr Cys Val Leu Leu
 65                  70                  75                  80

Val Gly Lys Ala Thr Ser Lys Gly Lys Glu Leu Val His Thr Tyr Lys
                 85                  90                  95

Gly Cys Ile Arg Ser Gln Asp Cys Tyr Ser Gly Val Ile Ser Thr Thr
                100                 105                 110

Met Gly Pro Lys Asp His Met Val Thr Ser Ser Phe Cys Cys Gln Ser
                115                 120                 125

Asp Gly Cys Asn Ser Ala Phe Leu Ser Val Pro Leu Thr Asn Leu Thr
                130                 135                 140

Glu Asn Gly Leu Met Cys Pro Ala Cys Thr Ala Ser Phe Arg Asp Lys
145                 150                 155                 160

Cys Met Gly Pro Met Thr His Cys Thr Gly Lys Glu Asn His Cys Val
                165                 170                 175

Ser Leu Ser Gly His Val Gln Ala Gly Ile Phe Lys Pro Arg Phe Ala
                180                 185                 190

Met Arg Gly Cys Ala Thr Glu Ser Met Cys Phe Thr Lys Pro Gly Ala
                195                 200                 205

Glu Val Pro Thr Gly Thr Asn Val Leu Phe Leu His His Ile Glu Cys
                210                 215                 220

Thr His Ser Pro
225

<210> SEQ ID NO 46
<211> LENGTH: 140
<212> TYPE: PRT
<213> ORGANISM: Mus musculus

<400> SEQUENCE: 46

Met Ala Ser Pro Leu Arg Ser Leu Leu Phe Leu Leu Ala Val Leu Ala
 1               5                  10                  15

Val Ala Trp Ala Ala Thr Pro Lys Gln Gly Pro Arg Met Leu Gly Ala
             20                  25                  30

Pro Glu Glu Ala Asp Ala Asn Glu Glu Gly Val Arg Arg Ala Leu Asp
             35                  40                  45

Phe Ala Val Ser Glu Tyr Asn Lys Gly Ser Asn Asp Ala Tyr His Ser
             50                  55                  60

Arg Ala Ile Gln Val Val Arg Ala Arg Lys Gln Leu Val Ala Gly Val
 65                  70                  75                  80

Asn Tyr Phe Leu Asp Val Glu Met Gly Arg Thr Thr Cys Thr Lys Ser
                 85                  90                  95

Gln Thr Asn Leu Thr Asp Cys Pro Phe His Asp Gln Pro His Leu Met
                100                 105                 110

Arg Lys Ala Leu Cys Ser Phe Gln Ile Tyr Ser Val Pro Trp Lys Gly
                115                 120                 125

Thr His Ser Leu Thr Lys Phe Ser Cys Lys Asn Ala
                130                 135                 140
```

```
<210> SEQ ID NO 47
<211> LENGTH: 146
<212> TYPE: PRT
<213> ORGANISM: Homo sapiens

<400> SEQUENCE: 47

Met Ala Gly Pro Leu Arg Ala Pro Leu Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
        35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
    130                 135                 140

Asp Ala
145

<210> SEQ ID NO 48
<211> LENGTH: 140
<212> TYPE: PRT
<213> ORGANISM: Mus musculus

<400> SEQUENCE: 48

Met Ala Ser Pro Leu Arg Ser Leu Leu Phe Leu Leu Ala Val Leu Ala
1               5                   10                  15

Val Ala Trp Ala Ala Thr Pro Lys Gln Gly Pro Arg Met Leu Gly Ala
            20                  25                  30

Pro Glu Glu Ala Asp Ala Asn Lys Glu Gly Val Arg Arg Ala Leu Asp
        35                  40                  45

Phe Ala Val Ser Glu Tyr Asn Lys Gly Ser Asn Asp Ala Tyr His Ser
    50                  55                  60

Arg Ala Ile Gln Val Val Arg Ala Arg Lys Gln Leu Val Ala Gly Val
65                  70                  75                  80

Asn Tyr Phe Leu Asp Val Glu Met Gly Arg Thr Thr Cys Thr Lys Ser
                85                  90                  95

Gln Thr Asn Leu Thr Asp Cys Pro Phe His Asp Gln Pro His Leu Met
            100                 105                 110

Arg Lys Ala Leu Cys Ser Phe Gln Ile Tyr Ser Val Pro Trp Lys Gly
        115                 120                 125

Thr His Ser Leu Thr Lys Phe Ser Cys Lys Asn Ala
    130                 135                 140

<210> SEQ ID NO 49
<211> LENGTH:
```

<212> TYPE:
<213> ORGANISM:

<400> SEQUENCE: 49

000

<210> SEQ ID NO 50
<211> LENGTH: 2231
<212> TYPE: DNA
<213> ORGANISM: Mus musculus

<400> SEQUENCE: 50

| | | | | | |
|---|---|---|---|---|---|
| cggcgaggaa | gatggcggac | gggaaggcgg | gagaggagaa | gccagagaag | ccgcagcgag | 60 |
| ccggagccgc | cggaggacct | gaagaagaag | cagaaaaacc | tgtgaaaact | aagactgttt | 120 |
| cttccagtaa | tggaggggaa | agttccagtc | gcagcgctga | aaagcgatca | gctgaagacg | 180 |
| aagctgcaga | cctcccaaca | aagcctacaa | agatgtccaa | gtttggattt | gccataggta | 240 |
| gtcagacggc | acggaaagcg | tccgccatct | ccattagact | cggagcaagt | aagcctaagg | 300 |
| aaacagttcc | aactcttgct | ccaaaaactc | tgtcggtagc | agcagctttc | aatgaagatg | 360 |
| aagatagtga | gccagaagaa | atgcctccag | aagcaaagat | gaggatgaag | aacattggaa | 420 |
| gggacacacc | aacatcagcg | ggaccaaact | cctttaataa | agggaagcat | ggcttttccg | 480 |
| ataaccagaa | gctgtgggag | cgaaatataa | aatctcatct | tggaaacgtc | cacgaccaag | 540 |
| acaattaagt | gaagtgtctg | agactggggt | gtgggtgggt | gcagttagaa | ggagcagtct | 600 |
| ccttttttgta | aagaatggtg | taagactagc | tttggagccg | ttttttctttc | ttctttttttt | 660 |
| cttttccttt | tttctttttt | tttttttttt | ttaagattga | gtggtacact | aataaatgag | 720 |
| agtttgcaat | tagaggtaat | ttatgttttta | tatacagatt | tcaagacatt | tgctaattttt | 780 |
| gtagtttcac | atgattagtt | tccaagggtt | acagataata | aagaaatcac | aagtggtacc | 840 |
| tttctaagaa | ttgcatattt | ttttagacac | aactattagc | acattaagag | ggaagccaaa | 900 |
| agttattgtc | tgcttcaaac | tggaagcagt | tcctctcctg | acttctccct | cgttacccga | 960 |
| ctgtccggct | ccctgcagca | gccttaccga | gagggagatt | ggcttgagaa | gccagtgtta | 1020 |
| ctgttgtgac | tgttggctga | gaggaagttt | agatgaggtt | caagtaaacc | ctttcctgcg | 1080 |
| ggcatttcgt | tttgtttcgg | gccattctag | ctagtactgc | ttcgctctca | gtgggtaccg | 1140 |
| atgcttgctc | tgtaaaaata | aattttttttc | gttaaaaatt | cttatatgaa | gaattgagta | 1200 |
| ttatgactag | cccactctaa | cggagtgtgt | ctccgttgag | gaccttcaga | ggacactatt | 1260 |
| tgctaccaaa | gtgaaccagt | attctgaatg | tgcttctctt | ggtttctgtt | ctagttccta | 1320 |
| gaagcatttc | caccagaact | tgaggcaaaa | cataaggaag | ctgtttcttt | taaagtacaa | 1380 |
| acaccaccaa | aaatatcagt | gtacatagtg | ctttatgtat | ttggctggct | ttatttttt | 1440 |
| aaaaggttta | ataacaaaa | aaggaaaaaa | aggtatagca | ttgtatgaag | gcagatgagg | 1500 |
| cgacacacct | gtgacatttg | aagcatttgt | gttactaact | tactagatcc | ggtttgaatt | 1560 |
| gaattccacaa | ggtttcttac | ttgtccaact | ccaggcttat | tttacgtaca | tacaacctga | 1620 |
| ccagtggttt | caaaagcaca | tttagtgact | gcaataggac | agaaatgctt | ctctagacac | 1680 |
| atcttcattg | cgagcgtctc | atcgcatatg | ctccttagagt | tctgaatgta | ggatgtttgt | 1740 |
| tttgtattttt | tgtattgtat | atgggctttt | taaatgtgac | agttaaatgc | atctttaata | 1800 |
| gtcacagaca | aaagagatga | taaaatgtcc | tttgaaaatg | gcaatgttga | gtttggaggc | 1860 |
| agcttcgggg | agtttcctgg | gtggcgatga | ttcactgggc | agttttttaat | gtagtgactt | 1920 |

| | |
|---|---|
| caagaagcag cctgcggata ttcctaacac ttggttcact acagtttagt ttacttcata | 1980 |
| agccccaagt aaaacgatgg aaatgtacat agcactatta gttcatacat gatttaagta | 2040 |
| tatcaagata cataaattta acattatgt ctgcaaactg tccatttgtc cattttactg | 2100 |
| tttgttgaaa taacacctct cctacatatt ctttacttga ctcgaataac aaattaacct | 2160 |
| gacgtcaaga tggagagaga cgactgagct gaatgtcttt actaaaatta caataaattt | 2220 |
| tgtcaaactc g | 2231 |

<210> SEQ ID NO 51
<211> LENGTH: 1066
<212> TYPE: DNA
<213> ORGANISM: Homo sapiens

<400> SEQUENCE: 51

| | |
|---|---|
| ggggaggccg cggcgggaa aatggcggac gggaaggcgg gagacgagaa gcctgaaaag | 60 |
| tcgcagcgag ctggagccgc cggaggacct gaagaagaag cagaaaaacc tgtgaaaact | 120 |
| aagactgttt cttccagtaa tggaggggaa agttccagtc gcagcgctga aagcgatca | 180 |
| gctgaagaag aagctgccga cctcccaaca aagcctacaa agatctccaa gtttggattt | 240 |
| gccataggta gtcagacgac aaagaaagca tcagccatat ccatcaaact tggatcaagt | 300 |
| aagcctaaag aaactgttcc aactcttgct ccaaaaactc tttcagtagc agcagctttt | 360 |
| aatgaagatg aagatagtga accagaggaa atgcctccag aagcaaagat gaggatgaag | 420 |
| aatattggaa gggatacacc aacatcagct ggaccaaact ccttcaataa aggaaagcat | 480 |
| gggttttctg ataaccagaa gctgtgggag cgaaatataa aatctcatct tggaaatgtc | 540 |
| catgaccaag acaattaaat gatgttttga aattggggtg tggggtgggt gtaaagttaa | 600 |
| aaggaacagt ttccttttt aaagaatggt ataagactat ctttggagcc gctttttttt | 660 |
| tcttttcat tttttaaa gattgagtgg tacactaata aatgagagtt tgaaattaga | 720 |
| ggtaattat gttttatata cagatttcaa gacatttgct aattttgtag tttcatgtga | 780 |
| ttagtttcca aaggttacag ataataaaga aatcagaaat ggtaccmatt ttaaraattg | 840 |
| cycattttt ttttagagcc camctattag ccccmttaag akggdgyaaa rchaawgtat | 900 |
| aaramtrcaa gmatgwtarc ctstctkars tcccttatta cctaaacttg tctggctccc | 960 |
| aggaacagcc ttatagagag agggagtatt gtattgggaa gaaatgttta ctgaactatt | 1020 |
| gactgaaagt aaatttagat aaaatacaaa aaaaaaaaa aaaaaa | 1066 |

<210> SEQ ID NO 52
<211> LENGTH: 773
<212> TYPE: DNA
<213> ORGANISM: Mus musculus

<400> SEQUENCE: 52

| | |
|---|---|
| attcggatcc ttgtagaaat tgctggacgc ttctgtacgt ttcgcagttt gtcttcgctg | 60 |
| atcggtgaga cttcgagcag ttaggatgcc gcgtggaagc cgaagccgca cttcccgggt | 120 |
| gactcctccg gccagccggg cccctcagat gagggctgct ccccgaagag cacctgcagc | 180 |
| tcagcctcca gcagcagctg cgccatctgc agttggctca cctgccgctg cgccccggca | 240 |
| gccaggcctg atgcccaga tggctaccac cgcggccggt gtggctgtgg gctctgcagt | 300 |
| gggacacacc ctgggtcacg ccatcactgg gggcttcagc ggaggtggca gtgctgagcc | 360 |
| cgcaaagccc gacatcactt accaggagcc tcagggagcc cagctgcaga ccagcagtc | 420 |
| ttttggacct tgctctctag agatcaagca gtttctggag tgtgctcaga accagagcga | 480 |
| tgtcaagctc tgtgagggct tcaacgaggt gctgcggcag tgcaggattg caaatggttt | 540 |

| | |
|---|---:|
| aatgtaatca agaaattcaa gctgaagaga tgtaacattg gttctgtata attgatagta | 600 |
| caagtgtgga cccttatatt tctaacagtt cattgctttg gaatggccgt gaaagagatc | 660 |
| taactgtgga tgcttactga ggcttgtatg tagtgttggt tactggggaa gtgtttggcc | 720 |
| tccttggact gtgttgtgat tgtgagttaa aaaaaataaa ttggttattc tga | 773 |

<210> SEQ ID NO 53
<211> LENGTH: 3057
<212> TYPE: DNA
<213> ORGANISM: Mus musculus

<400> SEQUENCE: 53

| | |
|---|---:|
| aatgctggtg gagacggggg agctggacaa cacgtacatc ctgtacaccg ccgaccacgg | 60 |
| ctaccacatt ggccagtttg gctggtgaa gggcaagtct atgccgtatg aattcgacat | 120 |
| cagagtcccg ttctacgtga ggggccccaa cgtggaagct ggctctctga ccccccacat | 180 |
| tgtcctcaac attgacctgg gcccccacca tactggatat cgctggactg acatccctg | 240 |
| cagacatgga cgggaagtct attctcaaac tactggactc agagcggcca gtgaaccggt | 300 |
| tccacttgaa aagaagctg agggtcttgg cgagactcct tcctggtgga gagaggcaaa | 360 |
| cttgctccac aagagggagg gtgacaaagt gaatgcccag gaggagaact tcctgcccaa | 420 |
| gtaccagcgc gtgaaggacc tgtgtcagcg agctgagtac cagacagcat gcgaacagct | 480 |
| ggggcagaag tggcagtgtg tggaggacgc ttctgggacg ctgaagctgc acaaatgtaa | 540 |
| aggccccatg cggtttggtg gcggcggtgg cagcagagcc ctctccaacc tggtgcccaa | 600 |
| gtatgacggc cagagcagcg aggcctgcag ctgtgacagt ggcggtggag gggactacaa | 660 |
| actgggcctg gctggacgcc gtaagctctt taagaaaaag tataagacca gctatgcccg | 720 |
| gaaccgctcc atccgttccg tggccatcga ggtggacggt gagatatacc acgtaggctt | 780 |
| ggatactgtg cctcagcccc gcaaccttag caagccgcac tggccagggg ccctgaaga | 840 |
| ccaagatgac aaggatggtg gcagtttcag tggtactggt ggccttccag attattctgc | 900 |
| ccccaatccc atcaaagtga cccatcggtg ctacatcctt gagaatgaca cagtccagtg | 960 |
| cgacttggac ctgtacaagt ccctgcaggc ttggaaagac cacaagctgc acatcgacca | 1020 |
| tgagatcgaa accctgcaga acaaaattaa gaaccttcga gaagtcaggg gtcacctgaa | 1080 |
| gaagaagcga ccggaagaat gtgactgcca taraatcagt taccacagcc aacacaaagg | 1140 |
| ccgtctcaag cacaaaggct ccagcctgca cccttttcagg aagggtctgc aggagaagga | 1200 |
| caaggtgtgg ctgctgcggg acagaaacgc aagaagaaac tgcgcaactg ctcaaacggc | 1260 |
| tgcagaacaa cgatacgtgc agcatgcccg gcctcacgtg cttaccac gacaaccacc | 1320 |
| actggcagac ggcgccactc tggacgctgg ggccgttctg cgcctgcacc agcgccaaca | 1380 |
| acaacacgta ctggtgcttg aggaccataa atgagcccaa caacttcctc ttctgcgaat | 1440 |
| tgcaaccgg cttcatagaa actttgacc tcagtacaga cccctaccag ctgatgaacg | 1500 |
| cggtgaacac actggacagg gacgtcctta accaactgca cgtgcagctc atggagctaa | 1560 |
| ggagctgtaa aggctacaag cagtgcaacc cccggacccg caacatggac ctggggctta | 1620 |
| gagacggagg aagctatgaa caatacaggc agtttcagcg tcgaaaatgg ccagaaatga | 1680 |
| agagaccttc ttccaaatca ctgggacagc tatgggaagg ttgggaaggc taagcggcca | 1740 |
| tagagagagg aacctccaaa accaggggc tcgtgtggct gcccaggcca tgcaaaaaac | 1800 |
| acccgattcc cagaagatga atgttggaac tgggagacct gacagaaggc agggctgctc | 1860 |
| ttgggacagg aaatcctgga ggacagcgcc tggactttcc gatgctcagt ttctttgccc | 1920 |

```
tgctttgctc tggatcaaac ctcactggct gctctgggat gcgtgctcac acctggagtc   1980
tctgctcacc ctttcagagg ctcacaaaga caaaggaact aatttccatg gacacttcct   2040
ccagagatgg aaattgctgg gattcgccca ctcctcccct gcaccccctcc cccagtcatc   2100 tagggaagca agcttgtttt aaccttctta ctctttggag aaagcacgga catcccaggt   2160
gctgtcaacc tcacagtctt gacaaagtct atagcacaaa acagtaccat tcaccaggct   2220
ggttgacctg gctggctcag aagctgcctt caccacatac atgaccgctc acacgtaacc   2280
aacacaggga attgtagggg aatctcacta atatgaaatc ccgcttttca agagtcgcgg   2340
tgtcaataaa cgctgtggct aggatcaagg ataatcccctt gagctttcag acatttattc   2400
ctgcccggga ttcgttcctt tgttatccat cccagaacta atgttttttct aaggtaccga   2460 aaccccaagt tgatgtgtgt cctgtgtttt aatgacattg tatttgtaaa gttttgtagt   2520
ataagtacca tcttacagtg ttcctgcccc cagccaatgt ctagctattg gtatgaaaaa   2580
aaaaatcttt gaatttttgt aaaaggcwaw mwwrrramww wwwwgctctt tattattatc   2640
atttttttct tgaagcactc aagatgttgt cgaccttcag ctgagggttg gagaagcaga   2700
gggtaataca ttaatagtaa acctctccga ttcaagggac ctcataggta agtctcacca   2760
gctttggggc atcgatctgt gaagcaaagc atccaactgc accaaccctt tgttcatcca   2820
ggtagggtaa cctggtcaat atggctgcca gaaagcagct gtcagagctt cggaggtggg   2880
ggtggaaatg tcagcccaac ccgactcagc agaggggggc cacatttctc taaaccagca   2940 gttttttcagc tggggctcca acgacctttc acaggggtcc taaggtcatc agagagcaca   3000
tttaatggta cagttcacac agtaacaatc acagctaaga agtagcacag tagcagc     3057
```

<210> SEQ ID NO 54
<211> LENGTH: 732
<212> TYPE: DNA
<213> ORGANISM: Mus musculus

<400> SEQUENCE: 54

```
ggactacagg ttcacacacc atgattctgt ttagaagaca caggaccttc ctgctggcct     60
tcacactgct ctgtaccctc ctgggtctcg ggtgccctct aacttgtgag gtgtgcaaag    120
gctcggggca cacatgcagc gggaagatga agacctgtga agacggcaaa gacgcatgcg    180
tggtcctagt gagcgagtcc agcacaaagg gccgaaagtc agtgaacacc ttcaaggcct    240
gcatgaagta caaagactgc tactcaggct tcgtatcaac caccatgact cccagtgact    300
acatggtgtc caacgcccac tgctgtcaaa gtgacggttg caacagtggc tctgtgcccc    360
ctcccttgaa caatcggaca gagaatggcc tgatgtgtcc ctcctgcatt gcgccccttcc    420 aggagacctg tccaggaacc caggcagctc gctgcgtggg ccgggaaaca cactgcatct    480 atttttgctgg caatgtgcag gctggtatta tccacacgaa atttgccacg agggggctgtg    540 ctacagagag cgcctgccac accaaggcag gggctgaggt cccttcagcc ttctatctct    600
acttcctgcg ccgggcagac tgccttccag cccccttaccc tcctggcagg ggagagtgaa    660
gaaaccgaga agtatgtaac ttgaggagcc ctgcagcttt ccagctgcct gtaaattaaa    720
cagatygaca gt                                                        732
```

<210> SEQ ID NO 55
<211> LENGTH: 178
<212> TYPE: PRT
<213> ORGANISM: Mus musculus

<400> SEQUENCE: 55

```
Met Ala Asp Gly Lys Ala Gly Glu Glu Lys Pro Glu Lys Pro Gln Arg
 1               5                  10                  15

Ala Gly Ala Ala Gly Gly Pro Glu Glu Ala Glu Lys Pro Val Lys
            20                  25                  30

Thr Lys Thr Val Ser Ser Ser Asn Gly Gly Glu Ser Ser Ser Arg Ser
            35                  40                  45

Ala Glu Lys Arg Ser Ala Glu Asp Glu Ala Ala Asp Leu Pro Thr Lys
 50                  55                  60

Pro Thr Lys Met Ser Lys Phe Gly Phe Ala Ile Gly Ser Gln Thr Ala
 65                  70                  75                  80

Arg Lys Ala Ser Ala Ile Ser Ile Arg Leu Gly Ala Ser Lys Pro Lys
                85                  90                  95

Glu Thr Val Pro Thr Leu Ala Pro Lys Thr Leu Ser Val Ala Ala Ala
                100                 105                 110

Phe Asn Glu Asp Glu Asp Ser Glu Pro Glu Met Pro Pro Glu Ala
            115                 120                 125

Lys Met Arg Met Lys Asn Ile Gly Arg Asp Thr Pro Thr Ser Ala Gly
            130                 135                 140

Pro Asn Ser Phe Asn Lys Gly Lys His Gly Phe Ser Asp Asn Gln Lys
145                 150                 155                 160

Leu Trp Glu Arg Asn Ile Lys Ser His Leu Gly Asn Val His Asp Gln
                165                 170                 175

Asp Asn

<210> SEQ ID NO 56
<211> LENGTH: 178
<212> TYPE: PRT
<213> ORGANISM: Homo sapiens

<400> SEQUENCE: 56

Met Ala Asp Gly Lys Ala Gly Asp Glu Lys Pro Glu Lys Ser Gln Arg
 1               5                  10                  15

Ala Gly Ala Ala Gly Gly Pro Glu Glu Ala Glu Lys Pro Val Lys
            20                  25                  30

Thr Lys Thr Val Ser Ser Ser Asn Gly Gly Glu Ser Ser Ser Arg Ser
            35                  40                  45

Ala Glu Lys Arg Ser Ala Glu Glu Glu Ala Ala Asp Leu Pro Thr Lys
 50                  55                  60

Pro Thr Lys Ile Ser Lys Phe Gly Phe Ala Ile Gly Ser Gln Thr Thr
 65                  70                  75                  80

Lys Lys Ala Ser Ala Ile Ser Ile Lys Leu Gly Ser Ser Lys Pro Lys
                85                  90                  95

Glu Thr Val Pro Thr Leu Ala Pro Lys Thr Leu Ser Val Ala Ala Ala
                100                 105                 110

Phe Asn Glu Asp Glu Asp Ser Glu Pro Glu Met Pro Pro Glu Ala
            115                 120                 125

Lys Met Arg Met Lys Asn Ile Gly Arg Asp Thr Pro Thr Ser Ala Gly
            130                 135                 140

Pro Asn Ser Phe Asn Lys Gly Lys His Gly Phe Ser Asp Asn Gln Lys
145                 150                 155                 160

Leu Trp Glu Arg Asn Ile Lys Ser His Leu Gly Asn Val His Asp Gln
                165                 170                 175

Asp Asn
```

-continued

```
<210> SEQ ID NO 57
<211> LENGTH: 153
<212> TYPE: PRT
<213> ORGANISM: Mus musculus

<400> SEQUENCE: 57

Met Pro Arg Gly Ser Arg Ser Arg Thr Ser Arg Val Thr Pro Pro Ala
 1               5                  10                  15

Ser Arg Ala Pro Gln Met Arg Ala Ala Pro Arg Arg Ala Pro Ala Ala
            20                  25                  30

Gln Pro Pro Ala Ala Ala Pro Ser Ala Val Gly Ser Pro Ala Ala
        35                  40                  45

Ala Pro Arg Gln Pro Gly Leu Met Ala Gln Met Ala Thr Thr Ala Ala
    50                  55                  60

Gly Val Ala Val Gly Ser Ala Val Gly His Thr Leu Gly His Ala Ile
65                  70                  75                  80

Thr Gly Gly Phe Ser Gly Gly Gly Ser Ala Glu Pro Ala Lys Pro Asp
                85                  90                  95

Ile Thr Tyr Gln Glu Pro Gln Gly Ala Gln Leu Gln Asn Gln Gln Ser
            100                 105                 110

Phe Gly Pro Cys Ser Leu Glu Ile Lys Gln Phe Leu Glu Cys Ala Gln
        115                 120                 125

Asn Gln Ser Asp Val Lys Leu Cys Glu Gly Phe Asn Glu Val Leu Arg
    130                 135                 140

Gln Cys Arg Ile Ala Asn Gly Leu Met
145                 150

<210> SEQ ID NO 58
<211> LENGTH: 151
<212> TYPE: PRT
<213> ORGANISM: Homo sapiens

<400> SEQUENCE: 58

Met Pro Arg Gly Ser Arg Ser Arg Thr Ser Arg Met Ala Pro Pro Ala
 1               5                  10                  15

Ser Arg Ala Pro Gln Met Arg Ala Ala Pro Arg Pro Ala Pro Val Ala
            20                  25                  30

Gln Pro Pro Ala Ala Ala Pro Pro Ser Ala Val Gly Ser Ser Ala Ala
        35                  40                  45

Ala Pro Arg Gln Pro Gly Leu Met Ala Gln Met Ala Thr Thr Ala Ala
    50                  55                  60

Gly Val Ala Val Gly Ser Ala Val Gly His Thr Leu Gly His Ala Ile
65                  70                  75                  80

Thr Gly Gly Phe Ser Gly Gly Ser Asn Ala Glu Pro Ala Arg Pro Asp
                85                  90                  95

Ile Thr Tyr Gln Glu Pro Gln Gly Thr Gln Pro Ala Gln Gln Gln
            100                 105                 110

Pro Cys Leu Tyr Glu Ile Lys Gln Phe Leu Glu Cys Ala Gln Asn Gln
        115                 120                 125

Gly Asp Ile Lys Leu Cys Glu Gly Phe Asn Glu Val Leu Lys Gln Cys
    130                 135                 140

Arg Leu Ala Asn Gly Leu Ala
145                 150

<210> SEQ ID NO 59
<211> LENGTH: 19
<212> TYPE: DNA
```

```
<213> ORGANISM: Mus musculus

<400> SEQUENCE: 59
cgagcgctac attgtcgct                                                      19

<210> SEQ ID NO 60
<211> LENGTH: 22
<212> TYPE: DNA
<213> ORGANISM: Mus musculus

<400> SEQUENCE: 60
gtcttaaatt tgcttgtgcc cc                                                  22

<210> SEQ ID NO 61
<211> LENGTH: 19
<212> TYPE: DNA
<213> ORGANISM: Mus musculus

<400> SEQUENCE: 61
atcaacggga agcccatca                                                      19

<210> SEQ ID NO 62
<211> LENGTH: 20
<212> TYPE: DNA
<213> ORGANISM: Mus musculus

<400> SEQUENCE: 62
gacatactca gcaccggcct                                                     20

<210> SEQ ID NO 63
<211> LENGTH: 823
<212> TYPE: PRT
<213> ORGANISM: Mus musculus

<400> SEQUENCE: 63
```

Met Gly Phe Gly Ser Asp Leu Lys Asn Ser Gln Glu Ala Val Leu Lys
 1               5                  10                  15

Leu Gln Asp Trp Glu Leu Arg Leu Leu Glu Thr Val Lys Lys Phe Met
            20                  25                  30

Ala Leu Arg Ile Lys Ser Asp Lys Glu Tyr Ala Tyr Thr Leu Gln Asn
        35                  40                  45

Leu Cys Asn Gln Val Asp Lys Glu Ser Thr Val Gln Val Asn Tyr Val
    50                  55                  60

Ser Asn Val Ser Lys Ser Trp Leu Leu Met Ile Gln Gln Thr Glu Gln
65                  70                  75                  80

Leu Ser Arg Ile Met Lys Thr His Ala Glu Asp Leu Asn Ser Gly Pro
                85                  90                  95

Leu His Arg Leu Thr Met Met Ile Lys Asp Lys Gln Gln Val Lys Lys
            100                 105                 110

Ser Tyr Val Gly Ile His Gln Gln Ile Glu Ala Glu Met Ile Lys Val
        115                 120                 125

Thr Lys Thr Glu Leu Glu Lys Leu Lys Ser Ser Tyr Arg Gln Leu Ile
    130                 135                 140

Lys Glu Met Asn Ser Ala Lys Glu Lys Tyr Lys Glu Ala Leu Ala Lys
145                 150                 155                 160

Gly Lys Glu Thr Glu Lys Ala Lys Glu Arg Tyr Asp Lys Ala Thr Met
                165                 170                 175

Lys Leu His Met Leu His Asn Gln Tyr Val Leu Ala Leu Lys Gly Ala
            180                 185                 190

```
Gln Leu His Gln Ser Gln Tyr Tyr Asp Thr Thr Leu Pro Leu Leu Leu
        195                 200                 205
Asp Ser Val Gln Lys Met Gln Glu Glu Met Ile Lys Ala Leu Lys Gly
210                 215                 220
Ile Phe Asp Asp Tyr Ser Gln Ile Thr Ser Leu Val Thr Glu Glu Ile
225                 230                 235                 240
Val Asn Val His Lys Glu Ile Gln Met Ser Val Glu Gln Ile Asp Pro
                245                 250                 255
Ser Thr Glu Tyr Asn Asn Phe Ile Asp Val His Arg Thr Thr Ala Ala
            260                 265                 270
Lys Glu Gln Glu Ile Glu Phe Asp Thr Ser Leu Leu Glu Glu Asn Glu
            275                 280                 285
Asn Leu Gln Ala Asn Glu Ile Met Trp Asn Asn Leu Thr Ala Asp Ser
290                 295                 300
Leu Gln Val Met Leu Lys Thr Leu Ala Glu Glu Leu Thr Gln Thr Gln
305                 310                 315                 320
Gln Met Leu Leu His Lys Glu Ala Ala Val Leu Glu Leu Glu Lys Arg
                325                 330                 335
Ile Glu Glu Ser Phe Glu Thr Cys Glu Lys Lys Ser Asp Ile Val Leu
                340                 345                 350
Leu Leu Gly Gln Lys Gln Ala Leu Glu Glu Leu Lys Gln Ser Val Gln
            355                 360                 365
Gln Leu Arg Cys Ser Glu Ala Lys Cys Ala Ala Gln Lys Ala Leu Leu
            370                 375                 380
Glu Gln Lys Val Gln Glu Asn Asp Gly Lys Glu Pro Pro Pro Val Val
385                 390                 395                 400
Asn Tyr Glu Glu Asp Ala Arg Ser Val Thr Ser Met Glu Arg Lys Glu
                405                 410                 415
Arg Leu Ser Lys Phe Glu Ser Ile Arg His Ser Ile Ala Gly Ile Ile
                420                 425                 430
Lys Ser Pro Lys Ser Val Leu Gly Ser Ser Thr Gln Val Cys Asp Val
            435                 440                 445
Ile Ser Val Gly Glu Arg Pro Leu Ala Glu His Asp Trp Tyr His Gly
450                 455                 460
Ala Ile Pro Arg Ile Glu Ala Gln Glu Leu Leu Lys Gln Gln Gly Asp
465                 470                 475                 480
Phe Leu Val Arg Glu Ser His Gly Lys Pro Gly Glu Tyr Val Leu Ser
                485                 490                 495
Val Tyr Ser Asp Gly Gln Arg Arg His Phe Ile Ile Gln Phe Val Asp
            500                 505                 510
Asn Leu Tyr Arg Phe Glu Gly Thr Gly Phe Ser Asn Ile Pro Gln Leu
            515                 520                 525
Ile Asp His His Phe Asn Thr Lys Gln Val Ile Thr Lys Lys Ser Gly
            530                 535                 540
Val Val Leu Leu Asn Pro Ile Pro Lys Asp Lys Lys Trp Val Leu Asn
545                 550                 555                 560
His Glu Asp Val Ser Leu Gly Glu Leu Leu Gly Lys Gly Asn Phe Gly
                565                 570                 575
Glu Val Tyr Lys Gly Thr Leu Lys Asp Lys Thr Pro Val Ala Ile Lys
            580                 585                 590
Thr Cys Lys Glu Asp Leu Pro Gln Glu Leu Lys Ile Lys Phe Leu Gln
            595                 600                 605
```

```
Glu Ala Lys Ile Leu Lys Gln Tyr Asp His Pro Asn Ile Val Lys Leu
    610                 615                 620
Ile Gly Val Cys Thr Gln Arg Gln Pro Val Tyr Ile Ile Met Glu Leu
625                 630                 635                 640
Val Pro Gly Gly Asp Phe Leu Thr Phe Leu Arg Lys Arg Lys Asp Glu
                645                 650                 655
Leu Lys Leu Lys Gln Leu Val Arg Phe Ser Leu Asp Val Ala Ala Gly
                660                 665                 670
Met Leu Tyr Leu Glu Ser Lys Asn Cys Ile His Arg Asp Leu Ala Ala
            675                 680                 685
Arg Asn Cys Leu Val Gly Glu Asn Asn Thr Leu Lys Ile Ser Asp Phe
    690                 695                 700
Gly Met Ser Arg Gln Glu Asp Gly Gly Val Tyr Ser Ser Ser Gly Leu
705                 710                 715                 720
Lys Gln Ile Pro Ile Lys Trp Thr Ala Pro Glu Ala Leu Asn Tyr Gly
                725                 730                 735
Arg Tyr Ser Ser Glu Ser Asp Val Trp Ser Phe Gly Ile Leu Leu Trp
                740                 745                 750
Glu Thr Phe Ser Leu Gly Val Cys Pro Tyr Pro Gly Met Thr Asn Gln
            755                 760                 765
Gln Ala Arg Glu Gln Val Glu Arg Gly Tyr Arg Met Ser Ala Pro Gln
    770                 775                 780
Asn Cys Pro Glu Glu Val Phe Thr Ile Met Met Lys Cys Trp Asp Tyr
785                 790                 795                 800
Lys Pro Glu Asn Arg Pro Lys Phe Asn Asp Leu His Lys Glu Leu Thr
                805                 810                 815
Val Ile Lys Lys Met Ile Thr
                820

<210> SEQ ID NO 64
<211> LENGTH: 822
<212> TYPE: PRT
<213> ORGANISM: Homo sapiens

<400> SEQUENCE: 64

Met Gly Phe Gly Ser Asp Leu Lys Asn Ser His Glu Ala Val Leu Lys
1               5                   10                  15
Leu Gln Asp Trp Glu Leu Arg Leu Leu Glu Thr Val Lys Lys Phe Met
                20                  25                  30
Ala Leu Arg Ile Lys Ser Asp Lys Glu Tyr Ala Ser Thr Leu Gln Asn
            35                  40                  45
Leu Cys Asn Gln Val Asp Lys Glu Ser Thr Val Gln Met Asn Tyr Val
    50                  55                  60
Ser Asn Val Ser Lys Ser Trp Leu Leu Met Ile Gln Gln Thr Glu Gln
65                  70                  75                  80
Leu Ser Arg Ile Met Lys Thr His Ala Glu Asp Leu Asn Ser Gly Pro
                85                  90                  95
Leu His Arg Leu Thr Met Met Ile Lys Asp Lys Gln Gln Val Lys Lys
                100                 105                 110
Ser Tyr Ile Gly Val His Gln Gln Ile Glu Ala Glu Met Ile Lys Val
            115                 120                 125
Thr Lys Thr Glu Leu Glu Lys Leu Lys Cys Ser Tyr Arg Gln Leu Ile
    130                 135                 140
Lys Glu Met Asn Ser Ala Lys Glu Lys Tyr Lys Glu Ala Leu Ala Lys
145                 150                 155                 160
```

```
Gly Lys Glu Thr Glu Lys Ala Lys Glu Arg Tyr Asp Lys Ala Thr Met
                165                 170                 175
Lys Leu His Met Leu His Asn Gln Tyr Val Leu Ala Leu Lys Gly Ala
            180                 185                 190
Gln Leu His Gln Asn Gln Tyr Tyr Asp Ile Thr Leu Pro Leu Leu Leu
        195                 200                 205
Asp Ser Leu Gln Lys Met Gln Glu Met Ile Lys Ala Leu Lys Gly
    210                 215                 220
Ile Phe Asp Glu Tyr Ser Gln Ile Thr Ser Leu Val Thr Glu Ile
225                 230                 235                 240
Val Asn Val His Lys Glu Ile Gln Met Ser Val Glu Gln Ile Asp Pro
                245                 250                 255
Ser Thr Glu Tyr Asn Asn Phe Ile Asp Val His Arg Thr Thr Ala Ala
            260                 265                 270
Lys Glu Gln Glu Ile Glu Phe Asp Thr Ser Leu Leu Glu Glu Asn Glu
        275                 280                 285
Asn Leu Gln Ala Asn Glu Ile Met Trp Asn Asn Leu Thr Ala Glu Ser
    290                 295                 300
Leu Gln Val Met Leu Lys Thr Leu Ala Glu Glu Leu Met Gln Thr Gln
305                 310                 315                 320
Gln Met Leu Leu Asn Lys Glu Glu Ala Val Leu Glu Leu Glu Lys Arg
                325                 330                 335
Ile Glu Glu Ser Ser Glu Thr Cys Glu Lys Lys Ser Asp Ile Val Leu
            340                 345                 350
Leu Leu Ser Gln Lys Gln Ala Leu Glu Glu Leu Lys Gln Ser Val Gln
        355                 360                 365
Gln Leu Arg Cys Thr Glu Ala Lys Phe Ser Ala Gln Lys Glu Leu Leu
    370                 375                 380
Glu Gln Lys Val Gln Glu Asn Asp Gly Lys Glu Pro Pro Pro Val Val
385                 390                 395                 400
Asn Tyr Glu Glu Asp Ala Arg Ser Val Thr Ser Met Glu Arg Lys Glu
                405                 410                 415
Arg Leu Ser Lys Phe Glu Ser Ile Arg His Ser Ile Ala Gly Ile Ile
            420                 425                 430
Arg Ser Pro Lys Ser Ala Val Gly Ser Ser Ala Leu Ser Asp Met Ile
        435                 440                 445
Ser Ile Ser Glu Lys Pro Leu Ala Glu Gln Asp Trp Tyr His Gly Ala
    450                 455                 460
Ile Pro Arg Ile Glu Ala Gln Glu Leu Leu Lys Lys Gln Gly Asp Phe
465                 470                 475                 480
Leu Val Arg Glu Ser His Gly Lys Pro Gly Glu Tyr Val Leu Ser Val
                485                 490                 495
Tyr Ser Asp Gly Gln Arg Arg His Phe Ile Ile Gln Tyr Val Asp Asn
            500                 505                 510
Met Tyr Arg Phe Glu Gly Thr Gly Phe Ser Asn Ile Pro Gln Leu Ile
        515                 520                 525
Asp His His Tyr Thr Thr Lys Gln Val Ile Thr Lys Lys Ser Gly Val
    530                 535                 540
Val Leu Leu Asn Pro Ile Pro Lys Asp Lys Lys Trp Ile Leu Ser His
545                 550                 555                 560
Glu Asp Val Ile Leu Gly Glu Leu Leu Gly Lys Gly Asn Phe Gly Glu
                565                 570                 575
```

```
Val Tyr Lys Gly Thr Leu Lys Asp Lys Thr Ser Val Ala Val Lys Thr
            580                 585                 590

Cys Lys Glu Asp Leu Pro Gln Glu Leu Lys Ile Lys Phe Leu Gln Glu
            595                 600                 605

Ala Lys Ile Leu Lys Gln Tyr Asp His Pro Asn Ile Val Lys Leu Ile
            610                 615                 620

Gly Val Cys Thr Gln Arg Gln Pro Val Tyr Ile Ile Met Glu Leu Val
625                 630                 635                 640

Ser Gly Gly Asp Phe Leu Thr Phe Leu Arg Arg Lys Lys Asp Glu Leu
                645                 650                 655

Lys Leu Lys Gln Leu Val Lys Phe Ser Leu Asp Ala Ala Gly Met
            660                 665                 670

Leu Tyr Leu Glu Ser Lys Asn Cys Ile His Arg Asp Leu Ala Ala Arg
            675                 680                 685

Asn Cys Leu Val Gly Glu Asn Asn Val Leu Lys Ile Ser Asp Phe Gly
            690                 695                 700

Met Ser Arg Gln Glu Asp Gly Gly Val Tyr Ser Ser Ser Gly Leu Lys
705                 710                 715                 720

Gln Ile Pro Ile Lys Trp Thr Ala Pro Glu Ala Leu Asn Tyr Gly Arg
                725                 730                 735

Tyr Ser Ser Glu Ser Asp Val Trp Ser Phe Gly Ile Leu Leu Trp Glu
            740                 745                 750

Thr Phe Ser Leu Gly Val Cys Pro Tyr Pro Gly Met Thr Asn Gln Gln
            755                 760                 765

Ala Arg Glu Gln Val Glu Arg Gly Tyr Arg Met Ser Ala Pro Gln His
            770                 775                 780

Cys Pro Glu Asp Ile Ser Lys Ile Met Met Lys Cys Trp Asp Tyr Lys
785                 790                 795                 800

Pro Glu Asn Arg Pro Lys Phe Ser Glu Leu Gln Lys Glu Leu Thr Ile
                805                 810                 815

Ile Lys Arg Lys Leu Thr
            820

<210> SEQ ID NO 65
<211> LENGTH: 116
<212> TYPE: PRT
<213> ORGANISM: Mus musculus

<400> SEQUENCE: 65

Met Arg Asn Ser Lys Thr Ala Ile Ser Phe Phe Ile Leu Val Ala Val
1               5                   10                  15

Leu Gly Ser Gln Ala Gly Leu Ile Gln Glu Met Glu Lys Glu Asp Arg
            20                  25                  30

Arg Tyr Asn Pro Pro Ile Ile His Gln Gly Phe Gln Asp Thr Ser Ser
            35                  40                  45

Asp Cys Cys Phe Ser Tyr Ala Thr Gln Ile Pro Cys Lys Arg Phe Ile
        50                  55                  60

Tyr Tyr Phe Pro Thr Ser Gly Gly Cys Ile Lys Pro Gly Ile Ile Phe
65                  70                  75                  80

Ile Ser Arg Arg Gly Thr Gln Val Cys Ala Asp Pro Ser Asp Arg Arg
            85                  90                  95

Val Gln Arg Cys Leu Ser Thr Leu Lys Gln Gly Pro Arg Ser Gly Asn
            100                 105                 110

Lys Val Ile Ala
            115
```

<210> SEQ ID NO 66
<211> LENGTH: 120
<212> TYPE: PRT
<213> ORGANISM: Homo sapiens

<400> SEQUENCE: 66

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
            20                  25                  30

Met Ser Lys Leu Pro Leu Glu Asn Pro Val Leu Leu Asp Arg Phe His
        35                  40                  45

Ala Thr Ser Ala Asp Cys Cys Ile Ser Tyr Thr Pro Arg Ser Ile Pro
    50                  55                  60

Cys Ser Leu Leu Glu Ser Tyr Phe Glu Thr Asn Ser Glu Cys Ser Lys
65                  70                  75                  80

Pro Gly Val Ile Phe Leu Thr Lys Lys Gly Arg Arg Phe Cys Ala Asn
                85                  90                  95

Pro Ser Asp Lys Gln Val Gln Val Cys Met Arg Met Leu Lys Leu Asp
            100                 105                 110

Thr Arg Ile Lys Thr Arg Lys Asn
        115                 120

<210> SEQ ID NO 67
<211> LENGTH: 264
<212> TYPE: PRT
<213> ORGANISM: Mus musculus

<400> SEQUENCE: 67

Met Glu Ser Gly Phe Thr Ser Lys Asp Thr Tyr Leu Ser His Phe Asn
1               5                   10                  15

Pro Arg Asp Tyr Leu Glu Lys Tyr Tyr Ser Phe Gly Ser Arg His Cys
            20                  25                  30

Ala Glu Asn Glu Ile Leu Arg His Leu Leu Lys Asn Leu Phe Lys Ile
        35                  40                  45

Phe Cys Leu Gly Ala Val Lys Gly Glu Leu Leu Ile Asp Ile Gly Ser
    50                  55                  60

Gly Pro Thr Ile Tyr Gln Leu Leu Ser Ala Cys Glu Ser Phe Thr Glu
65                  70                  75                  80

Ile Ile Val Ser Asp Tyr Thr Asp Gln Asn Leu Trp Glu Leu Gln Lys
                85                  90                  95

Trp Leu Lys Glu Pro Gly Ala Phe Asp Trp Ser Pro Val Val Thr
            100                 105                 110

Tyr Val Cys Asp Leu Glu Gly Asn Arg Met Lys Gly Pro Glu Lys Glu
        115                 120                 125

Glu Lys Leu Arg Arg Ala Ile Lys Gln Val Leu Lys Cys Asp Val Thr
    130                 135                 140

Gln Ser Gln Pro Leu Gly Gly Val Ser Leu Pro Ala Asp Cys Leu
145                 150                 155                 160

Leu Ser Thr Leu Cys Leu Asp Ala Ala Cys Pro Asp Leu Pro Ala Tyr
                165                 170                 175

Arg Thr Ala Leu Arg Asn Leu Gly Ser Leu Leu Lys Pro Gly Gly Phe
            180                 185                 190

Leu Val Met Val Asp Ala Leu Lys Ser Ser Tyr Tyr Met Ile Gly Glu
        195                 200                 205

-continued

Gln Lys Phe Ser Ser Leu Pro Leu Gly Trp Glu Thr Val Arg Asp Ala
    210                 215                 220

Val Glu Glu Ala Gly Tyr Thr Ile Glu Gln Phe Glu Val Ile Ser Gln
225                 230                 235                 240

Asn Tyr Ser Ser Thr Thr Ser Asn Asn Glu Gly Leu Phe Ser Leu Val
                245                 250                 255

Gly Arg Lys Pro Gly Arg Ser Glu
            260

<210> SEQ ID NO 68
<211> LENGTH: 264
<212> TYPE: PRT
<213> ORGANISM: Homo sapiens

<400> SEQUENCE: 68

Met Glu Ser Gly Phe Thr Ser Lys Asp Thr Tyr Leu Ser His Phe Asn
1               5                   10                  15

Pro Arg Asp Tyr Leu Glu Lys Tyr Tyr Lys Phe Gly Ser Arg His Ser
                20                  25                  30

Ala Glu Ser Gln Ile Leu Lys His Leu Leu Lys Asn Leu Phe Lys Ile
            35                  40                  45

Phe Cys Leu Asp Gly Val Lys Gly Asp Leu Leu Ile Asp Ile Gly Ser
        50                  55                  60

Gly Pro Thr Ile Tyr Gln Leu Leu Ser Ala Cys Glu Ser Phe Lys Glu
65                  70                  75                  80

Ile Val Val Thr Asp Tyr Ser Asp Gln Asn Leu Gln Glu Leu Glu Lys
                85                  90                  95

Trp Leu Lys Lys Glu Pro Glu Ala Phe Asp Trp Ser Pro Val Val Thr
            100                 105                 110

Tyr Val Cys Asp Leu Glu Gly Asn Arg Val Lys Gly Pro Glu Lys Glu
        115                 120                 125

Glu Lys Leu Arg Gln Ala Val Lys Gln Val Leu Lys Cys Asp Val Thr
130                 135                 140

Gln Ser Gln Pro Leu Gly Ala Val Pro Leu Pro Pro Ala Asp Cys Val
145                 150                 155                 160

Leu Ser Thr Leu Cys Leu Asp Ala Ala Cys Pro Asp Leu Pro Thr Tyr
                165                 170                 175

Cys Arg Ala Leu Arg Asn Leu Gly Ser Leu Leu Lys Pro Gly Gly Phe
            180                 185                 190

Leu Val Ile Met Asp Ala Leu Lys Ser Ser Tyr Tyr Met Ile Gly Glu
        195                 200                 205

Gln Lys Phe Ser Ser Leu Pro Leu Gly Arg Glu Ala Val Glu Ala Ala
    210                 215                 220

Val Lys Glu Ala Gly Tyr Thr Ile Glu Trp Phe Glu Val Ile Ser Gln
225                 230                 235                 240

Ser Tyr Ser Ser Thr Met Ala Asn Asn Glu Gly Leu Phe Ser Leu Val
                245                 250                 255

Ala Arg Lys Leu Ser Arg Pro Leu
            260

<210> SEQ ID NO 69
<211> LENGTH: 158
<212> TYPE: PRT
<213> ORGANISM: Mus musculus

<400> SEQUENCE: 69

```
Met Ser Gly Ile Ala Leu Ser Arg Leu Ala Gln Glu Arg Lys Ala Trp
1               5                   10                  15

Arg Lys Asp His Pro Phe Gly Phe Val Ala Val Pro Thr Lys Asn Pro
            20                  25                  30

Asp Gly Thr Met Asn Leu Met Asn Trp Glu Cys Ala Ile Pro Gly Lys
        35                  40                  45

Lys Gly Thr Pro Trp Glu Gly Gly Leu Phe Lys Leu Arg Met Leu Phe
    50                  55                  60

Lys Asp Asp Tyr Pro Ser Ser Pro Pro Lys Cys Lys Phe Glu Pro Pro
65                  70                  75                  80

Leu Phe His Pro Asn Val Tyr Pro Ser Gly Thr Val Cys Leu Ser Ile
                85                  90                  95

Leu Glu Glu Asp Lys Asp Trp Arg Pro Ala Ile Thr Ile Lys Gln Ile
                100                 105                 110

Leu Leu Gly Ile Gln Glu Leu Leu Asn Glu Pro Asn Ile Gln Asp Pro
            115                 120                 125

Ala Gln Ala Glu Ala Tyr Thr Ile Tyr Cys Gln Asn Arg Val Glu Tyr
        130                 135                 140

Glu Lys Arg Val Arg Ala Gln Ala Lys Lys Phe Ala Pro Ser
145                 150                 155
```

<210> SEQ ID NO 70
<211> LENGTH: 158
<212> TYPE: PRT
<213> ORGANISM: Homo sapiens

<400> SEQUENCE: 70

```
Met Ser Gly Ile Ala Leu Ser Arg Leu Ala Gln Glu Arg Lys Ala Trp
1               5                   10                  15

Arg Lys Asp His Pro Phe Gly Phe Val Ala Val Pro Thr Lys Asn Pro
            20                  25                  30

Asp Gly Thr Met Asn Leu Met Asn Trp Glu Cys Ala Ile Pro Gly Lys
        35                  40                  45

Lys Gly Thr Pro Trp Glu Gly Gly Leu Phe Lys Leu Arg Met Leu Phe
    50                  55                  60

Lys Asp Asp Tyr Pro Ser Ser Pro Pro Lys Cys Lys Phe Glu Pro Pro
65                  70                  75                  80

Leu Phe His Pro Asn Val Tyr Pro Ser Gly Thr Val Cys Leu Ser Ile
                85                  90                  95

Leu Glu Glu Asp Lys Asp Trp Arg Pro Ala Ile Thr Ile Lys Gln Ile
                100                 105                 110

Leu Leu Gly Ile Gln Glu Leu Leu Asn Glu Pro Asn Ile Gln Asp Pro
            115                 120                 125

Ala Gln Ala Glu Ala Tyr Thr Ile Tyr Cys Gln Asn Arg Val Glu Tyr
        130                 135                 140

Glu Lys Arg Val Arg Ala Gln Ala Lys Lys Phe Ala Pro Ser
145                 150                 155
```

<210> SEQ ID NO 71
<211> LENGTH: 109
<212> TYPE: PRT
<213> ORGANISM: Homo sapiens

<400> SEQUENCE: 71

```
Met Leu Lys Leu Thr Pro Leu Pro Ser Lys Met Lys Val Ser Ala Ala
1               5                   10                  15
```

-continued

```
Leu Leu Cys Leu Leu Met Ala Ala Thr Phe Ser Pro Gln Gly Leu
             20                  25                  30

Ala Gln Pro Asp Ser Val Ser Ile Pro Ile Thr Cys Cys Phe Asn Val
         35                  40                  45

Ile Asn Arg Lys Ile Pro Ile Gln Arg Leu Glu Ser Tyr Thr Arg Ile
 50                  55                  60

Thr Asn Ile Gln Cys Pro Lys Glu Ala Val Ile Phe Lys Thr Gln Arg
 65                  70                  75                  80

Gly Lys Glu Val Cys Ala Asp Pro Lys Glu Arg Trp Val Arg Asp Ser
                 85                  90                  95

Met Lys His Leu Asp Gln Ile Phe Gln Asn Leu Lys Pro
                100                 105

<210> SEQ ID NO 72
<211> LENGTH: 462
<212> TYPE: PRT
<213> ORGANISM: Mus musculus

<400> SEQUENCE: 72

Met Gly Pro Trp Thr His Ser Leu Arg Ala Val Leu Leu Val Leu
 1               5                  10                  15

Leu Gly Val Cys Thr Val Arg Ser Asp Thr Pro Ala Asn Cys Thr Tyr
             20                  25                  30

Pro Asp Leu Leu Gly Thr Trp Val Phe Gln Val Gly Pro Arg Ser Ser
         35                  40                  45

Arg Ser Asp Ile Asn Cys Ser Val Met Glu Ala Thr Glu Glu Lys Val
 50                  55                  60

Val Val His Leu Lys Lys Leu Asp Thr Ala Tyr Asp Glu Leu Gly Asn
 65                  70                  75                  80

Ser Gly His Phe Thr Leu Ile Tyr Asn Gln Gly Phe Glu Ile Val Leu
                 85                  90                  95

Asn Asp Tyr Lys Trp Phe Ala Phe Phe Lys Tyr Glu Val Arg Gly His
                100                 105                 110

Thr Ala Ile Ser Tyr Cys His Glu Thr Met Thr Gly Trp Val His Asp
            115                 120                 125

Val Leu Gly Arg Asn Trp Ala Cys Phe Val Gly Lys Lys Val Glu Ser
        130                 135                 140

His Ile Glu Lys Val Asn Met Asn Ala Ala His Leu Gly Gly Leu Gln
145                 150                 155                 160

Glu Arg Tyr Ser Glu Arg Leu Tyr Thr His Asn His Asn Phe Val Lys
                165                 170                 175

Ala Ile Asn Thr Val Gln Lys Ser Trp Thr Ala Thr Ala Tyr Lys Glu
            180                 185                 190

Tyr Glu Lys Met Ser Leu Arg Asp Leu Ile Arg Arg Ser Gly His Ser
        195                 200                 205

Gln Arg Ile Pro Arg Pro Lys Pro Ala Pro Met Thr Asp Glu Ile Gln
    210                 215                 220

Gln Gln Ile Leu Asn Leu Pro Glu Ser Trp Asp Trp Arg Asn Val Gln
225                 230                 235                 240

Gly Val Asn Tyr Val Ser Pro Val Arg Asn Gln Glu Ser Cys Gly Ser
                245                 250                 255

Cys Tyr Ser Phe Ala Ser Met Gly Met Leu Glu Ala Arg Ile Arg Ile
            260                 265                 270

Leu Thr Asn Asn Ser Gln Thr Pro Ile Leu Ser Pro Gln Glu Val Val
```

```
                275                 280                 285
Ser Cys Ser Pro Tyr Ala Gln Gly Cys Asp Gly Gly Phe Pro Tyr Leu
    290                 295                 300
Ile Ala Gly Lys Tyr Ala Gln Asp Phe Gly Val Val Glu Glu Ser Cys
305                 310                 315                 320
Phe Pro Tyr Thr Ala Lys Asp Ser Pro Cys Lys Pro Arg Glu Asn Cys
                325                 330                 335
Leu Arg Tyr Tyr Ser Ser Asp Tyr Tyr Val Gly Gly Phe Tyr Gly
                340                 345                 350
Gly Cys Asn Glu Ala Leu Met Lys Leu Glu Leu Val Lys His Gly Pro
                355                 360                 365
Met Ala Val Ala Phe Glu Val His Asp Phe Leu His Tyr His Ser
    370                 375                 380
Gly Ile Tyr His His Thr Gly Leu Ser Asp Pro Phe Asn Pro Phe Glu
385                 390                 395                 400
Leu Thr Asn His Ala Val Leu Leu Val Gly Tyr Gly Arg Asp Pro Val
                405                 410                 415
Thr Gly Ile Glu Tyr Trp Ile Ile Lys Asn Ser Trp Gly Ser Asn Trp
                420                 425                 430
Gly Glu Ser Gly Tyr Phe Arg Ile Arg Arg Gly Thr Asp Glu Cys Ala
                435                 440                 445
Ile Glu Ser Ile Ala Val Ala Ala Ile Pro Ile Pro Lys Leu
    450                 455                 460

<210> SEQ ID NO 73
<211> LENGTH: 463
<212> TYPE: PRT
<213> ORGANISM: Homo sapiens

<400> SEQUENCE: 73

Met Gly Ala Gly Pro Ser Leu Leu Leu Ala Leu Leu Leu Leu Leu
 1               5                  10                  15

Ser Gly Asp Gly Ala Val Arg Cys Asp Thr Pro Ala Asn Cys Thr Tyr
                20                  25                  30

Leu Asp Leu Leu Gly Thr Trp Val Phe Gln Val Gly Ser Ser Gly Ser
            35                  40                  45

Gln Arg Asp Val Asn Cys Ser Val Met Gly Pro Gln Glu Lys Lys Val
    50                  55                  60

Val Val Tyr Leu Gln Lys Leu Asp Thr Ala Tyr Asp Asp Leu Gly Asn
65                  70                  75                  80

Ser Gly His Phe Thr Ile Ile Tyr Asn Gln Gly Phe Glu Ile Val Leu
                85                  90                  95

Asn Asp Tyr Lys Trp Phe Ala Phe Phe Lys Tyr Lys Glu Glu Gly Ser
                100                 105                 110

Lys Val Thr Thr Tyr Cys Asn Glu Thr Met Thr Gly Trp Val His Asp
            115                 120                 125

Val Leu Gly Arg Asn Trp Ala Cys Phe Thr Gly Lys Lys Val Gly Thr
    130                 135                 140

Ala Ser Glu Asn Val Tyr Val Asn Thr Ala His Leu Lys Asn Ser Gln
145                 150                 155                 160

Glu Lys Tyr Ser Asn Arg Leu Tyr Lys Tyr Asp His Asn Phe Val Lys
                165                 170                 175

Ala Ile Asn Ala Ile Gln Lys Ser Trp Thr Ala Thr Thr Tyr Met Glu
                180                 185                 190
```

```
Tyr Glu Thr Leu Thr Leu Gly Asp Met Ile Arg Arg Ser Gly Gly His
            195                 200                 205

Ser Arg Lys Ile Pro Arg Pro Lys Pro Ala Pro Leu Thr Ala Glu Ile
210                 215                 220

Gln Gln Lys Ile Leu His Leu Pro Thr Ser Trp Asp Trp Arg Asn Val
225                 230                 235                 240

His Gly Ile Asn Phe Val Ser Pro Val Arg Asn Gln Ala Ser Cys Gly
                245                 250                 255

Ser Cys Tyr Ser Phe Ala Ser Met Gly Met Leu Glu Ala Arg Ile Arg
            260                 265                 270

Ile Leu Thr Asn Asn Ser Gln Thr Pro Ile Leu Ser Pro Gln Glu Val
            275                 280                 285

Val Ser Cys Ser Gln Tyr Ala Gln Gly Cys Glu Gly Phe Pro Tyr
            290                 295                 300

Leu Ile Ala Gly Lys Tyr Ala Gln Asp Phe Gly Leu Val Glu Glu Ala
305                 310                 315                 320

Cys Phe Pro Tyr Thr Gly Thr Asp Ser Pro Cys Lys Met Lys Glu Asp
                325                 330                 335

Cys Phe Arg Tyr Tyr Ser Ser Glu Tyr His Tyr Val Gly Gly Phe Tyr
            340                 345                 350

Gly Gly Cys Asn Glu Ala Leu Met Lys Leu Glu Leu Val His His Gly
            355                 360                 365

Pro Met Ala Val Ala Phe Glu Val Tyr Asp Asp Phe Leu His Tyr Lys
370                 375                 380

Lys Gly Ile Tyr His His Thr Gly Leu Arg Asp Pro Phe Asn Pro Phe
385                 390                 395                 400

Glu Leu Thr Asn His Ala Val Leu Leu Val Gly Tyr Gly Thr Asp Ser
                405                 410                 415

Ala Ser Gly Met Asp Tyr Trp Ile Val Lys Asn Ser Trp Gly Thr Gly
            420                 425                 430

Trp Gly Glu Asn Gly Tyr Phe Arg Ile Arg Arg Gly Thr Asp Glu Cys
            435                 440                 445

Ala Ile Glu Ser Ile Ala Val Ala Ala Thr Pro Ile Pro Lys Leu
450                 455                 460

<210> SEQ ID NO 74
<211> LENGTH: 21
<212> TYPE: DNA
<213> ORGANISM: Homo sapiens

<400> SEQUENCE: 74
cctcccctct tcaagggtct a                                          21

<210> SEQ ID NO 75
<211> LENGTH: 21
<212> TYPE: DNA
<213> ORGANISM: Homo sapiens

<400> SEQUENCE: 75
aggagtaaga cccctggacc a                                          21

<210> SEQ ID NO 76
<211> LENGTH: 21
<212> TYPE: DNA
<213> ORGANISM: Homo sapiens

<400> SEQUENCE: 76
```

```
cccaatggga attcactcac c                                               21

<210> SEQ ID NO 77
<211> LENGTH: 22
<212> TYPE: DNA
<213> ORGANISM: Homo sapiens

<400> SEQUENCE: 77
gcttccactc tcgtaggctt tc                                              22

<210> SEQ ID NO 78
<211> LENGTH: 25
<212> TYPE: DNA
<213> ORGANISM: Homo sapiens

<400> SEQUENCE: 78
tcttaaccac cagatcattc cttct                                           25

<210> SEQ ID NO 79
<211> LENGTH: 20
<212> TYPE: DNA
<213> ORGANISM: Homo sapiens

<400> SEQUENCE: 79
ggatactgcg agcaaatggg                                                 20

<210> SEQ ID NO 80
<211> LENGTH: 347
<212> TYPE: PRT
<213> ORGANISM: Homo sapiens

<400> SEQUENCE: 80
```

Met Ser Lys Arg Pro Ser Tyr Ala Pro Pro Thr Pro Ala Pro Ala
 1               5                  10                  15

Thr Gln Met Pro Ser Thr Pro Gly Phe Val Gly Tyr Asn Pro Tyr Ser
            20                  25                  30

His Leu Ala Tyr Asn Asn Tyr Arg Leu Gly Gly Asn Pro Gly Thr Asn
        35                  40                  45

Ser Arg Val Thr Ala Ser Ser Gly Ile Thr Ile Pro Lys Pro Pro Lys
    50                  55                  60

Pro Pro Asp Lys Pro Leu Met Pro Tyr Met Arg Tyr Ser Arg Lys Val
65                  70                  75                  80

Trp Asp Gln Val Lys Ala Ser Asn Pro Asp Leu Lys Leu Trp Glu Ile
                85                  90                  95

Gly Lys Ile Ile Gly Gly Met Trp Arg Asp Leu Thr Asp Glu Glu Lys
            100                 105                 110

Gln Glu Tyr Leu Asn Glu Tyr Glu Ala Glu Lys Ile Glu Tyr Asn Glu
        115                 120                 125

Ser Met Lys Ala Tyr His Asn Ser Pro Ala Tyr Leu Ala Tyr Ile Asn
    130                 135                 140

Ala Lys Ser Arg Ala Glu Ala Ala Leu Glu Glu Glu Ser Arg Gln Arg
145                 150                 155                 160

Gln Ser Arg Met Glu Lys Gly Glu Pro Tyr Met Ser Ile Gln Pro Ala
                165                 170                 175

Glu Asp Pro Asp Asp Tyr Asp Asp Gly Phe Ser Met Lys His Thr Ala
            180                 185                 190

Thr Ala Arg Phe Gln Arg Asn His Arg Leu Ile Ser Glu Ile Leu Ser
        195                 200                 205

```
Glu Ser Val Val Pro Asp Val Arg Ser Val Val Thr Thr Ala Arg Met
    210                 215                 220

Gln Val Leu Lys Arg Gln Val Gln Ser Leu Met Val His Gln Arg Lys
225                 230                 235                 240

Leu Glu Ala Glu Leu Leu Gln Ile Glu Glu Arg His Gln Glu Lys Lys
                245                 250                 255

Arg Lys Phe Leu Glu Ser Thr Asp Ser Phe Asn Asn Glu Leu Lys Arg
            260                 265                 270

Leu Cys Gly Leu Lys Val Glu Val Asp Met Glu Lys Ile Ala Ala Glu
        275                 280                 285

Ile Ala Gln Ala Glu Glu Gln Ala Arg Lys Arg Gln Glu Glu Arg Glu
    290                 295                 300

Lys Glu Ala Ala Glu Gln Ala Glu Arg Ser Gln Ser Ser Ile Val Pro
305                 310                 315                 320

Glu Glu Glu Gln Ala Ala Asn Lys Gly Glu Glu Lys Lys Asp Asp Glu
                325                 330                 335

Asn Ile Pro Met Glu Thr Gly Asn Ser Pro Ala
            340                 345
```

<210> SEQ ID NO 81
<211> LENGTH: 197
<212> TYPE: PRT
<213> ORGANISM: Homo sapiens

<400> SEQUENCE: 81

```
Met Trp Val Gln Thr Arg Pro Ser Ser Ala Ser Tyr Lys Ser Trp Gly
1               5                   10                  15

Pro Gly Thr Ala Asp Thr His Thr Met Arg Leu Ser Arg Arg Pro Glu
                20                  25                  30

Thr Phe Leu Leu Ala Phe Val Leu Leu Cys Thr Leu Gly Leu Gly
            35                  40                  45

Cys Pro Leu His Cys Glu Ile Cys Thr Ala Ala Gly Ser Arg Cys His
        50                  55                  60

Gly Gln Met Lys Thr Cys Ser Ser Asp Lys Asp Thr Cys Val Leu Leu
65                  70                  75                  80

Val Gly Lys Ala Thr Ser Lys Gly Lys Glu Leu Val His Thr Tyr Lys
                85                  90                  95

Gly Cys Ile Arg Ser Gln Asp Cys Tyr Ser Gly Val Ile Ser Thr Thr
            100                 105                 110

Met Gly Pro Lys Asp His Met Val Thr Ser Ser Phe Cys Cys Gln Ser
        115                 120                 125

Asp Gly Cys Asn Ser Ala Phe Leu Ser Val Pro Leu Thr Asn Leu Thr
    130                 135                 140

Glu Asn Gly Leu Met Cys Pro Ala Cys Thr Ala Ser Phe Arg Asp Lys
145                 150                 155                 160

Cys Met Gly Pro Met Thr His Cys Thr Gly Lys Glu Asn His Cys Val
                165                 170                 175

Ser Leu Ser Gly His Val Gln Ala Gly Glu Trp Cys Leu Asn Leu Trp
            180                 185                 190

Lys Arg Lys Gln Asn
        195
```

<210> SEQ ID NO 82
<211> LENGTH: 285
<212> TYPE: PRT
<213> ORGANISM: Homo sapiens

```
<400> SEQUENCE: 82

Met Ala Val Ser Glu Ser Gln Leu Lys Lys Met Val Ser Lys Pro Gln
 1               5                  10                  15

Ser Asp Leu Leu Gly Leu Ile Gln Val Met Ile Val Val Phe Gly Asp
            20                  25                  30

Glu Pro Pro Val Phe Ser Arg Pro Ile Ser Ala Ser Tyr Pro Pro Tyr
        35                  40                  45

Gln Ala Thr Gly Pro Pro Asn Thr Ser Tyr Met Pro Gly Met Pro Gly
    50                  55                  60

Gly Ile Ser Pro Tyr Pro Ser Gly Tyr Pro Pro Asn Pro Ser Gly Tyr
65                  70                  75                  80

Pro Gly Cys Pro Tyr Pro Pro Gly Gly Pro Tyr Pro Ala Thr Thr Ser
                85                  90                  95

Ser Gln Tyr Pro Ser Gln Pro Pro Val Thr Thr Val Gly Pro Ser Arg
            100                 105                 110

Asp Gly Thr Ile Ser Glu Asp Thr Ile Arg Ala Ser Leu Ile Ser Ala
        115                 120                 125

Val Ser Asp Lys Leu Arg Trp Arg Met Lys Glu Met Asp Arg Ala
130                 135                 140

Gln Ala Glu Leu Asn Ala Leu Lys Arg Thr Glu Glu Asp Leu Lys Lys
145                 150                 155                 160

Gly His Gln Lys Leu Glu Glu Met Val Thr Arg Leu Asp Gln Glu Val
                165                 170                 175

Ala Glu Val Asp Lys Asn Ile Glu Leu Leu Lys Lys Lys Asp Glu Glu
            180                 185                 190

Leu Ser Ser Ala Leu Glu Lys Met Glu Asn Gln Ser Glu Asn Asn Asp
        195                 200                 205

Ile Asp Glu Val Ile Ile Pro Thr Ala Pro Leu Tyr Lys Gln Ile Leu
    210                 215                 220

Asn Leu Tyr Ala Glu Glu Asn Ala Ile Glu Asp Thr Ile Phe Tyr Leu
225                 230                 235                 240

Gly Glu Ala Leu Arg Arg Gly Val Ile Asp Leu Asp Val Phe Leu Lys
                245                 250                 255

His Val Arg Leu Leu Ser Arg Lys Gln Phe Gln Leu Arg Ala Leu Met
            260                 265                 270

Gln Lys Ala Arg Lys Thr Ala Gly Leu Ser Asp Leu Tyr
        275                 280                 285

<210> SEQ ID NO 83
<211> LENGTH: 1946
<212> TYPE: DNA
<213> ORGANISM: Homo sapiens

<400> SEQUENCE: 83
ctgcccgcgg tgtctcagat tcattcttaa ggaactgaga acttaatctt ccaaaatgtc      60
aaaaagacca tcttatgccc cacctcccac cccagctcct gcaacacaaa tgcccagcac     120
accagggttt gtgggataca atccatacag tcatctcgcc tacaacaact acaggctggg     180
agggaacccg ggcaccaaca gccgggtcac ggcatcctct ggtatcacga ttccaaaacc     240
ccccaagcca ccagataagc cgctgatgcc ctacatgagg tacagcagaa aggtctggga     300
ccaagtaaag gcttccaacc ctgacctaaa gttgtgggag attggcaaga ttattggtgg     360
catgtggcga gatctcactg atgaagaaaa acaagaatat ttaaacgaat acgaagcaga     420
```

-continued

```
aaagatagag tacaatgaat ctatgaaggc ctatcataat tccccgcgt accttgctta    480
cataaatgca aaaagtcgtg cagaagctgc tttagaggaa gaaagtcgac agagacaatc    540
tcgcatggag aaaggagaac cgtacatgag cattcagcct gctgaagatc cagatgatta    600
tgatgatggc ttttcaatga agcatacagc caccgcccgt ttccagagaa accaccgcct    660
catcagtgaa attcttagtg agagtgtggt gccagacgtt cggtcagttg tcacaacagc    720
tagaatgcag gtcctcaaac ggcaggtcca gtccttaatg gttcatcagc gaaaactaga    780
agctgaactt cttcaaatag gaacgacaa ccaggagaag aagaggaaat tcctggaaag     840
cacagattca tttaacaatg aacttaaaag gttgtgcggt ctgaaagtag aagtggatat    900
ggagaaaatt gcagctgaga ttgcacaggc agaggaacag gcccgcaaaa ggcaggagga    960
aagggagaag gaggccgcag agcaagctga gcgcagtcag agcagcatcg ttcctgagga   1020
agaacaagca gctaacaaag gcgaggagaa gaaagacgac gagaacattc cgatggagac   1080
aggaaacagc ccagcatgac tttaaacaaa gtgtctaaaa gaccaacctt atattatttc   1140
tacaactgct ttctcctcgt ttaatccata gcactacaga ctaactctca ttcactgtcc   1200
aacagaaata aaatgcaagt cacgtgaaat tttatatttt ctactagtga catattttta   1260
aaagttaagc aaaacaagtg ttttaacaat atgttttatt taattcaaca tatcctaaat   1320
aaaattattt caacacagaa ggaacatttt taaaatcagc tttccttttt ttaaacagtc   1380
tttatacaca tctcaattca gaagctaaat tttcatcgga agtatttgat ctgcatttat   1440
ttaataaatt tcattcattt acagctaaaa agtagatttt catacccaaa ttgttccaac   1500
attcttaaaa gttctttagt cgcactggtt catttcaggg gtttaataac cacatgtggc   1560
tagtggcttc tatattggac agcacagctg tatactgtca gcataactag agtaaaattt   1620
catcttggaa ctgacagtga caaatgtgtg attacagagg agacacacct tgaagaaaca   1680
acagagagcc aacagaatgg tgaagaaggc acgtctactc ctgaggacaa ggagagtggg   1740
caggagggg tcgacagtat ggcagaggaa ggaaccagtg atagtaacac tggctcggag   1800
agcaacagtg caacagtgga ggagccacca acagatccca taccagaaga tgagaaaaaa   1860
gaataagtgt tgccttgttt tgtgtgttct aaatactttt tttaatgaaa aatgttttt    1920
tggttttaat ggtgttacgt ggtttg                                        1946
```

<210> SEQ ID NO 84
<211> LENGTH: 932
<212> TYPE: DNA
<213> ORGANISM: Homo sapiens

<400> SEQUENCE: 84

```
ccggccgtgg gaaaggtgaa tgtgggtcca gacccgcccc tcctcagctt cctataaaag     60
ctggggacca ggtactgctg atacacacac catgaggctc tccaggagac cagagacctt    120
tctgctggcc tttgtgttgc tctgcaccct cctgggtctt gggtgccac tacactgcga    180
aatatgtacg gcggcgggga gcaggtgcca tggccaaatg aagacctgca gcagtgacaa    240
ggacacatgt gtgctcctgg tcgggaaggc tacttcaaag ggcaaggagt tggtgcacac    300
ctacaagggc tgcatcaggt cccaggactg ctactccggc gttatatcca ccaccatggg    360
ccccaaggac cacatggtaa ccagctcctt ctgctgccag agcgacggct gcaacagtgc    420
cttttttgtct gttcccttga ccaatcttac tgagaatggc ctgatgtgcc ccgcctgcac    480
tgcgagcttc agggacaaat gcatgggcc catgacccac tgtactggaa aggaaaacca    540
ctgtgtctcc ttatctggac acgtgcaggc tggtgagtgg tgcctgaatc tctggaaaag    600
```

```
gaaacagaac tagaggtcca aacttctagg ttcgatggga ggagagggtt ccagagaagt      660
gggtgaggat gtgttctggg attatgagga agaagggget gaggtccctg attccagtct      720
gaaatctccc tttcaggtat tttcaaaccc agatttgcta tgcggggctg tgctacagag      780
agtatgtgct ttaccaagcc tggtgctgaa gtacccacag gcaccaatgt cctcttcctc      840
catcatatag agtgcactca ctccccctga aaagctatct gaacaaagga agataatgta      900
gtgtgaagtc cccatttgtc ctcagcctgt aa                                    932
```